United States Patent
Doudna et al.

(10) Patent No.: US 9,688,971 B2
(45) Date of Patent: Jun. 27, 2017

(54) ENDORIBONUCLEASE AND METHODS OF USE THEREOF

(71) Applicant: The Regents of the University of California, Oakland, CA (US)

(72) Inventors: Jennifer A. Doudna, Berkeley, CA (US); Martin Jinek, Zurich (CH); Samuel H. Sternberg, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 249 days.

(21) Appl. No.: 14/403,413

(22) PCT Filed: Jun. 13, 2013

(86) PCT No.: PCT/US2013/045602
§ 371 (c)(1),
(2) Date: Nov. 24, 2014

(87) PCT Pub. No.: WO2013/188638
PCT Pub. Date: Dec. 19, 2013

(65) Prior Publication Data
US 2015/0152398 A1 Jun. 4, 2015

Related U.S. Application Data

(60) Provisional application No. 61/660,414, filed on Jun. 15, 2012.

(51) Int. Cl.
*C12N 9/22* (2006.01)
*C12Q 1/68* (2006.01)

(52) U.S. Cl.
CPC ............. *C12N 9/22* (2013.01); *C12Q 1/6834* (2013.01)

(58) Field of Classification Search
None
See application file for complete search history.

(56) References Cited

U.S. PATENT DOCUMENTS

2011/0217739 A1  9/2011  Terns et al.

FOREIGN PATENT DOCUMENTS

WO  2011143124 A2  11/2011

OTHER PUBLICATIONS

Hale et al. ("Essential features and rational design of CRISPR RNAs that function with the module complex to cleave RNAs" by Hale, et al, (Mol Cell. Epub Jan. 5, 2012, 45(3):292-302).*
Carte; et al., "Binding and cleavage of CRISPR RNA by Cas6.", RNA (Nov. 2010), 16(11):2181-8.
GenBank Direct Submission M33159.1.T. thermophilus insertion sequences Is1000A and Is100B (May 1993).
Haurwitz; et al., "Csy4 relies on an unusual catalytic dyad to position and cleave CRISPR RNA.", EMBO J. (Jun. 2012), 31(12):2824-32.
Lee; et al., "RNA-protein analysis using a conditional CRISPR nuclease.", Proc Natl Acad Sci USA (Apr. 2013), 110(14):5416-21.
Sternberg; et al., "Mechanism of substrate selection by a highly specific CRISPR endoribonuclease.", RNA (Apr. 2012), 18(4):661-72.
UniProt Direct Submission D7BB61_MEISD. CRISPR-associated protein Cas6, (May 2012).
Estarellas, et al. Molecular dynamic simulations of protein/RNA complexes: CRISPR/Csy4 endoribonuclease. Biochim Biophys Acta. Oct. 24, 2014. pii: S0304-4165(14)00357-2. doi: 10.1016/j.bbagen.2014.10.021. [Epub ahead of print].
Ngo; et al., "in the Protein Folding Problem and Tertiary Structure Prediction, 1994, Merz et al. (ed.), Birkhauser, Boston, MA, pp. 433 and 492-495."
Office action dated Jan. 9, 2015 for U.S. Appl. No. 13/671,120.

* cited by examiner

*Primary Examiner* — Suzanne M Noakes
*Assistant Examiner* — Jae W Lee
(74) *Attorney, Agent, or Firm* — Bozicevic Field & Francis, LLP; Paula A. Borden

(57) ABSTRACT

The present disclosure provides variant Cas endoribonucleases, nucleic acids encoding the variant Cas endoribonucleases, and host cells genetically modified with the nucleic acids. The variant Cas endoribonucleases find use in a variety of applications, which are also provided. The present disclosure also provides methods of detecting a specific sequence in a target polyribonucleotide; and methods of regulating production of a target RNA in a eukaryotic cell.

13 Claims, 60 Drawing Sheets

| | | |
|---|---|---|
| YP_003684129 | MMLAALVLPLEGQARPDPDGWRGLVYGLLKEIDPELHTA-QHNPFSLGLGGAEGQWWVRI | 59 |
| ADH62621 | MMLAALVLPLEGQARPDPDGWRGLVYGLLKEIDPELHTA-QHNPFSLGLGGAEGQWWVRI | 59 |
| YP_003506022 | MILAALILPLEGPTRPDPDGWRGLVYGLLKEIDPELHAA-QHNPFSLGLGGALGQWWVRI | 59 |
| YP_143344 (TTHA0078) | MVLAAIVLVLEGEGLPEPLGLRGFFYGLLREVAPEVHDQ-GENPFALGFGGREGAAWARV | 59 |
| YP_006059433 | MVLAALVLVLEGEGLPEPLGLRGFFYGLLREVAPEVHDQ-GENPFALGFGGREGASWARV | 59 |
| YP_005654445 | -MLAALVLTLEGEAPPEPRGLRGFFYGLLQEVAPEVHDQ-GENPFALGFGGKEGAYWARF | 58 |
| ZP_03497188 | MVLVALVLVLEGEGPPEPLGLRGFFYTLLKEAFPELHDQ-GENPFALGFGLRGGEPWARV | 59 |
| YP_004367049 | MLLAALVLPLEGPDRPQPLHARGWVYRLLREAAPEIHDAEGPKPFTVGVGGRPNAVWVRL | 60 |
| | :: .: .*: *** * * :. :: *:.*: .*. . |

| | | |
|---|---|---|
| YP_003684129 | ALLEEGLYARLSPHLFGLVGQSVKLKEP-FRVRAVLQEEHPWASLSTYPRLFQGQASPSL | 118 |
| ADH62621 | ALLEEGLYARLSPHLFGLVGQSVKLKEP-FRVRAVLQEEHPWASLSTYPRLFQGQASPSL | 118 |
| YP_003506022 | AFLEEGLYARLSPHLFGLAGQTVRLKEA-FQVRAVLQEAHPWAGVSTYPKLFQGQATASL | 118 |
| YP_143344 (TTHA0078) | SLIVEGLYARLAPRLYALEGEEVRLGPP-FRVRAVLQEGHPWAGVSTYPRLFQGPPSRDL | 118 |
| YP_006059433 | SLLREELYARLAPRLYALEGEEVRLGPP-FRVRAVLQEGHPWAGVSTYPRLFQGPPSRDL | 118 |
| YP_005654445 | SLLQEGLYARLAPRLFALEGKEVRLGKP-FRVRGVLQEGHPWAGVSTYARLFQGEALPDL | 117 |
| ZP_03497188 | SLLREDLYGRLSPALFGLEGREVRLGRL-FRVRAVLGEDTYRIKAVLEAEHPWAGLTTYARLFQGPHSPNL | 118 |
| YP_004367049 | TCLAEEVYAALSPRLWSQVGLEVRLGEDTYRIKAVLEAEHPWAGLATWPRLFQGEAGPDL | 120 |
| | : : : : . *. ::: .::.: **. |

| | | |
|---|---|---|
| YP_003684129 | GLQFASPTFFRRKGNSYPLPEPKLVFDSLTQRWNAFAPVKVPPEMAET-WERVTITRLQG | 177 |
| ADH62621 | GLQFASPTFFRRKGNSYPLPEPKLVFDSLTQRWNAFAPVKVPPEMAET-WERVTITRLQG | 177 |
| YP_003506022 | GLQFASPTFFRRKGHSYPLPEPRLVFESLTQRWNAFAPVKVPPQEVQEA-WERLLVGQFQG | 177 |
| YP_143344 (TTHA0078) | ALRFASPTFFRRKGVHYPVPEPRIVLESLLRRLEAFGPLKAPEGVREALLERTTVRSLEG | 178 |
| YP_006059433 | ALRFASPTFFRRKGVHYPVPEPRIVLESLLRRLEAFGPLKAPEGVREALLERTTVRSLEG | 178 |
| YP_005654445 | PLRFASPTFFRRKGVHYPLPEPRIVVESLLRRLEAFGPLKAPEGVREALLERTTVRWFEG | 177 |
| ZP_03497188 | PLRFYSPTFFRRKGVQYPLPEPRIVLESLLRRLEAFGPLKAPQEVREALLERTTVRFLEG | 178 |
| YP_004367049 | GLEFASPTFFRRQGANYPLPEPRIVLGSLIERWNAHAPTPVPPEVAERLVEATTLRYLKG | 180 |
| | * * ***** *: :* :** :** :: . :: . . *: |

FIG. 9A

```
YP_003684129      HTQAIRPNPDERGVGFVGRVVYHLPAAKPTEAQWMQALGRFAFYAGVGAKTSLGFGRVRG  237
ADH62621          HTQAIRPNPDERGVGFVGRVVYHLPAAKPTEAQWMQALGRFAFYAGVGAKTSLGFGRVRG  237
YP_003506022      RTHHIAPNQDERGVGFVGRVVVYLPKASPTEAQWLQALGRFAFYAGVGAKTSLGFGRVRM  237
YP_143344 (TTHA0078)  RTLPARTEVDT--AGFVGRVVYHLPRATEEEALWLSALGRFAFYSGVGAKTSLGYGRARA  236
YP_006059433      RTLPARTEVDT--AGFVGRVVYHLPRATEEEALWLSALGRFAFYSGVGAKTSLGYGRARA  236
YP_005654445      KTLKAETEVEA--VGFVGKVVYHLPRATEEEARWLQALGRFAFYSGVGAKTGLGYGRARV  235
ZP_03497188       RTQMARTEVDT--VGFVGKVVYHLPKATEEEALWLSALGRYAFFSGVGAKTSLGYGLARA  236
YP_004367049      HTVSAVGHDRT--VGFRGRVTYHLPRASTEEARWLAALGRFAFFSGVGAKTTLGFGQVRP  238
                    *    .     **  *:. : :  *  **   * ******::: ***** **:*.  . *

YP_003684129      FDPILKEESANGRLDAEDSSSLATPQDPGA  267
ADH62621          FDPILKEESANGRLDAEDSSSLATPQDPGA  267
YP_003506022      FDPLQQER----RPDESEQGALTGTVG-GV  262
YP_143344 (TTHA0078)  ESA---------------------------  239
YP_006059433      ESP---------------------------  239
YP_005654445      G-----------------------------  236
ZP_03497188       FTQVGPQDAET-------------------  247
YP_004367049      YPLLAPSAAPPGP-----------------  251
```

FIG. 9B

```
YP_145470 (TTHB231)  MPQAVVLELVGEKPPLYPARYAHGLFFALLSRVSPELAQKLHEAPRKPFTLAPLPRAGPE   60
YP_006185            MPQAVVLELVGEKPPLYPARYAHGLFFALLSRVSPELAQKLHEAPRKPFTLAPLPRAGPE   60
YP_005641609         MPQAVVLELVGEESPLYPARYAHGLFFALLSRVSPELAQKLHEAPRKPFTLAPLPRVGPE   60
YP_006059769         MPQAVVLELVGEESPLYPGRYAHGLFFALLSRVSPELAQKLHEAPRKPFTLAPLPRVGSE   60
                     ************* .***.**************************************.*

YP_145470 (TTHB231)  GATLKGTLRLRLTTLDDGLFAPFLRALLEAAPDGLPLGDSSYRLARVLATREGHPLAGAT  120
YP_006185            GATLKGTLRLRLTTLDDGLFAPFLRALLEAAPDGLPLGDSSYRLARVLATREGHPLAGAT  120
YP_005641609         GATLKGILRLRLTALDDGLFAPFLRALLEAAPDGLPLGDSSYRLARVLATREGHPLAGAT  120
YP_006059769         GATLKGILRLTILDDGLFAPFLRALLEAAPDGLPLGDSSYRLARVLATREGHPLAGAT   120
                     ****** ***  *.*********************************************

YP_145470 (TTHB231)  SWEELKEAPKREKATFRFLTPTVFATSKPGGRTRYTPLPDPRLIAGSLLDKWQAHSPFPY  180
YP_006185            SWEELKEAPKREKVTFRFLTPTVFATSKPGGRTRYTPLPDPRLIAGSLLDKWQAHSPFPY  180
YP_005641609         SWEELKEAPKREKATFRFLTPTVFATSKPGGRTRYTPLPDPRLIAGSLLDKWQAHSPFPY  180
YP_006059769         SWEELKEAPKREKATFRFLTPTVFATSKPGGRTRYTPLPDPRLIAGSLLDKWQAHSPFPY  180
                     ************* **********************************************

YP_145470 (TTHB231)  NPKEEAALRELFELDLEVAGFRNLRFHRVQAGKGFFPGFTGEATLRLWSQSLEAQEALGR  240
YP_006185            NPKEEAALRGLFELDLEVAGFRNLRFHRVQAGKGFFPGFTGEMTLRLWSQSLEAREALGR  240
YP_005641609         NPKEEAALRELFELDLEVAGFRNLRFHRVQAGKGFFPGFTGEATLRLWSQSLEAQEALGR  240
YP_006059769         NPKEEAALRELFELDLEVAGFRNLRFHRVQAGKSFFPGFTGEMTLRLWSQSLEAQGALGR  240
                     ********* *********************** ********.**********: ****

YP_145470 (TTHB231)  LHALAFFSGVGAKTPYGMGLAVPL  264
YP_006185            LHALAFFSGVGAKTPYGMGLAVPL  264
YP_005641609         LHALAFFSGVGAKTPYGMGLAVPL  264
YP_006059769         LHALAFFSGVGAKTPYGMGLAVPL  264
                     ************************
```

FIG. 10

>gi|55980047|ref|YP_143344.1| hypothetical protein TTHA0078 [Thermus thermophilus HB8]
MVLAALVLVLEGEGLPEPLGLRGFFYGLLREVAPEVHDQGENPFALGFGGREGAAWARVSLLVEGLYARL
APRLYALEGEEVRLGPPFRVRAVLQEGHPWAGVSTYPRLFQGPPSRDLALRFASPTFFRRKGVHYPVPEP
RIVLESLLRRLEAFGPLKAPEGVREALLERTTVRSLEGRTLPARTEVDTAGFVGRVVYHLPRATEEEALW LSALGRFAFYSGVGAKTSLGYGRARAEFSA >gi|55978414|ref|YP_145470.1| hypothetical protein TTHB231 [Thermus thermophilus HB8]
MPQAVVLELVGEKPPLYPARYAHGLFFALLSRVSPELAQKLHEAPRKPFTLAPLPRAGPEGATIKGTLRL
RLTTLDDGLFAPFLRALLEAAPDGLPLGDSSYRLARVLATREGHPLAGATSWEELKEAPKREKATFRFLT
PTVFATSKPGGRTRYTPLPDPRLIAGSLLDKWQAHSFPYNPKEEAALRELFELDLEVAGFRNLRFHRVQ
AGKGFFPGFTGEATLRLWSQSLEAQEALGRLHALAFFSGVGAKTPYGMGLAVPL

*RNA repeat 1*
GUUGCAAGGGAUUGAGCCCCGUAAGGGGAUUGCGAC

*RNA repeat 2*
GUUGCAAACCUCGUUAGCCUCGUAGAGGAUUGAAAC

```
        U   A
      G       A
      C   -   G
      C   -   G
      C   -   G
5' -AUUGAGC       GAU- 3'

U
      G       A
      C   -   G
      C   -   G
      U   -   A
      C   -   G
5' -CGUUAGC       GAU- 3'
```

FIG. 11A

Staphylococcus epidermidis RP62A

Repeat sequence:
GGAUCGAUACCCACCCGAAGAAAAGGGGACGAGAAC

Minimum RNA recognized by Cas6 (dash denotes base pairing):

```
        AGAA
      A    A
    A       A
   G         A
       C--G
       C--G
       C--G
5'-UACCCAC--GAC-3'
```

>gi|157865878|ref|YP_189998.1| hypothetical protein SERP2455 [Staphylococcus epidermidis RP62A]
MINKITVELDLPESIRFQYLGSVLHGVLMDYLSDDIADQLHEFAYSPLKQRIYHKNKKIIWEIVCMSDN
LFKEVVKLFSSKNSLLLKYYQTNIDIQSFQIEKINVQNMMNQLLQVEDLSRYVRLNIQTPMSFKYQNSYM
IFPDVKRFFRSIMIQFDAFFEEYRMYDKETLNFLEKNVNIVDYKLKSTRFNLEKVKIPSFTGEIVFKIKG PLPFLQLTHFLLKFGEFSSGSGIKTSLGMGKYSII

FIG. 11B

Mycobacterium tuberculosis H37Rv

Repeat sequence:
GUCGUCAGACCCAAAACCCCGAGAGGGGACGGAAAC

Minimum RNA recognized by Cas6 (dash denotes base pairing):

```
        A  G
     G     A
      C---G
      C---G
      C---G
5'-CCAAAAC  GAC-3'
```

>gi|1648896|emb|CAB03662.1| HYPOTHETICAL PROTEIN Rv2824c [Mycobacterium tuberculosis H37Rv]
MAARRGGIRRTDLLRRSGQPRGRHRASAAESGLTWISPTLILVGFSHRGDRRMTEHLSRLTLTLEVDAPL
ERARVATLGPHLHGVLMESIPADYVQTLHTVPVNPYSQYALARSTTSLEWKISTLTNEARQQIVGPINDA
AFAGFRLRASGIATQVTSRSLEQNPLSQFARIFYARPETRKFRVEFLTPTAFKQSGEYVFWPDPRLVFQS
LAQKYGAIVDGEEPDPGLIAEFGQSVRLSAFRVASAPFAVGAARVPGFTGSATFTVRGVDFFASYIAALL WFGEFSGGCGIKASMGMGAIRVQPLAPREKCVPKP

FIG. 11C

Streptococcus thermophilus LMG18311

Repeat sequence
GAUAUAAACCUAAUUACCUCGAGAGGGGACGGAAAC

Minimum RNA recognized by Cas6 (dash denotes base pairing):

```
          A   G
         G A   A
          C-G
          U-G
          C-G
5'-UAAUUAC-GAC-3'
```

>gi|55820994|ref|YP_139436.1| hypothetical protein stu0959 [Streptococcus thermophilus LMG 18311]
MKKLVFTFKRIDHPAQDLAVKFHGFLMEQLDSDYVYLHQQQTNPYATKVIQGKENTQWVHLLTDDIED
KVFMTLLQIKEVSLNDLPKLSVEKVEIQELGADKLLEIFNSEENQTYFSIIFETPTGFKSQGSYVIFPSM
RLIFQSLMQKYGRLVENQPEIEEDTLDYLSEHSTITNYRLETSYFRVHRQRIPAFRGKLTFKVQGAQTLK AYVKMLLTFGEYSGLGMKTSLGMGIKLEERKD

FIG. 11D

Streptococcus sanguinis SK36

Repeat sequence
CCCCAGUCACCUCGGGAGGGGACGGAAAC

Minimum RNA recognized by Cas6 (dash denotes base pairing):

```
      G G
    G   A
    C-G
    C-G
    U-G
    C-G
5'-CAGUCAC   GAC-3'
```

>gi|125718072|ref|YP_001035205.1| hypothetical protein SSA_1252 [Streptococcus sanguinis SK36]
MKKIRLHLSKVSLKDDLVCKLQGFLMEKLSDDFASFLHQQETNPYSMNLRSEREESIWTVNLLSEEAEQ
QILPQLLSLEMIKLETYSEEILVKNIEIQSLSSQSLLEVFQGDEASHLISLNFYTPTTFKRQGQFVLFPD
TRLIFQSLMQKYSRLVEGKAEIEEETLEFLAEHSQISSYRLKSHYFPIHGRKYPAFEGRVTIRIQGASTL KAYAQMLLRFGEYSGVGAKCSLGMGGMRLEERKT

FIG. 11E

Microcystis aeruginosa NIES-843

Repeat sequence
GUUCCAAUUAAUCUUAAACCCUAUUAGGGAUUGAAAC

Minimum RNA recognized by Cas6 (dash denotes base pairing):

```
          U
       A     U
       U - A
       C - G
       C - G
5'-CUUAAAC-GAU-3'
```

>gi|166365825|ref|YP_001658098.1| CRISPR-associated Cas5e family protein [Microcystis aeruginosa NIES-843]
MPYSLVLNLTPRSPIYPNFLTGRHLHALFLTLVSSVDQELGKILTAEADKAFTLSPLQMQSGGKTINSP
QWRYERPIAPETPCWWRISLLDDRLFGKLTPLWLNLNPKHPWHLGSADLVITSVLATPQSVQPWANSCTY
QYLYENASETNREFDFLFATPVTFRQGKFDSALPTRELVFNSLLNRWNRYSAIPFDSIVLESIFPSFFDI
QTKLADEAYKNQSFGCVGEIHYRLLGEVEPAKIKAINVLADFALYAGVGRKTTMGMGMTRRIAKEKR

FIG. 11F

A: IYP_143344.1/TTHA078_Thermus_thermophilus_HB8/1-239
B: IYP_145470.1/TTHB231_Thermus_thermophilus_HB8/1-264
C: ICAB03662.1/Mycobacterium_tuberculosis_H37Rv/1-314
D: IYP_189998.1/Staphylococcus_epidermidis_RP62A/1-244
E: IYP_139436.1/Streptococcus_thermophilus_LMG_18311/1-243
F: IYP_001035205.1/Streptococcus_sanguinis_SK36/1-244
G: IYP_001658098.1/Microcystis_aeruginosa_NIES-843/1-277

```
A   1 ------------------------------------------------------------MVLAALVLVLEGEG  14
B   1 ------------------------------------------------------MPQAVVLELVGEK  13
C   1 MAARRGGIRRTDLLRRSGQPRGRHRASAAESGLTWISPTLILVGFSHRGDRRMTEHLSRLTETLEVDA  68
D   1 ------------------------------------------------------MINKITVEL---D  10
E   1 ------------------------------------------------------MKKLVFTFKRID  12
F   1 ------------------------------------------------------MKKIRLHLSKVS  12
G   1 ------------------------------------------------------MPYSLVLNLTPRS  13

A  15 LP-------EPLGERGFFYGLLREVAPE----VIDQ-GENPFALG---FGGREGAA------------  55
B  14 PPL-----YPARYAHGLFFALLSRVSPELAQKLHEA-PRKPFTLAELPRAGPEGAT------------  63
C  69 PLERARVATLGPHLHGV---LMESIPADYVQTLHTV-PVNPYSQYALARSTTSLE------------- 119
D  11 LPESIRFQYLGSVLHGV---LMDYLSDDIADQLHHEFAYSPLKQRI--YHKNKKII------------  61
E  13 HPAQD----LAVKFHGF---LMEQLDSDYVDYLHQQ-QTNPYATKV--IQGKENTQ------------  58
F  13 LKDDD----LVCKLQGF---LMEKLSDDFASFLHQQ-ETNPYSMNL--RSEREEST------------  58
G  14 PIYPN--FLTGRHEHAIFLTLVSSVDQELGKILHTAEADKAFTLSPLQMQSGGKTINSPQWRYERPIA  79

A  56 ------WA-----RVSLLVEGLYARLAPRLYALEGEE-VRLG-PPFRVRAVL--QE-GHPWAGVSTYP 107
B  64 ------LKGTLRLRLTTLDDGLFAPFLRALLEAAPDG-LPLGDSSYRLARVLATRE-GHPLAGATSWE 123
C 120 ------WK------ISTLTNEARQQIVGPINDAAFAG-FRLRASGIATQVTSRSLE-QNPL---SQFA 170
D  62 ------WE------IVCMSDNLFKEVVKLFSSKNS----LLIKYYQTNIDIQSFQ-IEKINVQNMMN 111
E  59 ------WV------VHLLTDDIEDKVFMTLLQIKE----VSLNDLP-KLSVEKVE-IQEL-GADKLL 106
F  59 ------WT------VNLLSEEAEQQILPQLLSLEM----IKLETYSEEILVKNIE-IQSL-SSQSLL 107
G  80 PETPCWWR------ISLLDDRLFGKLTPLWLNLNPKHPWHLGSADLVITSVLATPQSVQPWANSCTYQ 141

A 108 RLFQ-G-PPSRDLALRFASPTFFRR-----KGVH-YPVPEPRLVLESLLRRLEAFGPLKAPEGVREAL 167
B 124 ELKE-A-PKREKATFRFLTPTVFATSKPGGRTRY-TPIPDPRLIAGSLLDKWQAHSPFPYNPKEEAAL 188
C 171 RIFY-ARPETRKERVEFLTPTAFKQ-----SGEY-MFWPDPRLVFQSLAQKYGAI--VDGE-EDPGL 228
D 112 QLLQ-VEDLSRYVRLNIQTPMSFKY-----QNSY-MIFPDVKRFFRSIMIQFDAF--FEEYRMYDKET 170
E 107 EIFN-SEENQTYESI-IFETPTGFKS-----QGSY-VLFPSMRLIFQSLMQKYGRL--VENQPEIEEDT 165
F 108 EVFQ-GDEASHLISLNFYTPTTFKR-----QGQF-VLFPDTRLIFQSLMQKYSRL--VEGKAEIEEET 166
G 142 YLYENASETNREFDFLFATPVTFR-----QGKFDSALPTRELVENSLLNRWNRYSAIPFDSIVLESI 203

A 168 L--------ERTTVRSLEGRTLPARTEVDTAGFVGRVVYHLPRATEEEA-LWLSALGRFAFYSGVGAK 226
B 189 R-ELFELDLEVAGFRNLRFHRVQAG-KGFFPGFTGEATLRLWSQSLEAQ-EALGRLHALAFFSGVGAK 253
C 229 I-AEFGQSVRLSAFR-VASAPFAVG-AARVPGFTGSAITFTVRGVDTFAS-YIAALLWFGEFSGCGIK 291
D 171 L-NFLEKNVNIVDYK-IKSTRFNLE-KVKIPSFTGEIVFKIKGPLPFLQ--LTHFLLKFGEFSGSGIK 233
E 166 L-DYLSEHSTITNYR-LETSYFRVH-RQRIPAFRGKLTFKVQGAQTLKA--YVKMLLIFGEYSGLGMK 228
F 167 L-EFLAEHSQISSYR-LKSHYFPIH-GRKYPAFEGRVTIRIQGASTLKA--YAQMLLRFGEYSGVGAK 229
G 204 FPSFFDIQTKLADEA-YKNQSF-------GCVGEIHYRLGEVEPAKIKAINVLADFALYAGVGRK 261

A 227 TSLGYGRARAESA----------
B 254 TPYGMGLAVPL------------
C 292 ASMGMGAIRVQPLAPREKCVPKP
D 234 TSLGMGKYSII------------
E 229 TSLGMGGIKLEE-------RKD
F 230 CSLGMGGMRIEE-------RKT
G 262 TTMGMGMTRRIAK------EKR
```

```
YP_009170       MTHGAVKTYGIRLRVWGDYACFTRPEMKVERVSYDVMPPSAARGILEAIHWKPAIRWIVD  60
YP_961176       MTHGAVKTYGIRLRVWGDYACFTRPEMKVERVSYDVMPPSAARGILEAIHWKPAIRWIVD  60
YP_004513910    ------MAYGIKLHIWGDYACFTRPEMKVERVSYDVITPSAARGILEAIHWKPAIRWVID  54
YP_004294512    ------MAYGIKLHIWGDYACFTRPEMKVERVSYDVITPSAARGILDAIHWKPAIRWVID  54
ZP_05883174     ------MAYGIKLHVWGEYACFTRPEMKVERVSYDVITPSAARGILEAIHWKPAIWVID   54
YP_004496339    ------MGYGIKLKVWGDYACFSRPEMKVERVSYDVMTPSAARGILEAIHWKPAIRWVVD  54
                       * ::**::**:***:********.****:.*****:*****:******::*

YP_009170       RIHVLRPIVFDNVRRNEVS-SKIPKPNPATAMRDR--KPLYFLVDDGSNRQQRAATLLRN 117
YP_961176       RIHVLRPIVFDNVRRNEVS-SKIPKPNPATAMRDR--KPLYFLVDDGSNRQQRAATLLRN 117
YP_004513910    KIHVLQPVRFESIRRNEVG-SKISAAKIKTAMRNQSTQDLYLVADDAKERQQRASTVLRN 113
YP_004294512    KIHVLRPVRFESIRRNEVG-SKISANKIKTAMRNQSTQDLYLVADDSKERQQRASTVLRN 113
ZP_05883174     RIHVLKPVRFESIRRNELGNCKVSSAKVSGAMKRKSTQDLSFLIDDGNRQQRATTLLRD  114
YP_004496339    RIHILNAFKFENIRRNEVG-TKIPAGTVKTAMKGQ----PVMLCQYASNERQQRATLLKD 110
                :*::  ::*::****: .  *:. .   . **:.     .:   .   :***::: ::

YP_009170       VDYVIEAHFELTDKAGAEDNAGKHLDIFRRRARAGQSFQQPCLGCREFPASFELLEG--D 175
YP_961176       VDYVIEAHFELTDKAGAEDNAGKHLDIFRRRARAGQSFQQPCLGCREFPASFELLEG--D 175
YP_004513910    VAYIIEAHFELTDLATDEDNEGKHLDIFNRRARKGQCFQQPCMGVREFPAYFALIEPEQS 173
YP_004294512    VAYIIEAHFELTDLASEEDSEGKHLDIFNRRARKGQCFQQPCMGVREFPAYFSLIEPEES 173
ZP_05883174     VSYVIEAHFELSDKAGTEDSIGKHLDIFNRRARRGQYFHQPCLGNREFPAYFSLIEHEWD 174
YP_004496339    VAYYIEAHFEMTDKAGPTDTEEKHYNMFLRRARTGQCFHRPYLGCREFPAHFELLEG--E 168
                *.* *****:.* *. .:.  ** ::: ****.** *::* :* ****.*.*::* .

YP_009170       VPLSCYAGEK--RDLGYMLLDIDFERDMTPLFFKAVMEDGVITPPSRTSPEVRA 227
YP_961176       VPLSCYAGEK--RDLGYMLLDIDFERDMTPLFFKAVMEDGVITPPSRTSPEVRA 227
YP_004513910    LPESELTPEQLNRDLGWMLHDIDFANGMMPHFFKAELKGGIITVPDFYSEGVKA 227
YP_004294512    LPESELTLEQLNRDLGWMLHDIDFANEMMPRFFKAELKNGVITVPDFYSDEVKA 227
ZP_05883174     FPKSELATAS--KDLGWMLHDIDFANGAEPRFFRAELKDGMIDVPPFRSSKVV- 225
YP_004496339    NPISVHRGEK---DLGWMLLDIDYKNNMEPHFFRAVMQDGVTVPPLKGGGSL-  218
                 * *    .    ****:** **:.: :  :** *:::.*:  *   .   .
```

\>gi|46562260|ref|YP_009170.1| CRISPR-associated Csd1 family protein [Desulfovibrio vulgaris str. Hildenborough]
MTHGAVKTYGIRLRVWGDYACFTRPEMKVERVSYDVMPPSAARGILEAIHWKPAIRWIVDRIHVLRPIVF
DNVRRNEVSSKIPKPNPATAMRDRKPLYFLVDDGSNRQQRAATLRNVDYVIEAHFELTDKAGAEDNAGK
HLDIFRRRARAGQSFQQPCLGCREFPASFELLEGDVPLSCYAGEKRDLGYMLLDIDFERDMTPLFFKAVM EDGVITPPSRTSPEVRA

*CRISPR RNA repeat sequence:*
5'-GUCCGCCCCCACGCGGGGGGCGUGGAUUGAAAC-3'

*Predicted RNA secondary structure recognized by Cas5 (dash denotes base pairing):*

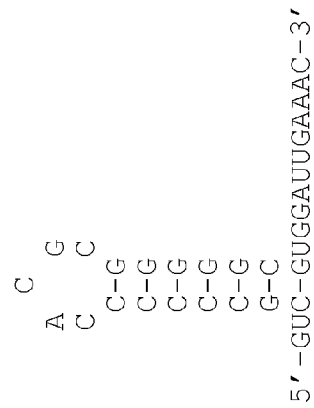

FIG. 16A

Neisseria mucosa ATCC 25996

>gi|261365836|ref|ZP_05978719.1| CRISPR-associated protein Cas5, Dvulg subtype [Neisseria mucosa ATCC 25996] MNQIRLHVWGDYACFTRPEMKVERVSYDVITPSAARGILAAVHWKPAIRWVIDRIYVLKPIRFESVRRNE LGGKISAGKVSGAMKRKSVADLYTLIEDDRQQRAATVLKDVAYVIEAHAVLTAKAGADETVTKHIEMFKR RAKKGQCFQQPCLGVREFPADFALIDEGEPLPPSALSESEANRDLGWMLHDIDFDHGNTPHFFRAQMKDG VIDVPPFYAEEVKA

*Predicted CRISPR RNA repeat consensus sequence:*
5'-CCAGCCGCCUUCGGGGGGCCUGUGUGUUGAAAC-3'

*Predicted RNA secondary structure recognized by Cas5 (dash denotes base pairing):*

```
      U   C
    U      G
      C - G
      C - G
      G - C
      C - G
      C - G
      G - C
      A - U
5'-CC-         -GUGUGUUGAAAC-3'
```

FIG. 16B

Bacillus halodurans C-125

>gi|15612900|ref|NP_241203.1| hypothetical protein BH0337 [Bacillus halodurans C-125]
MRNEVQFELFGDYALFTDPLTKIGGEKLSYSVPTYQALKGIAESIYWKPTIVFVIDELRVMKPIQMESKG
VRPIEYGGGNTLAHYTYLKDVHYQVKAHFEFNLHRPDLAFDRNEGKHYSILQRSLKAGGRRDIFLGAREC
QGYVAPCEFGSGDGFYDGQGKYHLGTMVHGFNYPDETGQHQLDVRLWSAVMENGYIQFPRPEDCPIVRPV
KEMEPKIFNPDNVQSAEQLLHDLGGE

*Predicted CRISPR RNA repeat consensus sequence:*
5'-GUCGCACUCUACAUGAGUGCGUGGAUUGAAAU-3'

*Predicted RNA secondary structure recognized by Cas5 (dash denotes base pairing):*

```
       C
    A     A
    U     U
    C  -  G
    U  -  A
    C  -  G
    A  -  U
    C  -  G
    G  -  C
5'-GUC   GUGGAUUGAAAU-3'
```

FIG. 16C

Bacillus cereus F65185

```
>gi|229073767|ref|ZP_04206866.1| CRISPR-associated protein Cas5 [Bacillus cereus F65185]
MKKEEESLRNSIEFEVFGDYALFTDPLMKMGGEKLTYQVPTYQAIKGIVESIYWKPTLLMIVDKIRIMNA
IKMESKGIRPIEYGGGNTLANYTYLKNVRYQVQAHFIFNPHRPDLAFDRNEYKHHNILKRSLKVGGRRDI
FLGTRECQGYVEPCVFGEGEGFYDNYGGDIHLGTMVHGLNYPDETGRNELEVRLWNPVMRDGIIQFIRPE
ECTKIRKISKMEPKIFDSSNVESVDELIKQLEEGGE
```

*Predicted CRISPR RNA repeat consensus sequence:*

5′-UGUCGCACCUUAUAUAGGUGCGUGGAUUGAAAU-3′

*Predicted RNA secondary structure recognized by Cas5 (dash denotes base pairing):*

```
       U
     A   A
     U   U
      U-A
      C-G
      C-G
      A-U
      C-G
      G-C
5′-UGUC-GUGGAUUGAAAU-3′
```

FIG. 16D

Selenomonas noxia ATCC 43541

>gi|292670207|ref|ZP_06603633.1| CRISPR-associated Cas5 family protein [Selenomonas noxia ATCC 43541] MRNSIEFQVYGRMALFTDPITKIGGEKASYSVPTYQALKGITESIYWKPTIWFIDEVRVMKRITTQVRG VKPLKYGDSGNDLSYYKYLSDVCYQVRAHFEFNMHREELKEDRDEHKLHNIAKRMVERGGRRDIFLGTRE CQGYVEPVKYGVGKGYDNVDELPLGIMLHGFNYPDETGEDKLQVRFWKPTMKKGIIHFRRPEKCEMVRD IREVRTKQFDADNVFFAEEEKQLEGGHL

*Predicted CRISPR RNA repeat consensus sequence:*
5'-GUCGCGCCCCGCAUGGGGCGCGUGGAUUGAAA-3'

*Predicted RNA secondary structure recognized by Cas5 (dash denotes base pairing):*

```
      C   A
   G    U
     C-G
     C-G
     C-G
     C-G
     G-C
     C-G
     G-C
5'-GUC-GUGGAUUGAAAC-3'
```

A
Repeat type 1 (R1)
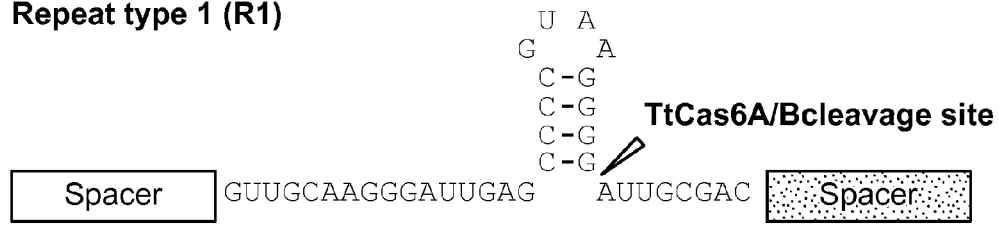
Repeat type 3 (R3)
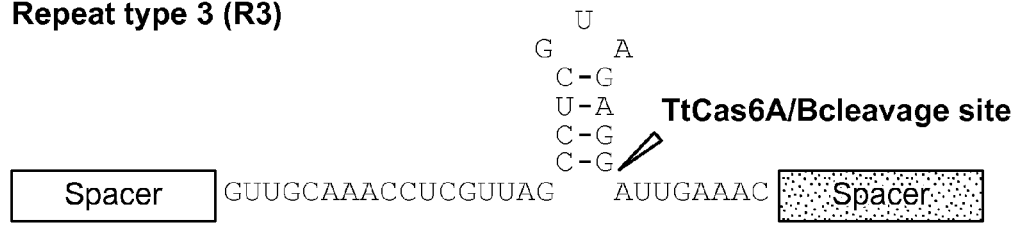
Repeat type 2 (R2)
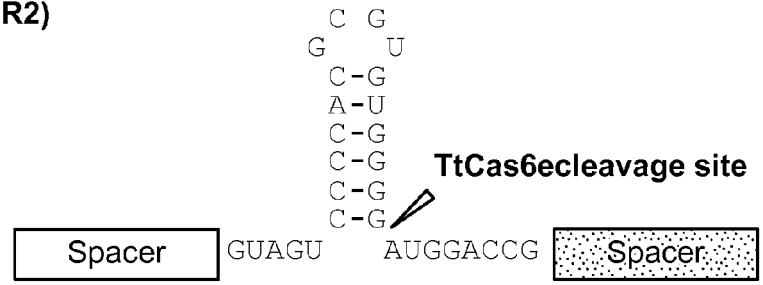
FIG. 22

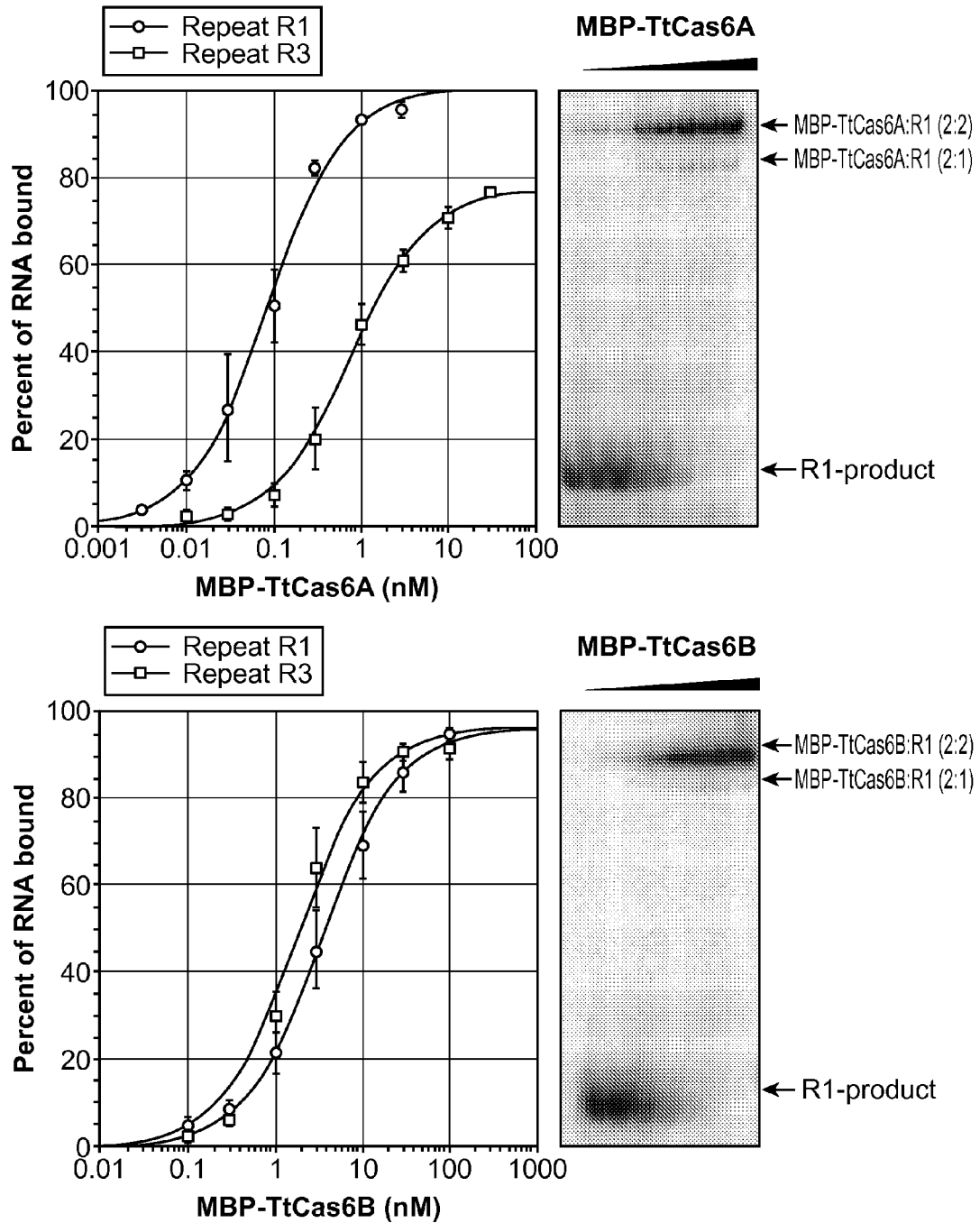
FIG. 22(Cont. 1)

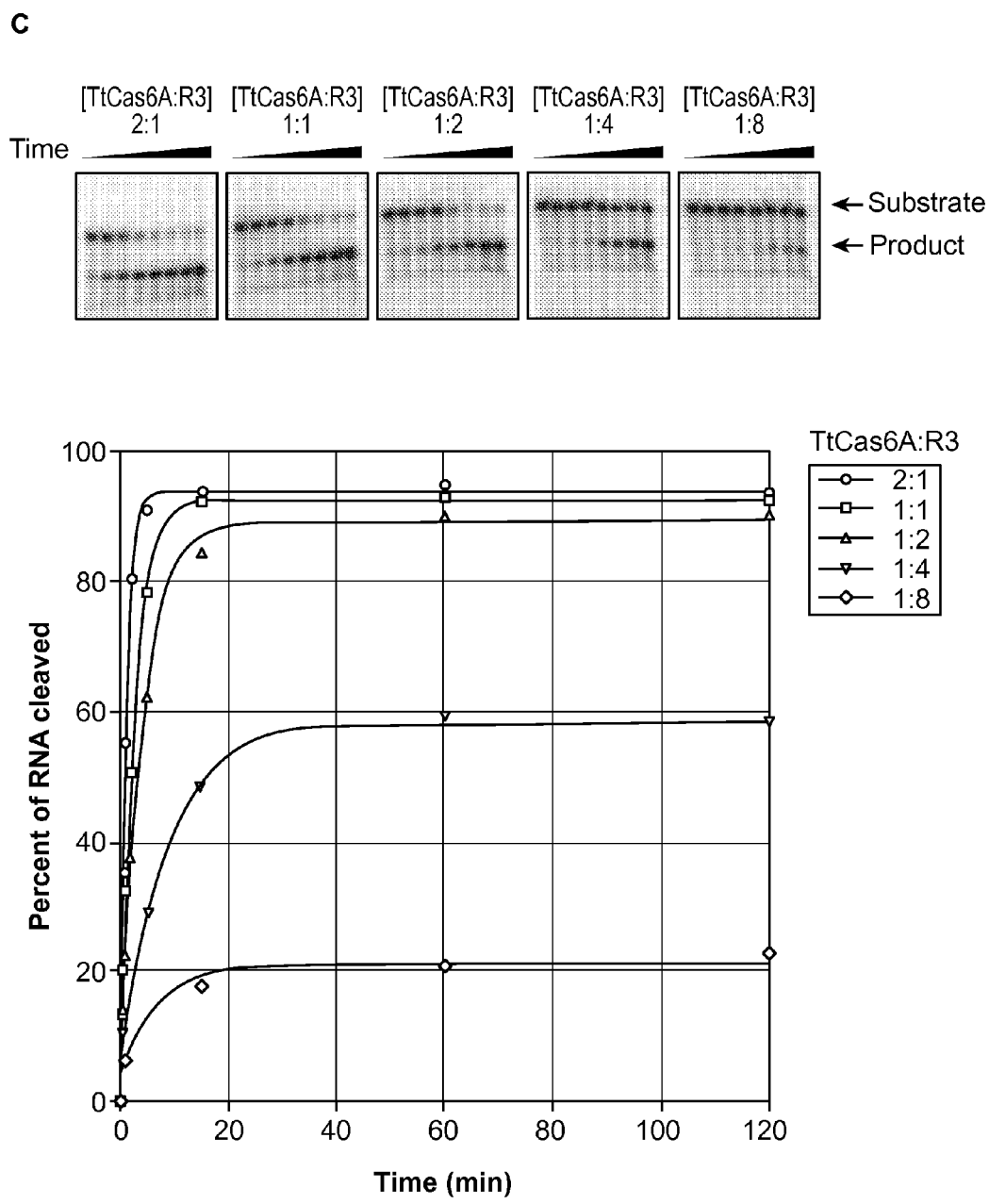
FIG. 22(Cont. 2)

C (Cont.)
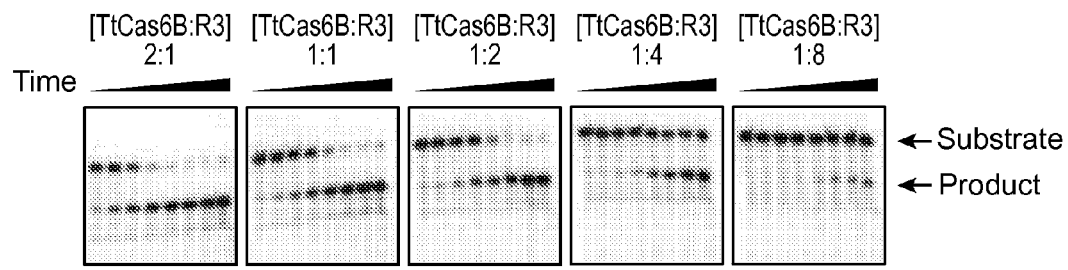
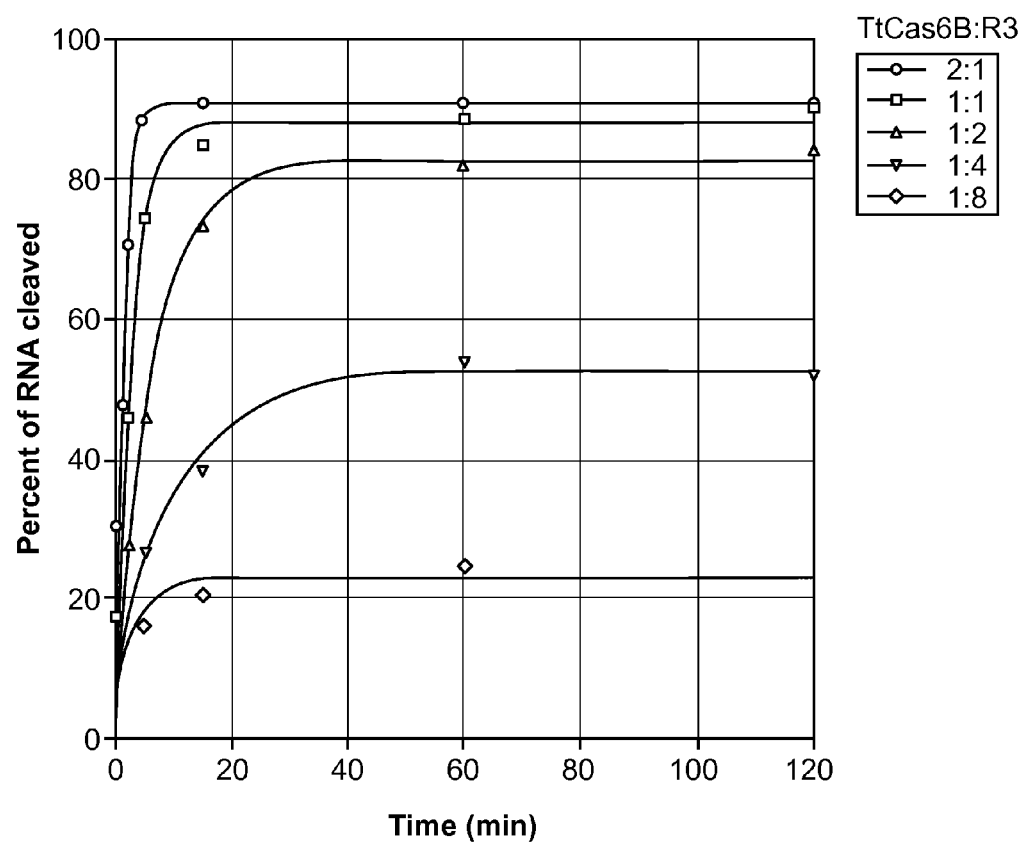
FIG. 22(Cont. 3)

A
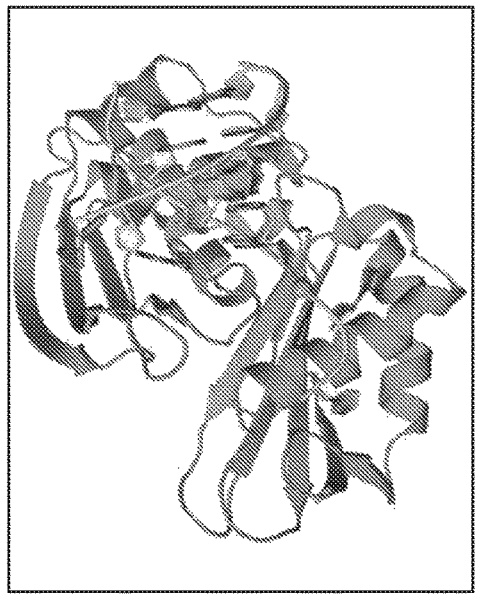
TtCas6A + repeat R1 RNA
substrate mimic
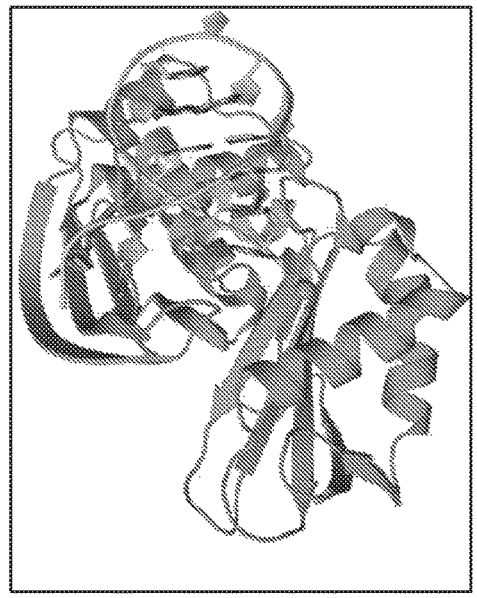
TtCas6A + repeat R1 RNA
product
TtCas6B + repeat R3 RNA
product
FIG. 23

B
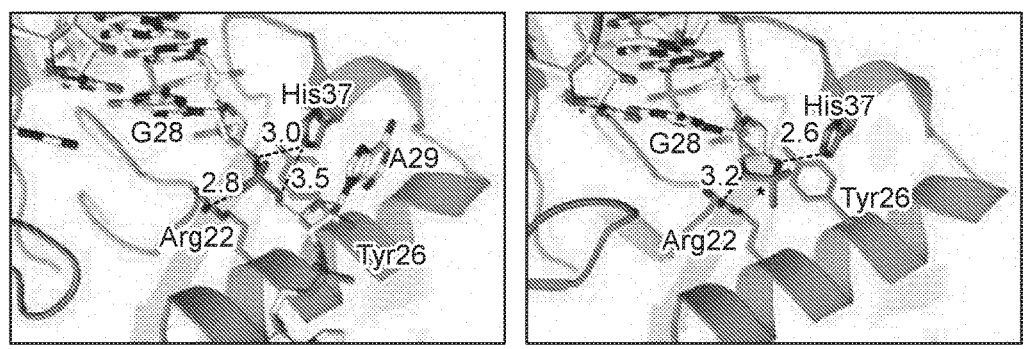
TtCas6A + repeat R1 RNA
Substrate mimic
TtCas6A + repeat R1 RNA
product
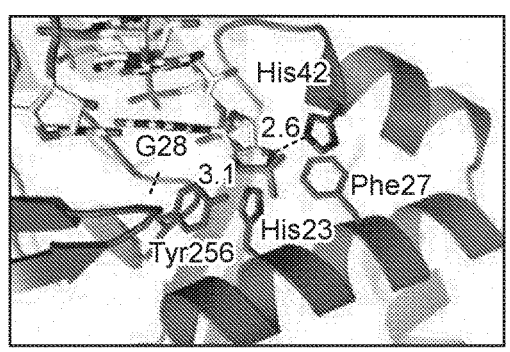
TtCas6B + repeat R3 RNA
product
FIG. 23(Cont. 1)

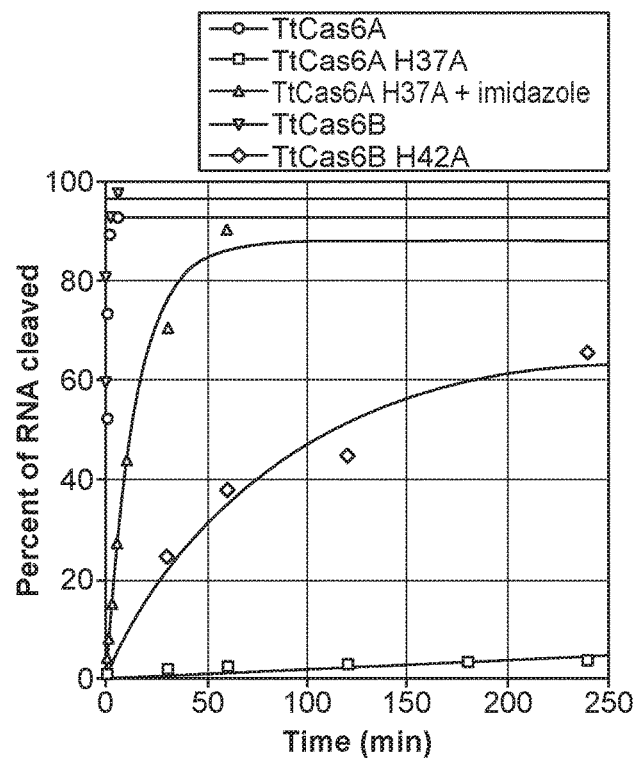
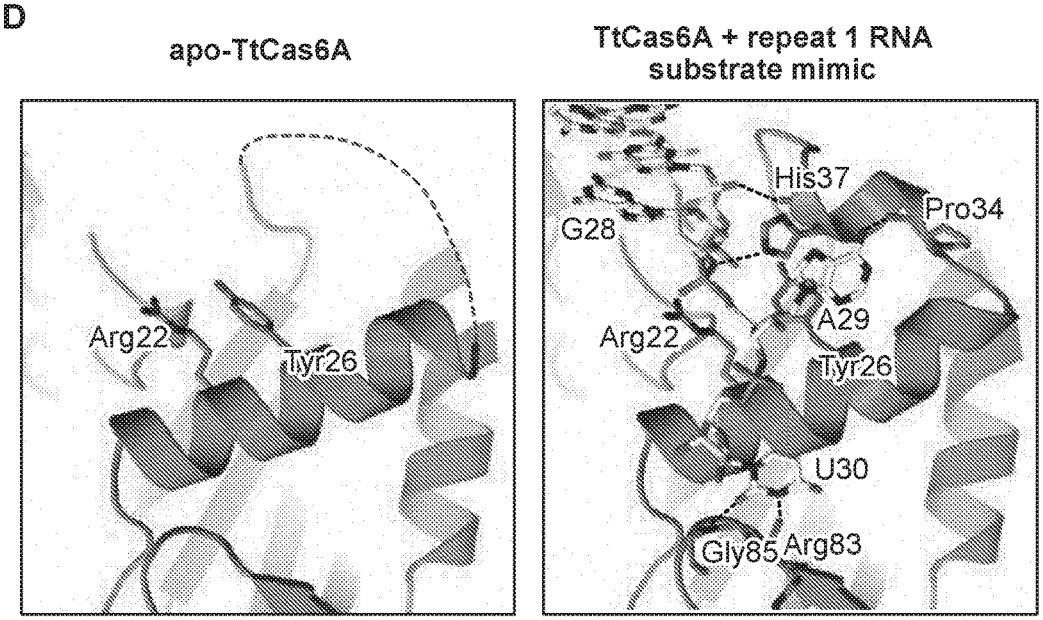
FIG. 23(Cont. 2)

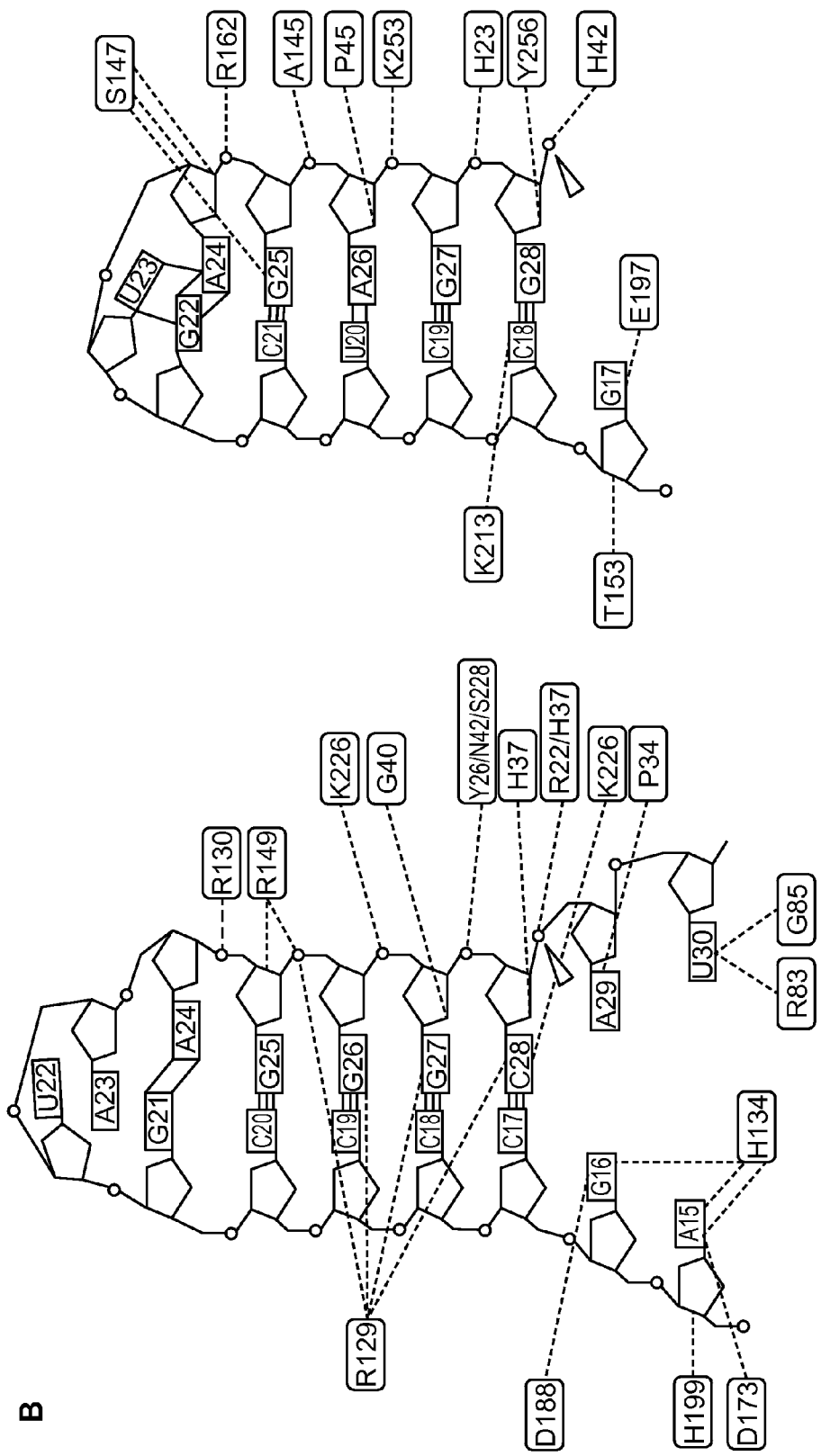
FIG. 24(Cont. 1)

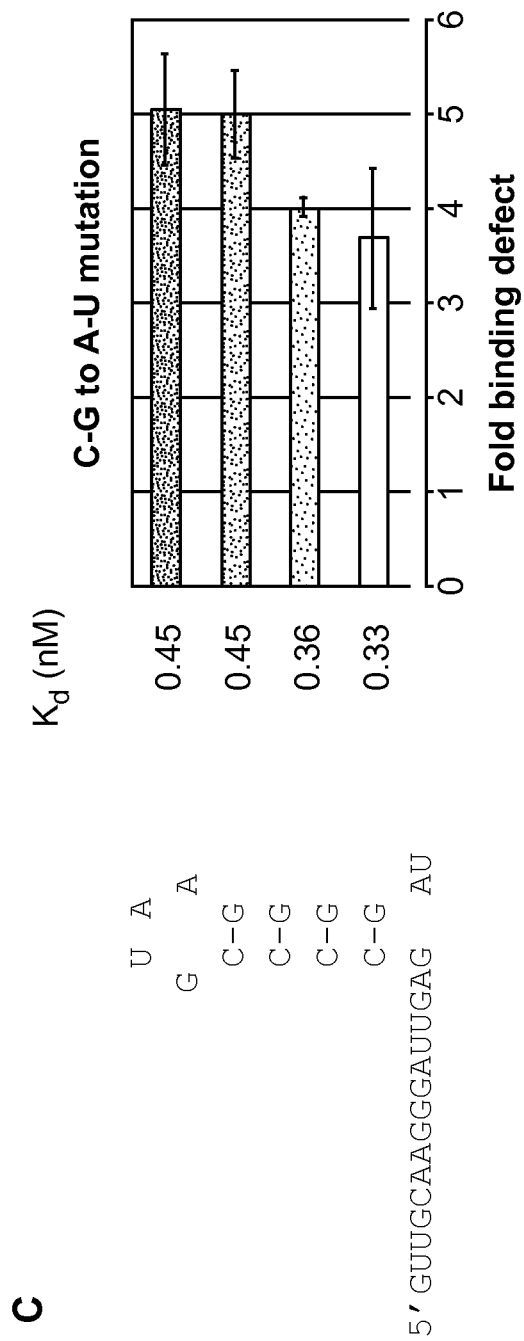
FIG. 24(Cont. 2)

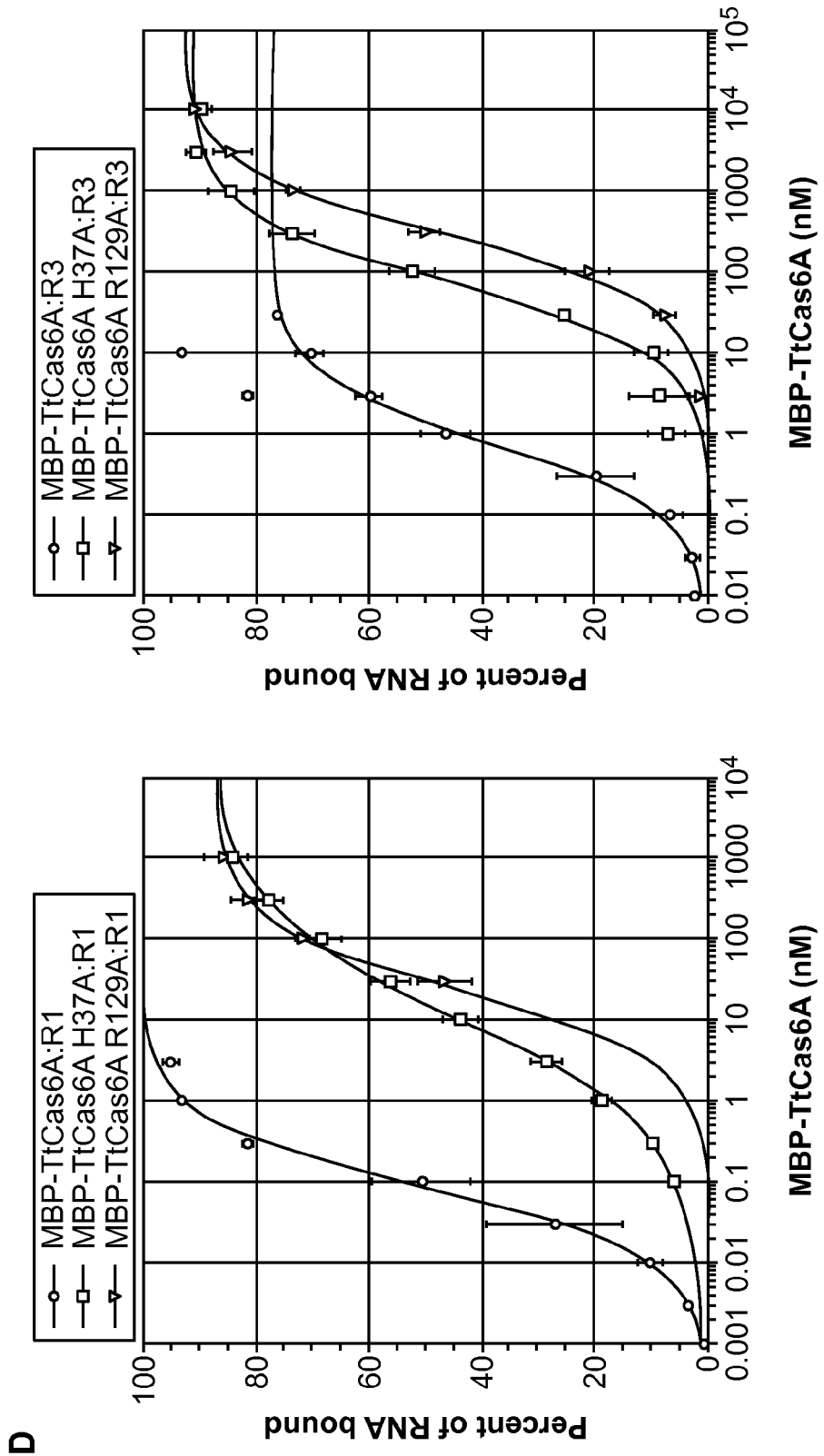
FIG. 24(Cont. 3)

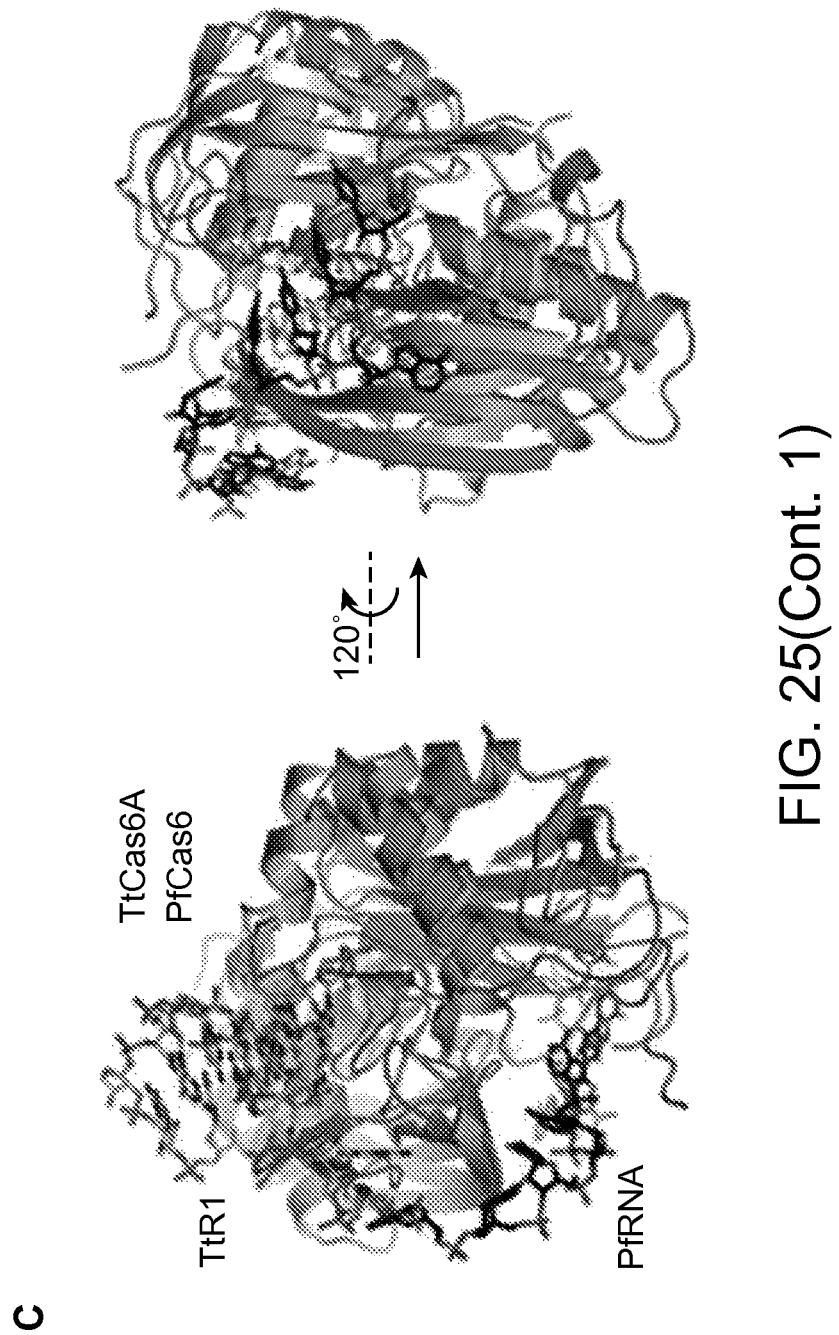
FIG. 25(Cont. 1)

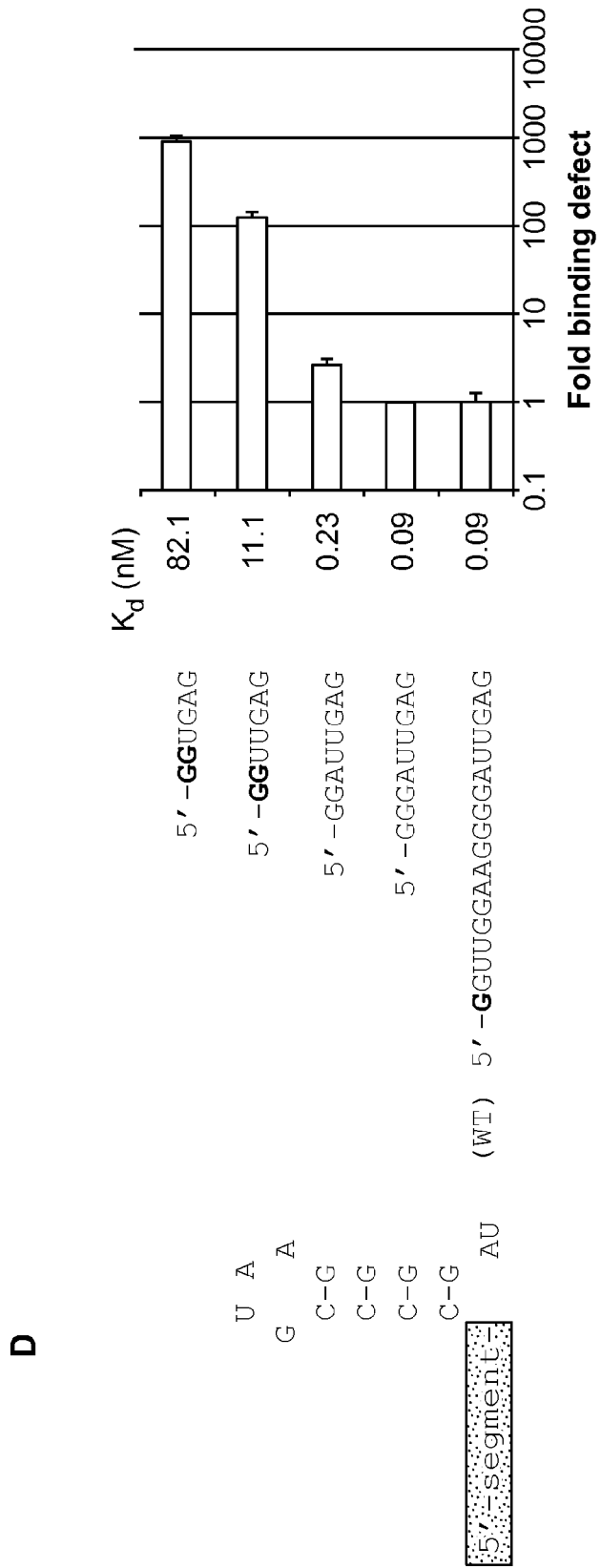
FIG. 25(Cont. 2)

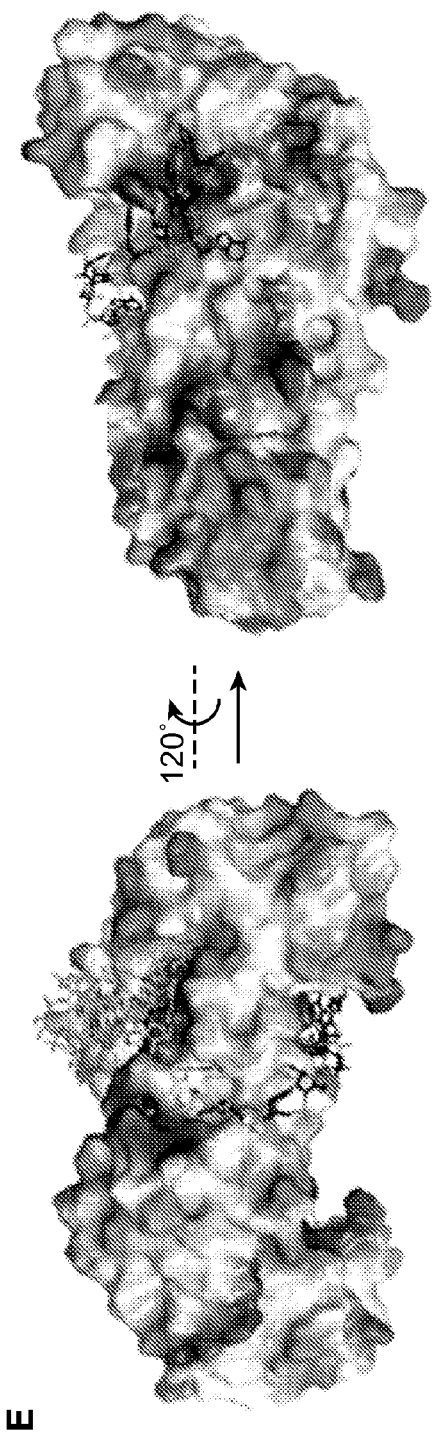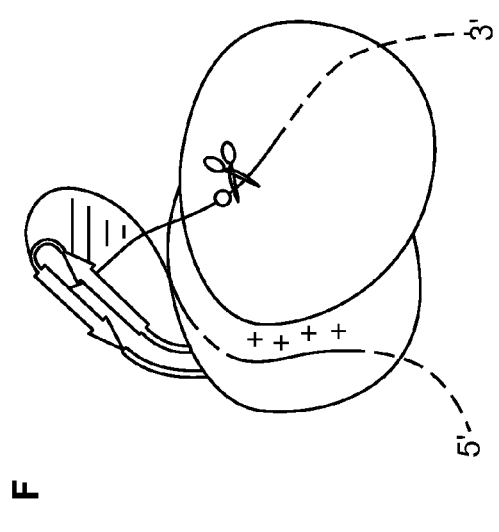
FIG. 25(Cont. 3)

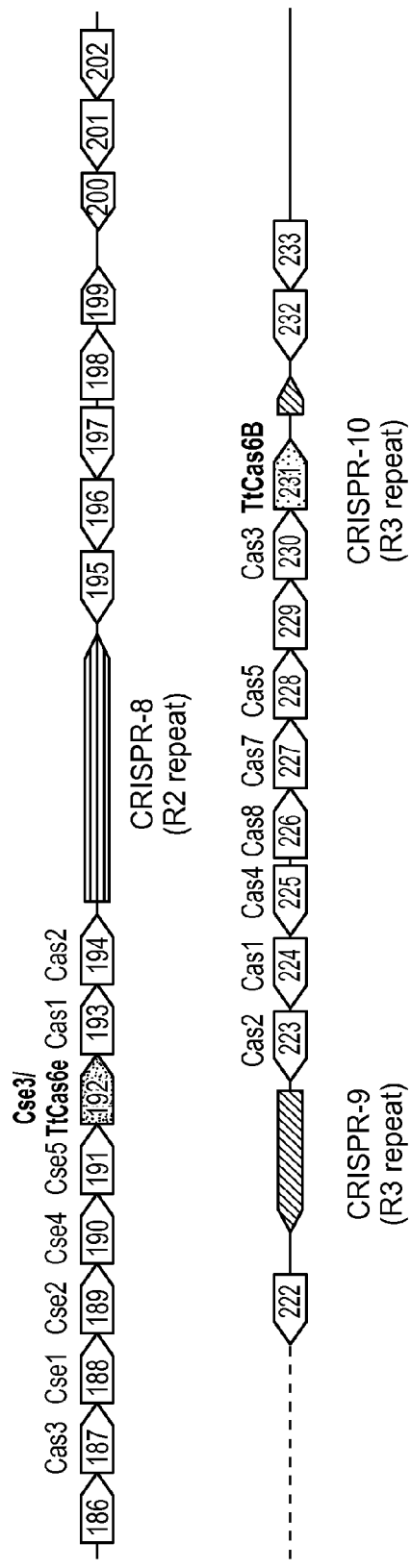
FIG. 26 (Cont. 1)

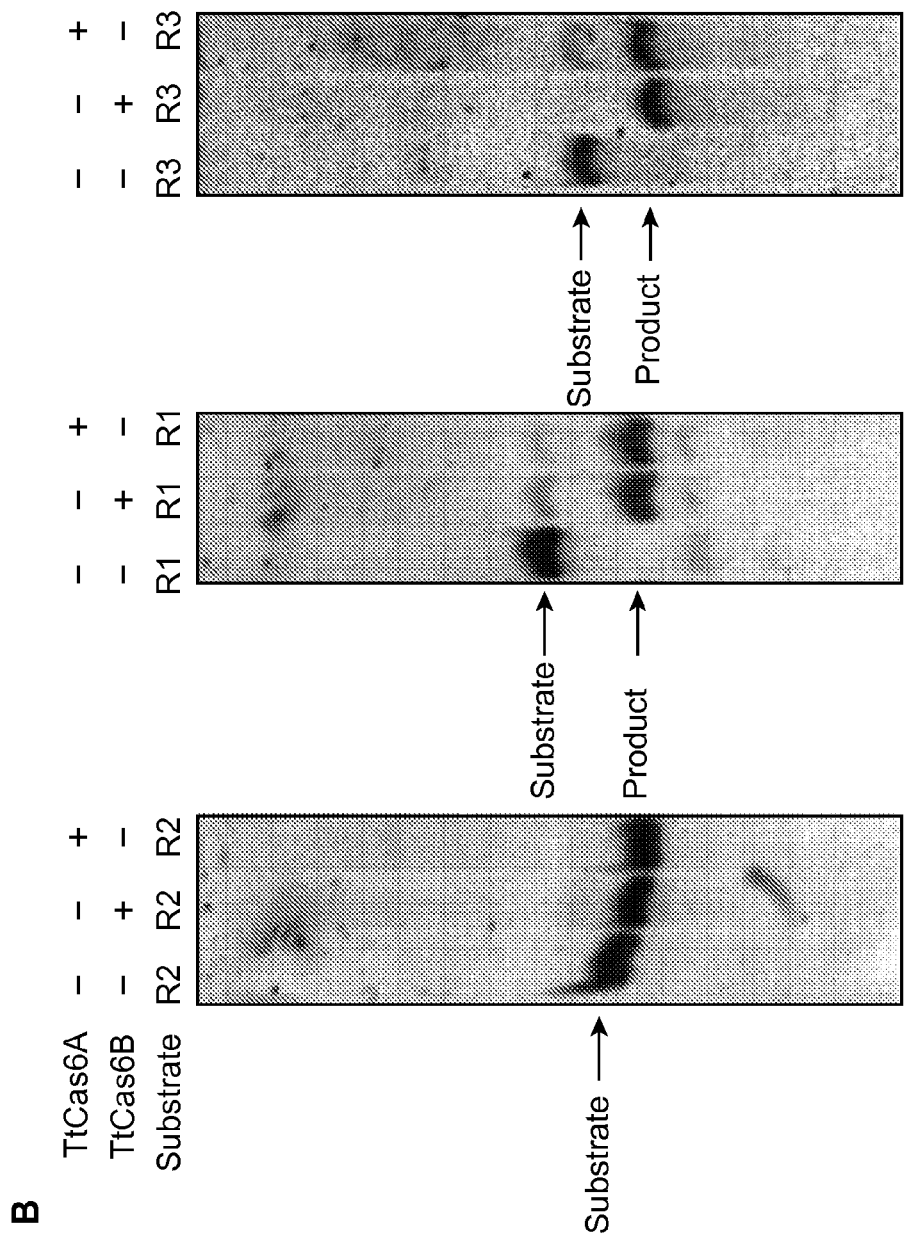
FIG. 26 (Cont. 2)

A TtCas6A + repeat R1 RNA substrate mimic
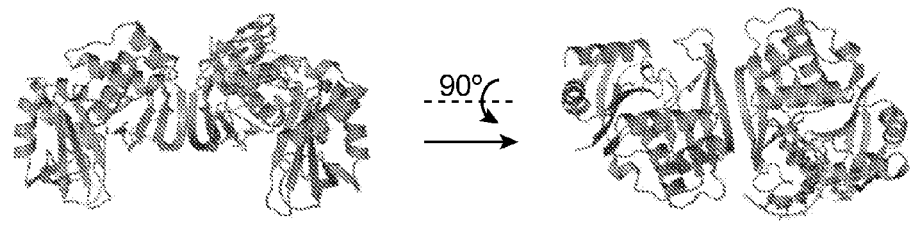
B TtCas6A + repeat R1 RNA product
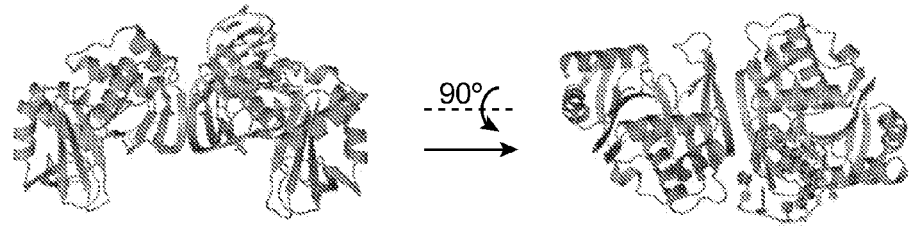
C TtCas6B + repeat R3 RNA product
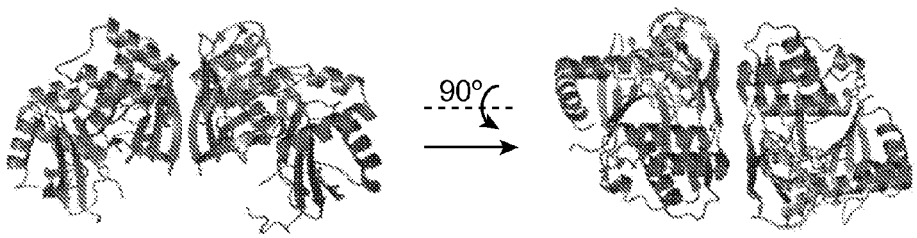
FIG. 27

A

TtCas6A/1-238

TtCas6A/1-238
TtCas6B/1-262
PfCas6_(PDB_3pkm)/1-229
TtCas6e_(PDB_2y8w)/1-215
PaCas6f_(PDB_2x1k)/1-188

TtCas6A/1-238

TtCas6A/1-238
TtCas6B/1-262
PfCas6_(PDB_3pkm)/1-229
TtCas6e_(PDB_2y8w)/1-215
PaCas6f_(PDB_2x1k)/1-188

TtCas6A/1-238

TtCas6A/1-238
TtCas6B/1-262
PfCas6_(PDB_3pkm)/1-229
TtCas6e_(PDB_2y8w)/1-215
PaCas6f_(PDB_2x1k)/1-188

TtCas6A/1-238

TtCas6A/1-238
TtCas6B/1-262
PfCas6_(PDB_3pkm)/1-229
TtCas6e_(PDB_2y8w)/1-215
PaCas6f_(PDB_2x1k)/1-188

TtCas6A/1-238

TtCas6A/1-238
TtCas6B/1-262
PfCas6_(PDB_3pkm)/1-229
TtCas6e_(PDB_2y8w)/1-215
PaCas6f_(PDB_2x1k)/1-188

FIG. 28

A active site loop

β1　　　　　　　　　　　α1　　　　　　η1　　　　β2

1　　　　10　　　　　20　　　　30　　　　　40

..MVL.AALVLVLE.GE...G..LP.E....PLGLRGFFYGL.LRE..VL.AP..EVHD.QGENPFALG.FG
...MP.QAVVLELV.GE...K..P..PLYPARYAHGLFFAL.L.SRVSPELAQKLHE.APRKPFTLA.PL
HHHHG.SRFLIRLVAFK...V..PYNH...QYYLQGLIYNA.I.KSSNPKLATYLHEVKGPKLFTYSLFM
GTGAM.WLTKLVLNPASRAARRDL..AN...PYEMHRTLSKAVS.RALE.EGR........ERLLWR.LE
...TMDHYLDIRLR.PDP.EFP.PAQL...MCVLFGKLHQA.LVA..Q.GG.........DRIGVS.FP

β3　　　　α2　　　　　β4　　　β5

T........T　　　　　　　　　　　　　　　　　　　　T..T
50　　　　　60　　　　70　　　　80　　　　90　　　　100

GRE.........GAAWARVSLL..VEGLYARLAPRLYAL..EGEEVRLG.PPFRVR.AVL.QE.GHP..W
PGPEGA...TLKGTLRLRLTTL..DDGLFAPFLRALLEA..APDGLPLGDSSYRLA.RVL.AT.REGHPL
AEKREHPYFLGYKKGFFYESTC..VPEIAEALVNGLLMN..P..EVRLWDERFYLH.EIK.VL.R.....
PARG.......LEPPVVLVQTL..T...EPDW.....SVLDE..GY......A..Q.V.FPPKPF.....
DLDESR....SRLGERLRIHASADD...LRALL...ARPW.LE.GLR....DHL.QFGEP.AVVP.....

major groove binding

β6　η2　　　β7　　　β8　　β9　　　　α3

→　ℓℓℓℓ　　→　　　→　　→　　　ℓℓℓℓℓℓℓℓℓℓℓℓℓ
　　　110　　　120　　　130　　　　140　　　　150

AGVSTYPRLFQGPPSRDLA..LREASPT..FFRR.....KGVHYPVPEPRLVIESLLRRLEAFGPL....
AGATSWEELKEAPKREKAT..FRFLTPT..VFATSK.PGGRTRYTPLPDPRLIAGSLLDKWQAHSPFPYN
.EPKK..........FNGSTFVTLSPL..AVTV.....VYDVPPMEKEFYSILKDDLQDKY........
.HPALK........PGQRLR.F.RL.RAN.P.AKRLAATGKRVALKTPAEKVAWLERRLE.........
.HP............TP..Y.RQ..VSRV.QA.....KSNPERLRRRLMRRHDLS.............

α4　　β10　　　　　　　　　　　　　　β11

T..........T　　　　　　TT
160　　170　　180　　　　　　　　190　　　200

.KAPEGVREALLERTTVRSLEGRTLP.AR.............TEVDTAGFVGRVVYHLPRATEEE.A
PKEEAALRELFELDLEVAGERNLRFHRVQ.............AGKGFFPGFTGEATLRLWSQSLEAQ
....VMAYGDKPPSEFEMEVLIAKPKRFR.............IKPGIYQTAWHLVFRAYGN......
......EGGFRLLEGERGPWVQILQDTFLEVRRKKDGEEAGKLLQVQAVLFEGRLEVVDPE........
........EEEARKRIPDTVARALDLPFVTLRSQS...TGQHFRL................

α5　　η3　　β12

210　　220　　230

LWLSALGRFAFYSGVGAKTSLGYGR.ARAES.....................
EALGRLHALAFFSGVGAKTPYGMGL.AVPL......................
...DDLLKVGYEVGFGEKNSLGFGM.VKVEG.....................
.....RALATLRRGVPGKALGLGLLSVAP.......................
.................FIRHGPLQVTAEEGGFTCYGLSKGGFVPWF

FIG. 28(Cont.1)

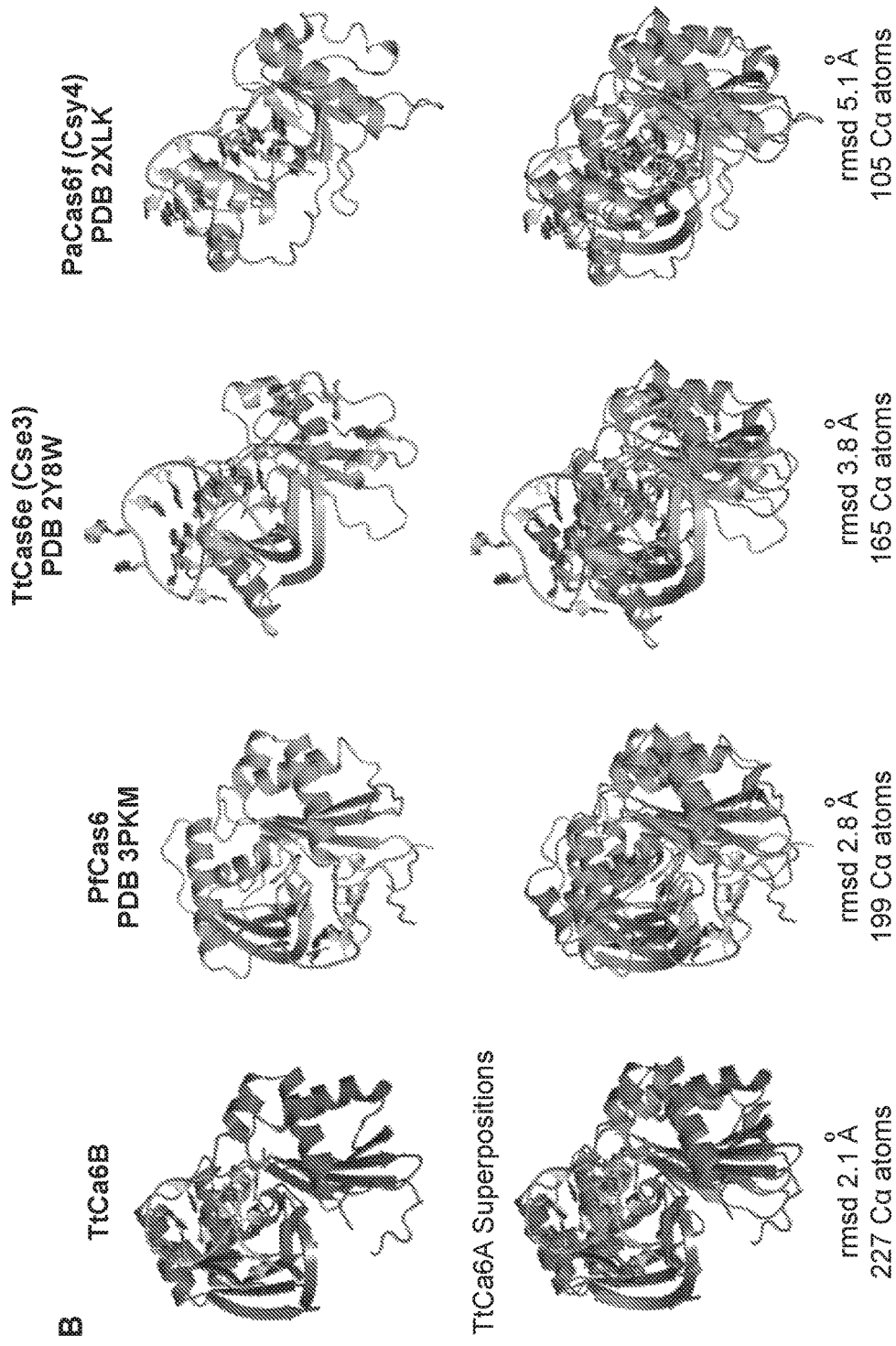
FIG. 28 (Cont. 2)

| Protein | TTHB231 | TTHB231 | TTHB231 | TTHB231 |
|---|---|---|---|---|
| RNA | - | - | - | - |
| Data collection | Native | Zn peak | Zn inflection | Zn remote |
| X-ray source | ALS 8.2.2 | ALS 8.2.2 | ALS 8.2.2 | ALS 8.2.2 |
| Space group | $P4_22_12$ | $P4_22_12$ | $P4_22_12$ | $P4_22_12$ |
| Cell dimensions | | | | |
| $a, b, c$ (Å) | 68.5, 68.5, 133.7 | 68.5, 68.5, 133.7 | 68.5, 68.5, 133.7 | 68.5, 68.5, 133.7 |
| $\alpha, \beta, \gamma$ (°) | 90.0, 90.0, 90.0 | 90.0, 90.0, 90.0 | 90.0, 90.0, 90.0 | 90.0, 90.0, 90.0 |
| Wavelength (Å) | 0.999951 | 1.2822 | 1.2828 | 1.2769 |
| Resolution (Å)* | 61.0-2.0 (2.05-2.00) | 61.0-2.1 (2.15-2.10) | 61.0-2.1 (2.15-2.10) | 61.0-2.1 (2.15-2.10) |
| $R_{sym}$ (%)* | 6.8 (59.1) | 6.1 (60.7) | 6.3 (64.4) | 6.5 (69.5) |
| $I/\sigma I$* | 22.4 (3.6) | 18.4 (2.4) | 17.7 (2.3) | 18.1 (2.3) |
| Completeness (%)* | 99.8 (96.8) | 99.7 (96.0) | 99.7 (96.7) | 99.8 (97.8) |
| Redundancy | 9.3 (8.5) | 5.0 (4.5) | 5.0 (4.5) | 5.0 (4.7) |
| Refinement | | | | |
| Resolution (Å) | 48.5-2.0 | | | |
| No. reflection | 22224 | | | |
| $R_{work} / R_{free}$ | 0.211 / 0.239 | | | |
| No. atoms | | | | |
| Protein | | | | |
| Nucleic Acid | | | | |
| Ion | | | | |
| Water | | | | |
| B-factors | | | | |
| mean | 43.5 | | | |
| Protein | | | | |
| Nucleic Acid | - | | | |
| Ion | | | | |
| Water | | | | |
| R.m.s. deviations | | | | |
| Bond lengths (Å) | 0.008 | | | |
| Bond angles (°) | 1.02 | | | |
| Ramachandran plot | | | | |
| % favoured | 97.4 | | | |
| % allowed | 2.6 | | | |
| % outliers | 0.0 | | | |
| Molprobity | | | | |
| Clashscore | 15.6 | | | |
| * Values in parentheses denote highest resolution shell | | | | |

FIG. 30

| TTHA0078 | TTHA0078-H37A | TTH0078 | TTHB231 |
|---|---|---|---|
| R1 substrate mimic | - | R1 product | R3 product |
| | | | |
| ALS 8.2.2 | ALS 8.2.2 | ALS 8.2.1 | ALS 8.2.1 |
| $P2_1$ | $P4_22_12$ | $P2_1$ | $P4_32_12$ |
| | | | |
| 43.1, 83.3, 73.4 | 149.7, 149.7, 155.1 | 43.7, 83.1, 72.4 | 75.2, 75.2, 308.8 |
| 90.0, 101.4, 90.0 | 90.0, 90.0, 90.0 | 90.0, 100.6, 90.0 | 90.0, 90.0, 90.0 |
| 0.999951 | 0.979023 | 0.99992 | 0.99994 |
| 72.0-1.80 (1.90-1.80) | 58.40-1.70 (1.74-1.70) | 54.0-2.5 (2.57-2.50) | 73.08-3.00 (3.08-3.00) |
| 6.0 (69.7) | 7.8 (72.7) | 9.8 (52.0) | 13.1 (78.5) |
| 15.5 (1.9) | 13.4 (2.0) | 13.9 (2.5) | 16.6 (2.8) |
| 98.8 (97.8) | 98. 3(99.7) | 99.8 (98.3) | 99.9 (99.9) |
| 3.7 (3.6) | 4.9 (4.8) | 3.8 (3.6) | 7.7 (8.1) |
| | | | |
| 72.0-1.8 | 58.4-1.7 | 54.0-2.50 | 73.0-3.00 |
| 46543 | 56542 | 17611 | 18676 |
| 0.194 / 0.224 | 0.185 / 0.203 | 0.202 / 0.245 | 0.249 / 0.299 |
| | 7988 | | |
| | 64 | | |
| | 1 | | |
| | 5 | | |
| 35.0 | 24.0 | 35.7 | 58.8 |
| | - | | |
| | | | |
| 0.005 | 0.005 | 0.006 | 0.004 |
| 0.93 | 0.16 | 1.01 | 0.94 |
| | | | |
| 97.0 | 97.8 | 97.6 | 96.9 |
| 2.2 | 2.2 | 2.3 | 3.1 |
| 0.0 | 0.0 | 0.0 | 0.0 |
| | | | |
| 11.9 | 15.3 | 14.2 | |

FIG. 30(Cont.)

ENDORIBONUCLEASE AND METHODS OF USE THEREOF

CROSS-REFERENCE

This application claims the benefit of U.S. Provisional Patent Application No. 61/660,414, filed Jun. 15, 2012, which application is incorporated herein by reference in its entirety.

STATEMENT REGARDING FEDERALLY SPONSORED RESEARCH

This invention was made with government support under Grant No. GM007232 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-190WO-SeqList_ST25.txt" created on Jun. 3, 2013 and having a size of 65 KB. The contents of the text file are incorporated by reference herein in their entirety.

BACKGROUND

Bacteria and archaea possess adaptive immune systems that rely on small RNAs for defense against invasive genetic elements. CRISPR (clustered regularly interspaced short palindromic repeats) genomic loci are transcribed as long precursor RNAs, which must be enzymatically cleaved to generate mature CRISPR-derived RNAs (crRNAs) that serve as guides for foreign nucleic acid targeting and degradation. This processing occurs within the repetitive sequence and is catalyzed by a dedicated CRISPR-associated (Cas) family member in many CRISPR systems.

Endoribonucleases that process CRISPR transcripts are bacterial or archaeal enzymes capable of catalyzing sequence- and structure-specific cleavage of a single-stranded RNA. These enzymes cleave a specific phosphodiester bond within a specific RNA sequence.

SUMMARY

The present disclosure provides variant Cas endoribonucleases, nucleic acids encoding the variant Cas endoribonucleases, and host cells genetically modified with the nucleic acids. The variant Cas endoribonucleases find use in a variety of applications, which are also provided. The present disclosure also provides methods of detecting a specific sequence in a target polyribonucleotide; and methods of regulating production of a target RNA in a eukaryotic cell.

BRIEF DESCRIPTION OF THE DRAWINGS

FIG. 6A shows the data for TTHB231 with Tt_Repeat2 substrate; FIG. 6B shows the data for TTHA0078 with Tt_Repeat 1 substrate.

FIGS. 9A and 9B depict an alignment of Cas6 amino acid sequences. (Top to bottom, SEQ ID NOs: 16-23).

FIG. 10 depicts an alignment of Cas6 amino acid sequences. (Top to bottom, SEQ ID NOs: 24-27).

FIGS. 11A-F depict Cas6 amino acid sequences and RNA sequences and structures recognized by the Cas6 polypeptides. (Top to bottom: FIG. 11A, SEQ ID NOs: 19, 24, 1, 2, 28, 29; FIG. 11B, SEQ ID NOs: 3, 30, 31; FIG. 11C, SEQ ID NOs: 4, 32, 33; FIG. 11D, SEQ ID NOs: 5, 34, 35; FIG. 11E, SEQ ID NOs: 6, 36, 37; FIG. 11F, SEQ ID NOs: 7, 38, 39).

FIG. 12 provides an amino acid sequence alignment of the Cas6 amino acid sequences depicted in FIGS. 11A-F. (Top to bottom, SEQ ID NOs: 19, 24, 33, 31, 35, 37, 39).

(FIG. 14B: SEQ ID NO: 40).

FIG. 15 provides an amino acid sequence alignment of Cas5 polypeptides. (Top to bottom, SEQ ID NOs: 13, 41, 42, 43, 44, 45).

FIGS. 16A-E depict Cas5 amino acid sequences and RNA sequences and structures recognized by the Cas5 polypeptides. (Top to bottom: FIG. 16A, SEQ ID NOs: 13, 8, 8; FIG. 16B, SEQ ID NOs: 46, 9, 9; FIG. 16C, SEQ ID NOs: 47, 10, 10; FIG. 16D, SEQ ID NOs: 48, 11, 11; FIG. 16E, SEQ ID NOs: 49, 12, 50).

Figure 17:
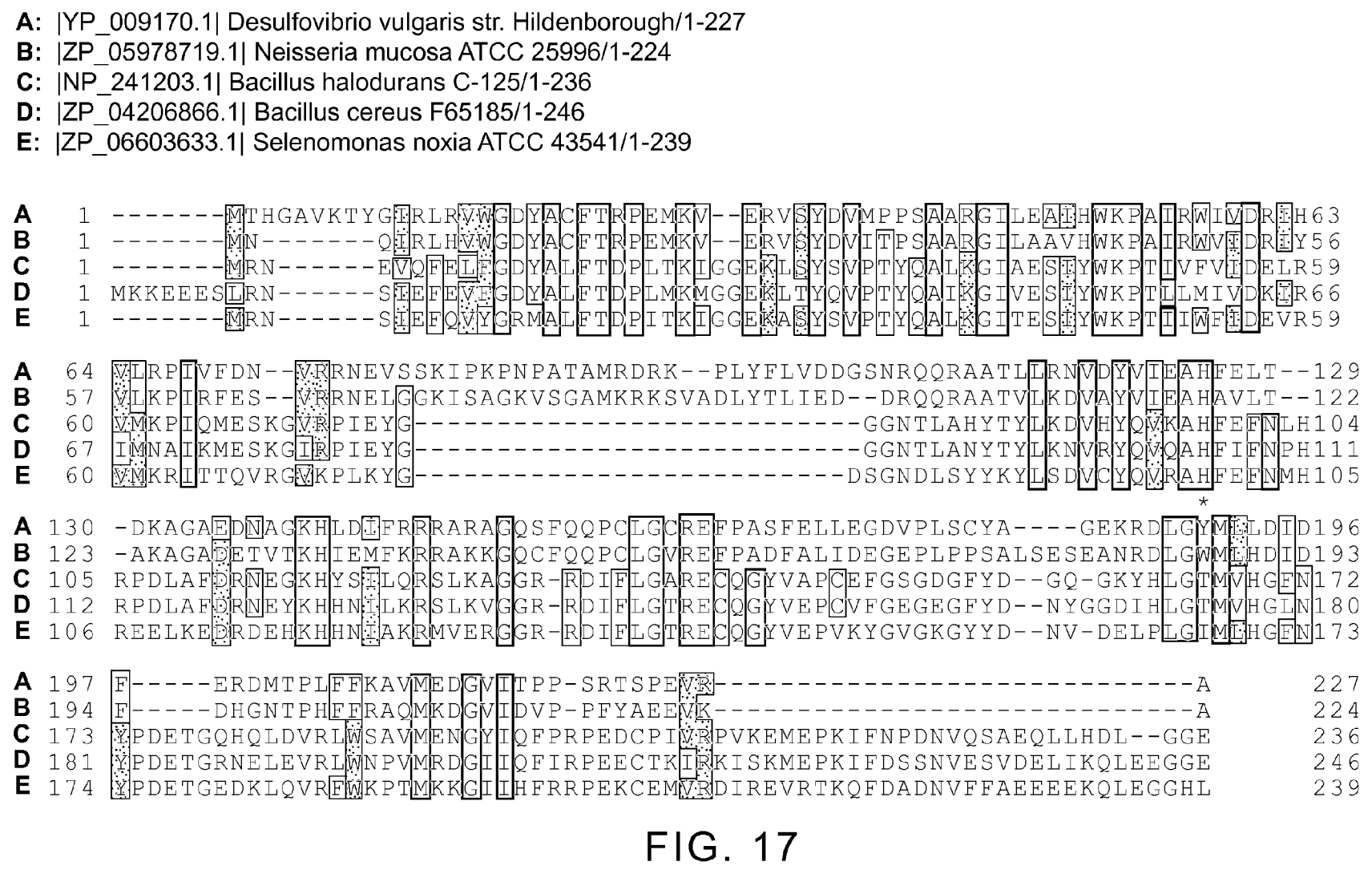

FIG. 17 provides an amino acid sequence alignment of the Cas5 amino acid sequences depicted in FIGS. 16A-E. (Top to bottom: SEQ ID NOs: 13, 46, 47, 48, 49).

FIGS. 22A-C depict cleavage of repeats R1 and R3 by TtCas6A and TtCas6B, and retention of the cleaved products. (Top to bottom: FIG. 22A, SEQ ID NOs: 1, 2, 55).

FIGS. 23A-D depict various structures of TtCas6A and TtCas6B enzymes bound to substrate mimic and product RNAs. (SEQ ID NO: 53). FIG. 23C shows the results from endonuclease activity assays of wild-type (WT) and active site mutant proteins. (SEQ ID NO: 53).

(FIG. 25D: left, SEQ ID NO: 56) (FIG. 25D: right bottom, SEQ ID NO: 57).

FIGS. 27A-C depict dimeric structures of TtCas6A and TtCas6B enzymes bound to substrate mimic and product RNAs.

FIGS. 28A-B depict sequence and structural alignments of TtCas6A and TtCas6B enzymes. (FIG. 28A: Top to bottom; amino acids 1-238 of SEQ ID NO: 19, amino acids 1-262 of SEQ ID NO: 24, all amino acids of SEQ ID NO: 58, all amino acids of SEQ ID NO: 59, and all amino acids of SEQ ID NO: 60).

FIG. 30 depicts a table of X-ray data collection and refinement statistics.

DEFINITIONS

Figure 1:
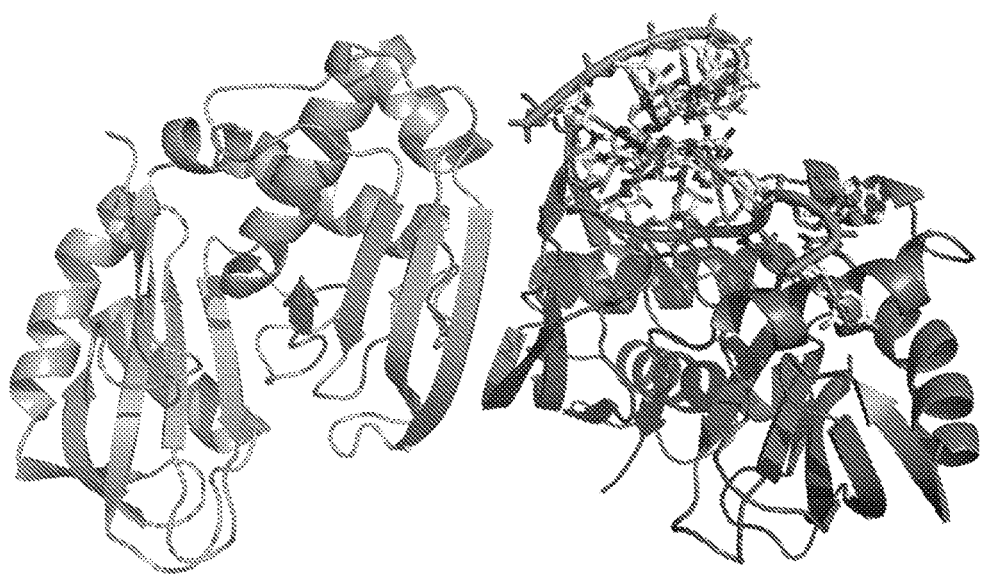
FIG. 1 depicts Cas6 protein TTHA0078 bound to nucleotides 15-30 of Tt_R1 containing a 2' deoxy at position G28, with the catalytic residue H37 highlighted in red.

As used herein, "polyribonucleotide" refers to a polymeric form of ribonucleotides, and includes RNA, RNA containing deoxyribonucleotide(s), and DNA containing ribonucleotide(s). A polyribonucleotide can in some cases include one or more modified nucleotides (e.g., deoxyinosine, deoxyuridine or hydroxymethyldeoxyuridine). In some cases, a polyribonucleotide consists of a ribonucleotides only (i.e., does not include any deoxyribonucleotides). In some cases, a polyribonucleotide comprises ribonucleotides, and one or more modified ribonucleotides, but does not include any deoxyribonucleotides. In other cases, a polyribonucleotide comprises ribonucleotides, and may comprise one or more modified ribonucleotides, and one or more deoxyribonucleotides (including modified deoxyribonucleotides). In some cases, where a polyribonucleotide comprises one or more deoxyribonucleotides, the deoxyribonucleotides comprise from about 50% to about 40%, from about 40% to about 30%, from about 30% to about 20%, from about 20% to about 10%, from about 10% to about 1%, or less than 1%, of the total nucleotides in the polyribonucleotide.

The terms "nucleic acid" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

A "biological sample" encompasses a variety of sample types obtained from a cell, extracellular matter, a tissue, or a multicellular organism. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid (e.g., cerebrospinal fluid, bronchoalveolar lavage fluid, urine, blood, a blood fraction (e.g., plasma; serum), sputum, and the like), and tissue samples. In some cases, a biological sample comprises cells. In other cases, a biological sample is cell free.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide.

"Isolated" refers to a protein or nucleic acid that, if naturally occurring, is in an environment different from that in which it may naturally occur. "Isolated" is meant to include proteins or nucleic acids that are within samples that are substantially enriched for the protein or nucleic acid of interest and/or in which the protein or nucleic acid of interest is partially or substantially purified. Where the protein or nucleic acid is not naturally occurring, "isolated" indicates the protein or nucleic acid has been separated from an environment in which it was made by either synthetic or recombinant means.

"Substantially pure" indicates that an entity (e.g., polypeptide or a nucleic acid) makes up greater than about 50% of the total content of the composition (e.g., total protein of the composition) and typically, greater than about 60% of the total protein content. In some embodiments, "substantially pure" refers to compositions in which at least 75%, at least 85%, at least 90% or more of the total composition is the entity of interest (e.g. 95%, of the total protein). In some embodiments, the protein or nucleic acid of interest will make up greater than about 90%, greater than about 95%, greater than about 98%, or greater than about 99%, of the total protein or nucleic acid in the composition.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a site-specific endoribonuclease" includes a plurality of such site-specific endoribonucleases and reference to "the target nucleic acid" includes reference to one or more target nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant Cas endoribonucleases, nucleic acids encoding the variant Cas endoribonucleases, and host cells genetically modified with the nucleic acids. The variant Cas endoribonucleases find use in a variety of applications, which are also provided. The present disclosure also provides methods of detecting a specific sequence in a target polyribonucleotide; and methods of regulating production of a target RNA in a eukaryotic cell.
Endoribonucleases The present disclosure provides a sequence-specific endoribonuclease. In some embodiments, the present disclosure provides a sequence-specific endoribonuclease that binds to a recognition sequence in a target polyribonucleotide, but that does not cleave the target polyribonucleotide, i.e., the sequence-specific endoribonuclease is enzymatically inactive in hydrolyzing the target polyribonucleotide. In some embodiments, the present disclosure provides a sequence-specific endoribonuclease that binds to a recognition sequence in a target polyribonucleotide, and cleaves the target polyribonucleotide within or near the recognition sequence, i.e., the sequence-specific endoribonuclease is enzymatically active in hydrolyzing the target polyribonucleotide.

In some embodiments, a subject sequence-specific endoribonuclease is immobilized on an insoluble substrate. Suitable insoluble substrates include, but are not limited to agarose beads, magnetic beads, a test strip, a multi-well dish, and the like. The insoluble substrate can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

Enzymatically Inactive Sequence-Specific Endoribonuclease

The present disclosure provides an enzymatically inactive, sequence-specific endoribonuclease, wherein the enzymatically inactive sequence-specific endoribonuclease binds to a target sequence in a polyribonucleotide in a sequence-specific manner. A subject enzymatically inactive, sequence-specific endoribonuclease binds a target polyribonucleotide in a sequence-specific manner, but does not cleave the target polyribonucleotide. A subject enzymatically inactive, sequence-specific endoribonuclease is useful for isolating a target RNA from a mixed population of nucleic acids, as described herein.

A subject enzymatically inactive, sequence-specific endoribonuclease is "conditionally" enzymatically inactive, e.g., a subject enzymatically inactive, sequence-specific endoribonuclease (e.g., a subject variant Cas6 endoribonuclease; a variant Cas5 endoribonuclease) is enzymatically inactive in the absence of imidazole; and the enzymatically inactive, sequence-specific endoribonuclease (e.g., subject variant Cas6 endoribonuclease; a variant Cas5 endoribonuclease) is activatable by imidazole. For example, the enzymatically inactive, sequence-specific endoribonuclease (e.g., subject variant Cas6 endoribonuclease; a variant Cas5 endoribonuclease) can be enzymatically activated by contacting the endoribonuclease with imidazole at a concentration of from about 100 mM to about 500 mM.

The presence of imidazole (e.g., in a concentration range of from about 100 mM to about 500 mM) reactivates the sequence-specific, enzymatically inactive endoribonuclease such that the endoribonuclease becomes enzymatically active, e.g., the endoribonuclease exhibits at least about 50%, at least about 60%, at least about 70%, at least about 80%, at least about 90%, at least about 95%, or more than 95%, of wild-type sequence-specific endoribonuclease (e.g., an amino acid sequence as set forth in one of SEQ ID NOs: 16-27 31, 33, 35, 37, and 39; an amino acid sequence as set forth in one of SEQ ID NOs: 13 and 41-49; and the like).
Variant Cas6 Polypeptides In some cases, a subject enzymatically inactive, sequence-specific endoribonuclease is a variant Cas6 polypeptide.

FIGS. 9, 10, and 11A-F depict non-limiting examples of amino acid sequences that can be modified to provide an enzymatically inactive, sequence-specific endoribonuclease. In some embodiments, a subject enzymatically inactive, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence set forth in one of SEQ ID NOs: 16-23, where the amino acid sequence includes a substitution at His-37, Arg-129 (or Arg-128 in the case of YP_005654445; or Arg-130 in the case of YP_004367049), or both His-37 and Arg-129 (or Arg-128 in the case of YP_005654445; or Arg-130 in the case of YP_004367049). For example, the variant Cas6 endoribonuclease can include a H37A (His-37 to Ala-37) substitution, an R129A (Arg-129 to Ala-129) substitution, or both a H37A and an R129A substitution.

In some embodiments, a subject enzymatically inactive, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, from about 225 amino acids to about 250 amino acids, or from about 250 amino acids to 264 amino acids, of an amino acid sequence set forth in one of SEQ ID NOs: 24-27, where the amino acid sequence includes a substitution at His-42 (e.g., a His-to-Ala substitution at amino acid 42).

In some embodiments, a subject enzymatically inactive, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids (aa) to about 175 amino acids, from about 175 amino acids to about 200 amino acids, from about 200 amino acids to about 225 amino acids, from about 225 amino acids to about 240 amino acids (e.g., 239 aa, 240 aa, 241 aa, 242 aa, 243 aa, 244 aa), from about 240 amino acids to about 250 amino acids, from about 250 amino acids to about 260 amino acids (e.g., 264 amino acids), from about 260 amino acids to about 275 amino acids (e.g., 277 amino acids), or from about 275 amino acids to 314 amino acids, of an amino acid sequence set forth in one of SEQ ID NOs: 19, 24, 31, 33, 35, 37, and 39, where the amino acid sequence includes a substitution at His-37 (e.g., a His-to-Ala substitution at amino acid 37) of the sequence set forth in one of SEQ ID NOs: 19 and 24 or a corresponding amino acid in a sequence set forth in one of SEQ ID NOs: 31, 33, 35, 37, and 39, where the His corresponding to His-37 of the sequence set forth in one of SEQ ID NOs: 19 and 24 is bolded and underlined in FIGS. 11B-F.

In some cases, the substrate recognized by a variant Cas6 polypeptide comprises a nucleotide sequence having at least about 80%, at least about 85%, at least about 90%, at least about 95%, at least about 98%, at least about 99%, or 100%, nucleotide sequence identity to one of the following sequences:

```
                                             (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUGAGGAUGAAAC-3';

(SEQ ID NO: 3)
5'-GGAUCGAUACCCACCCCGAAGAAAAGGGGACGAGAAC-3';
```

```
                                             (SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';
and
                                             (SEQ ID NO: 7)
5'-GUUCCAAUUAAUCUUAAACCCUAUUAGGGAUUGAAAC-3'.
```

In some cases, the substrate recognized by a variant Cas6 polypeptide comprises one of the following sequences:

```
                                             (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';

(SEQ ID NO: 7)
5'-GUUCCAAUUAAUCUUAAACCCUAUUAGGGAUUGAAAC-3',
``` or a "minimal" sequence depicted in FIGS. 11A-F (SEQ ID NOs: 28-29, 30, 32, 34, 36, and 38).

An RNA substrate recognized by a variant Cas6 polypeptide of the present disclosure can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

Variant Cas5 Polypeptides

In some cases, a subject enzymatically inactive, sequence-specific endoribonuclease is a variant Cas5 polypeptide.

FIGS. 15 and FIGS. 16A-E depict non-limiting examples of amino acid sequences that can be modified to provide an enzymatically inactive, sequence-specific endoribonuclease. In some embodiments, a subject enzymatically inactive, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence set forth in one of SEQ ID NOs: 13 and 41-49, where the amino acid sequence includes a substitution at His-141 of the sequence depicted in FIG. 15 as YP_009170

(SEQ ID NO: 13), or a corresponding histidine residue (see the His residue in bold in FIG. 15 or FIGS. 16A-E) in any of the amino acid sequences depicted in FIG. 15 (SEQ ID NOs: 13 and 41-45) or FIGS. 16A-E (SEQ ID NOs: 13 and 46-49).

In some cases, the substrate recognized by a variant Cas5 polypeptide comprises one of the following sequences:

```
                                           (SEQ ID NO: 8)
5'-GUCGCCCCCACGCGGGGGCGUGGAUUGAAAC-3';

(SEQ ID NO: 9)
5'-CCAGCCGCCUUCGGGCGGCUGUGUGUUGAAAC-3';

(SEQ ID NO: 10)
5'-GUCGCACUCUACAUGAGUGCGUGGAUUGAAAU-3';

(SEQ ID NO: 11)
5'-UGUCGCACCUUAUAUAGGUGCGUGGAUUGAAAU-3';
and (SEQ ID NO: 12)
5'-GUCGCGCCCCGCAUGGGGCGCGUGGAUUGAAA-3',
``` or a "minimal" sequence depicted in FIGS. 16A-E (SEQ ID NOs: 8-12).

An RNA substrate recognized by a variant Cas5 polypeptide of the present disclosure can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

Modifications

In some embodiments, a subject enzymatically inactive, sequence-specific endoribonuclease (e.g., a subject variant Cas6 endoribonuclease; a subject variant Cas5 endoribonuclease) comprises a detectable label, including a moiety that provides a detectable signal. Suitable detectable labels and/or moieties that provide a detectable signal include, but are not limited to, an enzyme, a radioisotope, a member of a FRET pair, a member of a specific binding pair; a fluorophore; a fluorescent protein; a quantum dot; and the like.

FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705. In addition, a fluorophore/quantum dot donor/acceptor pair can be used.

Suitable fluorophores ("fluorescent label") include any molecule that may be detected via its inherent fluorescent properties, which include fluorescence detectable upon excitation. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 2002 Molecular Probes Handbook, 9th Ed., by Richard P. Haugland, hereby expressly incorporated by reference.

Suitable enzymes include, but are not limited to, horse radish peroxidase, luciferase, β-galactosidase, alkaline phosphatase, and the like.

Suitable fluorescent proteins include, but are not limited to, a green fluorescent protein (GFP), e.g., a GFP from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

Suitable nanoparticles include, e.g., quantum dots (QDs), fluorescent or luminescent nanoparticles, and magnetic nanoparticles. Any optical or magnetic property or characteristic of the nanoparticle(s) can be detected.

QDs and methods for their synthesis are well known in the art (see, e.g., U.S. Pat. Nos. 6,322,901; 6,576,291; and 6,815,064). QDs can be rendered water soluble by applying coating layers comprising a variety of different materials (see, e.g., U.S. Pat. Nos. 6,423,551; 6,251,303; 6,319,426; 6,426,513; 6,444,143; and 6,649,138). For example, QDs can be solubilized using amphiphilic polymers. Exemplary polymers that have been employed include octylamine-modified low molecular weight polyacrylic acid, polyethylene-glycol (PEG)-derivatized phospholipids, polyanhydrides, block copolymers, etc. QDs can be conjugated to a polypeptide via any of a number of different functional groups or linking agents that can be directly or indirectly linked to a coating layer (see, e.g., U.S. Pat. Nos. 5,990,479; 6,207,392; 6,251,303; 6,306,610; 6,325,144; and 6,423,551).

QDs with a wide variety of absorption and emission spectra are commercially available, e.g., from Quantum Dot Corp. (Hayward Calif.; now owned by Invitrogen) or from Evident Technologies (Troy, N.Y.). For example, QDs having peak emission wavelengths of approximately 525, 535, 545, 565, 585, 605, 655, 705, and 800 nm are available. Thus the QDs can have a range of different colors across the visible portion of the spectrum and in some cases even beyond.

Suitable radioisotopes include, but are not limited to $^{14}$C, $^{3}$H, $^{32}$P, $^{33}$P, $^{35}$S, $^{125}$I, and $^{131}$I. The use of radioisotopes as labels is well known in the art.

In some embodiments, a subject enzymatically inactive, sequence-specific endoribonuclease (e.g., a subject variant Cas6 endoribonuclease) is immobilized on an insoluble substrate. Suitable insoluble substrates include, but are not limited to agarose beads, magnetic beads, a test strip, a multi-well dish, and the like. The insoluble substrate can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

In some embodiments, a subject enzymatically inactive, sequence-specific endoribonuclease (e.g., a subject variant Cas6 endoribonuclease, a subject variant Cas5 endoribonuclease) is purified, e.g., is at least 80% pure, at least 85% pure, at least 90% pure, at least 95% pure, at least 98% pure, at least 99% pure, or greater than 99% pure.

Compositions

The present disclosure provides compositions comprising a subject sequence-specific, enzymatically inactive, endoribonuclease. A subject composition can comprise, in addition to a subject sequence-specific, enzymatically inactive, endoribonuclease, one or more of: a salt, e.g., NaCl, MgCl$_2$, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a reducing agent, e.g., dithiothreitol; a protease inhibitor; and the like.

Enzymatically Active Sequence-Specific Endoribonuclease

Endoribonucleases suitable for use in a subject method will in some embodiments be an enzymatically active sequence-specific endoribonuclease (e.g., a Cas6 polypeptide or a Cas5 polypeptide).

Suitable Cas6 polypeptide amino acid sequences are provided in, e.g., GenBank Accession No. YP_143344 (*Thermus thermophilus* HB8); GenBank Accession No. YP_145470 (*Thermus thermophilus* HB8); GenBank Accession No. YP_005869 (*Thermus thermophilus* HB27); GenBank Accession No. YP_006059433 (*Thermus thermophilus* JL-18); GenBank Accession No. YP_005654445 (*Thermus* sp. CCB_US3_UF1); GenBank Accession No. ZP_03497188 (*Thermus aquaticus*); GenBank Accession No. YP_003684129 (*Meiothermus silvanus* DSM 9946); GenBank Accession No. YP_004367049 (*Marinithermus hydrothermalis*); GenBank Accession No. YP_005641609 (*Thermus thermophilus* SG0.5JP17-16); GenBank Accession No. YP_006185 (*Thermus thermophilus* HB27); GenBank Accession No. YP_006059769 (*Thermus thermophilus* JL-18); YP_003506022 *Meiothermus ruber* DSM 1279).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIGS. 9A and 9B (SEQ ID NOs: 16-23).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, from about 225 amino acids to about 250 amino acids, or from about 250 amino acids to 264 amino acids, of an amino acid sequence depicted in FIG. 10 (SEQ ID NOs: 24-27).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids (aa) to about 175 amino acids, from about 175 amino acids to about 200 amino acids, from about 200 amino acids to about 225 amino acids, from about 225 amino acids to about 240 amino acids (e.g., 239 aa, 240 aa, 241 aa, 242 aa, 243 aa, 244 aa), from about 240 amino acids to about 250 amino acids, from about 250 amino acids to about 260 amino acids (e.g., 264 amino acids), from about 260 amino acids to about 275 amino acids (e.g., 277 amino acids), or from about 275 amino acids to 314 amino acids, of an amino acid sequence depicted in FIGS. 11A-F or FIG. 12 (SEQ ID NOs: 19, 24, 31, 33, 35, 37, and 39).

In some cases, the substrate recognized by a Cas6 polypeptide comprises a nucleotide sequence having at least about 80%, at least about 85%, at least about 90%, at least about 95%, at least about 98%, at least about 99%, or 100%, nucleotide sequence identity to one of the following sequences:

```
                                              (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';
and (SEQ ID NO: 7)
5'-GUUCCAAUUAAUCUUAAACCCUAUUAGGGAUUGAAAC-3'.
```

In some cases, the substrate recognized by a Cas6 polypeptide comprises one of the following sequences:

```
                                              (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';

(SEQ ID NO: 7)
5'-GUUCCAAUUAAUCUUAAACCCUAUUAGGGAUUGAAAC-3',
``` or a "minimal" sequence depicted in FIGS. 11A-F (SEQ ID NOs: 28-29, 30, 32, 34, 36, and 38).

An RNA substrate recognized by a Cas6 polypeptide can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

Suitable Cas5 polypeptides are provided in, e.g., GenBank Accession No. YP_009170 (*Desulfovibrio vulgaris*

Cas5); GenBank Accession No. YP_004513910 (*Methylomonas methanica* MC09 Cas5); GenBank Accession No. YP_004496339 (*Desulfotomaculum carboxydivorans* Cas5); GenBank Accession No. ZP_05883174 (*Vibrio metchnikovii* Cas5); GenBank Accession No. YP_001174211 (*Pseudomonas stutzeri* Cas5); etc.

In some embodiments, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIG. 15 (SEQ ID NOs: 13 and 41-45), or in FIGS. 16A-E (SEQ ID NOs: 13 and 46-49).

In some cases, the substrate recognized by a variant Cas5 polypeptide comprises one of the following sequences:

```
                                          (SEQ ID NO: 8)
5'-GUCGCCCCCACGCGGGGGCGUGGAUUGAAAC-3';

(SEQ ID NO: 9)
5'-CCAGCCGCCUUCGGCGGCUGUGUGUUGAAAC-3';

(SEQ ID NO: 10)
5'-GUCGCACUCUACAUGAGUGCGUGGAUUGAAAU-3';

(SEQ ID NO: 11)
5'-UGUCGCACCUUAUAUAGGUGCGUGGAUUGAAAU-3';
and (SEQ ID NO: 12)
5'-GUCGCGCCCCGCAUGGGGCGCGUGGAUUGAAA-3',
``` or a "minimal" sequence depicted in FIGS. 16A-E (SEQ ID NOs: 8-12).

An RNA substrate recognized by a Cas5 polypeptide can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

In some instance, an enzymatically active sequence-specific endoribonuclease comprises a moiety that provides for detection. For example, a subject enzymatically active sequence-specific endoribonuclease can comprise a covalently or non-covalently linked moiety that provides for detection.

Suitable detectable labels include any composition detectable by spectroscopic, photochemical, biochemical, immunochemical, electrical, optical or chemical means. Moieties that provide for detection include, but are not limited to, a fluorescent molecule; a quantum dot; an enzyme (other than the endoribonuclease), where the enzyme catalyzes conversion of a substrate to a detectable product, where the product is directly detectable; a nanoparticle; and the like.

Suitable fluorescent proteins that can be linked to a subject enzymatically active sequence-specific endoribonuclease include, but are not limited to, a green fluorescent protein (GFP), e.g., a GFP from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

Suitable nanoparticles include, e.g., quantum dots (QDs), fluorescent or luminescent nanoparticles, and magnetic nanoparticles. Any optical or magnetic property or characteristic of the nanoparticle(s) can be detected.

QDs and methods for their synthesis are well known in the art (see, e.g., U.S. Pat. Nos. 6,322,901; 6,576,291; and 6,815,064). QDs can be rendered water soluble by applying coating layers comprising a variety of different materials (see, e.g., U.S. Pat. Nos. 6,423,551; 6,251,303; 6,319,426; 6,426,513; 6,444,143; and 6,649,138). For example, QDs can be solubilized using amphiphilic polymers. Exemplary polymers that have been employed include octylamine-modified low molecular weight polyacrylic acid, polyethylene-glycol (PEG)-derivatized phospholipids, polyanhydrides, block copolymers, etc. QDs can be conjugated to a polypeptide via any of a number of different functional groups or linking agents that can be directly or indirectly linked to a coating layer (see, e.g., U.S. Pat. Nos. 5,990,479; 6,207,392; 6,251,303; 6,306,610; 6,325,144; and 6,423,551).

QDs with a wide variety of absorption and emission spectra are commercially available, e.g., from Quantum Dot Corp. (Hayward Calif.; now owned by Invitrogen) or from Evident Technologies (Troy, N.Y.). For example, QDs having peak emission wavelengths of approximately 525, 535, 545, 565, 585, 605, 655, 705, and 800 nm are available. Thus the QDs can have a range of different colors across the visible portion of the spectrum and in some cases even beyond.

In some embodiments, a subject enzymatically active, sequence-specific endoribonuclease is purified, e.g., is at least 80% pure, at least 85% pure, at least 90% pure, at least 95% pure, at least 98% pure, at least 99% pure, or greater than 99% pure.

Compositions

The present disclosure provides compositions comprising a subject sequence-specific, enzymatically active endoribonuclease. A subject composition can comprise, in addition to a subject sequence-specific enzymatically active, endoribonuclease, one or more of: a salt, e.g., NaCl, MgCl$_2$, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Methods of Producing a Sequence-Specific Endoribonuclease

A subject sequence-specific endoribonuclease (e.g., a subject sequence-specific enzymatically active, endoribonuclease; a subject sequence-specific enzymatically inactive, endoribonuclease) can be produced by any known method, e.g., conventional synthetic methods for protein synthesis; recombinant DNA methods; etc.

Where a subject sequence-specific endoribonuclease is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject sequence-specific endoribonuclease. Various forms of SPPS, such as Fmoc and Boc, are available for synthesizing a subject sequence-specific endoribonuclease. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8.

Standard recombinant methods can be used for production of a subject sequence-specific endoribonuclease. For example, nucleic acids encoding a subject sequence-specific endoribonuclease are inserted into expression vectors. The DNA segments encoding a subject sequence-specific endoribonuclease are operably linked to control sequences in the expression vector(s) that ensure the expression of the encoded polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the endoribonuclease.

Nucleic Acids and Host Cells

The present disclosure provides a nucleic acid comprising a nucleotide sequence encoding a subject sequence-specific endoribonuclease (e.g., a subject sequence-specific, enzymatically active endoribonuclease; a subject sequence-specific, enzymatically inactive endoribonuclease). In some embodiments, the nucleic acid is an expression vector, where the expression vector can provide for production of the sequence-specific endoribonuclease, e.g., in a cell.

A nucleotide sequence encoding a subject sequence-specific endoribonuclease (e.g., a subject sequence-specific, enzymatically active endoribonuclease; a subject sequence-specific, enzymatically inactive endoribonuclease) can be operably linked to one or more regulatory elements, such as a promoter and enhancer, that allow expression of the nucleotide sequence in the intended target cells (e.g., a cell that is genetically modified to synthesize the encoded endoribonuclease).

In some embodiments, a subject nucleic acid comprises a nucleotide sequence encoding a polypeptide having at least about 60%, at least about 65%, at least about 70%, at least about 75%, at least about 80%, at least about 85%, at least about 90%, at least about 95%, at least about 98%, at least about 99%, or 100%, with an amino acid sequence set forth in any one of FIGS. 9A, 9B, 10, 11A-F, and 12 (SEQ ID NOs: 16-27, 31, 33, 35, 37, and 39). In some embodiments, a subject nucleic acid comprises a nucleotide sequence encoding a variant Cas6 polypeptide, as described above.

In some embodiments, a subject nucleic acid comprises a nucleotide sequence encoding a polypeptide having at least about 60%, at least about 65%, at least about 70%, at least about 75%, at least about 80%, at least about 85%, at least about 90%, at least about 95%, at least about 98%, at least about 99%, or 100%, with an amino acid sequence set forth in FIG. 15 (SEQ ID NOs: 13 and 41-45) or FIGS. 16A-E (SEQ ID NOs: 13 and 46-49). In some embodiments, a subject nucleic acid comprises a nucleotide sequence encoding a variant Cas5 polypeptide, as described above.

A nucleotide sequence encoding a subject sequence-specific endoribonuclease (e.g., a subject sequence-specific, enzymatically active endoribonuclease; a subject sequence-specific, enzymatically inactive endoribonuclease) can be operably linked to a transcription control element (e.g., a promoter, an enhancer, etc.). Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al. (1984) Nucl. Acids Res. 12:7035); and the like. Suitable strong promoters for use in prokaryotes such as Escherichia coli include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject sequence-specific endoribonuclease (e.g., a subject sequence-specific, enzymatically active endoribonuclease; a subject sequence-specific, enzymatically inactive endoribonuclease) can be present in an expression vector and/or a cloning vector. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

The present disclosure provides isolated genetically modified host cells (e.g., in vitro cells) that are genetically modified with a subject nucleic acid. In some embodiments, a subject isolated genetically modified host cell can produce a subject sequence-specific endoribonuclease (e.g., a subject sequence-specific, enzymatically active endoribonuclease; a subject sequence-specific, enzymatically inactive endoribonuclease).

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, *Chlamydomonas reinhardtii*, and the like.

Suitable prokaryotic cells include, but are not limited to, any of a variety of laboratory strains of *Escherichia coli*, *Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some embodiments, the host cell is *Escherichia coli*.

Methods of Directly Sequencing a Target Polyribonucleotide

The present disclosure provides a method of directly determining the nucleotide sequence of a target polyribonucleotide. Thus, for example, the method does not require synthesis of a polydeoxyribonucleotide counterpart of a target polyribonucleotide in order to determine the nucleotide sequence of the target polyribonucleotide.

Viral diagnostics, personalized medicine, single-cell transcript analysis, and translational profiling are all fields in which direct RNA detection and sequencing find use. A subject polyribonucleotide sequencing method, and a subject method of detecting a specific sequence in a polyribonucleotide, find use in these various fields.

A subject polyribonucleotide sequencing method generally involves: a) contacting a target polyribonucleotide with an oligonucleotide probe comprising a specific known sequence and an enzymatically inactive sequence-specific endoribonuclease under conditions that favor duplex formation between the oligonucleotide probe and the target polyribonucleotide, wherein the enzymatically inactive sequence-specific endoribonuclease binds the specific sequence in the duplex; and b) detecting specific binding between the oligonucleotide probe and the target polyribonucleotide, where specific binding of the enzymatically inactive sequence-specific endoribonuclease to the duplex indicates the presence of the specific sequence in the target polyribonucleotide.

In some cases, the enzymatically inactive sequence-specific endoribonuclease is linked (covalently or non-covalently) to an emissive label. By "emissive label" is meant any molecule that may be detected via its inherent emission properties, which include emission detectable upon excitation. Suitable emissive labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 2002 Molecular Probes Handbook, 9th Ed., by Richard P. Haugland.

In some instances, the oligonucleotide probe used in a subject polyribonucleotide sequencing method is linked to a donor molecule, the enzymatically inactive sequence-specific endoribonuclease is linked to an acceptor molecule, and detection of duplex formation is by fluorescence resonance energy transfer (also referred to as "Förster resonance energy transfer" or "FRET").

Förster resonance energy transfer (FRET) is phenomenon known in the art wherein excitation of one emissive dye is transferred to another without emission of a photon. A FRET pair consists of a donor chromophore and an acceptor chromophore (where the acceptor chromophore may be a quencher molecule). The emission spectrum of the donor and the absorption spectrum of the acceptor must overlap, and the two molecules must be in close proximity. The distance between donor and acceptor at which 50% of donors are deactivated (transfer energy to the acceptor) is defined by the Förster radius, which is typically 10-100 angstroms. Changes in the emission spectrum comprising FRET pairs can be detected, indicating changes in the number of that are in close proximity (i.e., within 100 angstroms of each other). This will typically result from the binding or dissociation of two molecules, one of which is labeled with a FRET donor and the other of which is labeled with a FRET acceptor, wherein such binding brings the FRET pair in close proximity.

Binding of such molecules will result in an increased emission of the acceptor and/or quenching of the fluorescence emission of the donor. FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705. In addition, a fluorophore/quantum dot donor/acceptor pair can be used. EDANS is (5-((2-Aminoethyl)amino)naphthalene-1-sulfonic acid); IAEDANS is 5-({2-[(iodoacetyl)amino]ethyl}amino)naphthalene-1-sulfonic acid); DABCYL is 4-(4-dimethylaminophenyl)diazenylbenzoic acid.

Cy3, Cy5, Cy 5.5, and the like, are cyanines. For example, Cy3 and Cy5 are reactive water-soluble fluorescent dyes of the cyanine dye family. Cy3 dyes are red (~550 nm excitation, ~570 nm emission and therefore appear green), while Cy5 is fluorescent in the red region (~650/670 nm) but absorbs in the orange region (~649 nm). Alexa Fluor dyes, Dylight, IRIS Dyes, Seta dyes, SeTau dyes, SRfluor dyes and Square dyes can also be used.

In another aspect of FRET, an emissive donor molecule and a nonemissive acceptor molecule ("quencher") may be employed. In this application, emission of the donor will increase when quencher is displaced from close proximity to the donor and emission will decrease when the quencher is brought into close proximity to the donor. Useful quenchers include, but are not limited to, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

In some cases, the enzymatically inactive sequence-specific endoribonuclease is linked (covalently or non-covalently) to a label enzyme. By "label enzyme" is meant an enzyme which may be reacted in the presence of a label enzyme substrate which produces a detectable product. Suitable label enzymes also include optically detectable labels (e.g., in the case of horse radish peroxidase (HRP)). Suitable label enzymes include but are not limited to, HRP, alkaline phosphatase, luciferase, β-galactosidase, and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6-9 (1998), Young, J. Virol. Methods 24:227-236 (1989).

In some cases, the enzymatically inactive sequence-specific endoribonuclease comprises a radioisotope. By "radioisotope" is meant any radioactive molecule. Suitable radioisotopes for use in the invention include, but are not limited to $^{14}C$, $^{3}H$, $^{32}P$, $^{33}P$, $^{35}S$, $^{125}I$, and $^{131}I$. The use of radioisotopes as labels is well known in the art.

In some cases, the enzymatically inactive sequence-specific endoribonuclease is linked (covalently or non-covalently) to a member of a specific binding pair ("partner of a binding pair"). By "partner of a binding pair" or "member of a binding pair" is meant one of a first and a second moiety, wherein the first and the second moiety have a specific binding affinity for each other. Suitable binding pairs include, but are not limited to, antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin.

In some embodiments, the oligonucleotide probe comprises a modification that provides for increased resistance to non-specific hydrolysis. Such modifications are well known in the art and include, e.g., nuclease-resistant internucleosidic linkages, modified backbones, base modifications, base substitutions, sugar modifications, and the like.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

A modified oligonucleotide can comprise one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in U.S. Pat. No. 5,489,677. Suitable amide internucleoside linkages are disclosed in U.S. Pat. No. 5,602,240.

A modified oligonucleotide can comprise one or more morpholino backbone structures as described in, e.g., U.S. Pat. No. 5,034,506. For example, in some embodiments, a modified oligonucleotide comprises a 6-membered morpholino ring in place of a ribose ring. In some of these embodiments, a phosphorodiamidate or other non-phosphodiester internucleoside linkage replaces a phosphodiester linkage. Morpholino nucleic acids ("morpholinos") include bases bound to morpholine rings instead of deoxyribose rings; in addition, the phosphate backbone can include a non-phosphate group, e.g., a phosphorodiamidate group instead of phosphates. Summerton (1999) *Biochim. Biophys. Acta* 1489:141; Heasman (2002) *Dev. Biol.* 243:209; Summerton and Weller (1997) *Antisense & Nucl. Acid Drug Dev.* 7:187; Hudziak et al. (1996) *Antisense & Nucl. Acid Drug Dev.* 6:267; Partridge et al. (1996) *Antisense & Nucl. Acid Drug Dev.* 6:169; Amantana et al. (2007) *Bioconj. Chem.* 18:1325; Morcos et al. (2008) *BioTechniques* 45:616.

A modified oligonucleotide can comprise a modified backbone. Modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A modified oligonucleotide can comprise one or more substituted sugar moieties. Suitable oligonucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are O(($CH_2$)$_n$O)$_m$$CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON(($CH_2$)$_n$CH$_3$)$_2$, where n and m are from 1 to about 10. Other suitable oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, and the like. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a O($CH_2$)$_2$ON($CH_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$.

A modified oligonucleotide can comprise one or more nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone.

A suitable enzymatically inactive sequence-specific endoribonuclease includes an enzymatically inactive sequence-specific endoribonuclease described hereinbelow. For example, an enzymatically inactive sequence-specific endoribonuclease that is a variant of an amino acid sequence as depicted in any one of FIGS. 9A, 9B, 10, 11A-F, 12, 15, and 16A-E (SEQ ID NOS: 16-27, 31, 33, 35, 37, and 39 or SEQ ID NOs: 13, and 41-49), where the variant is as described above (e.g., with a substitution of a histidine that renders the endoribonuclease conditionally inactive) can be used.

In some embodiments, the target polyribonucleotide is linked (covalently or non-covalently) to a solid support (an insoluble support). Suitable insoluble supports include, but are not limited to, beads, plates (e.g., multi-well plates), strips, etc., where the insoluble support can comprise various materials including, but not limited to, polystyrene, polypropylene, agarose, and the like.

Oligonucleotide probes ("detection oligonucleotide") can be RNA, DNA, or any chemically modified version of an RNA or DNA, e.g., peptide nucleic acids (PNAs), locked nucleic acids (LNAs), and the like.

A subject polyribonucleotide sequencing method can include one or more washing steps, e.g., to remove non-specifically bound components such as non-specifically bound oligonucleotide probes, any non-specifically bound detectable moieties, and the like.

A non-limiting example of how to carry out a subject polyribonucleotide sequencing method is as follows. A target polyribonucleotide bound to a solid support. The target polyribonucleotide is of unknown sequence and is the "RNA to be sequenced." Four oligonucleotide probes of four different known nucleotide sequences each comprise a different fluorophore (fluorophores 1-4). The fluorophores are members of FRET pairs. The counterpart members of the FRET pairs are quantum dots. The quantum dot is linked to an enzymatically inactive sequence-specific endoribonuclease. The enzymatically inactive sequence-specific endoribonuclease binds, but does not cleave, the duplex formed between an oligonucleotide probe and the target polyribonucleotide. Only one of the four oligonucleotide probes binds to and forms a duplex with the target polyribonucleotide. A washing step removes any unbound oligonucleotide probes. Binding of oligonucleotide probe-fluorophore2 results in duplex formation with the target polyribonucleotide. Fluorophore2 is thus brought into proximity to the quantum dot linked to the enzymatically inactive sequence-specific endoribonuclease, and fluorescence is quenched.

Methods of Cleaving a Polyribonucleotide

The present disclosure provides a method of cleaving a polyribonucleotide in a sequence-specific manner. The method generally involves contacting a substrate polyribonucleotide with an enzymatically active sequence-specific endoribonuclease (e.g., a Cas5 endoribonuclease; a Cas6 endoribonuclease) under conditions that favor sequence-specific cleavage of the polyribonucleotide substrate. A subject method of cleaving a polyribonucleotide in a sequence-specific manner can be used to: 1) remove an affinity tag from a substrate polyribonucleotide; 2) to generate a population of product polyribonucleotides having homogeneity at the 5' end, e.g., where the substrate polyribonucleotides are in vitro transcribed mRNAs; and 3) to regulate gene expression in a cell in vitro or in vivo.

Substrate Polyribonucleotides

The terms "substrate polyribonucleotide" and "target polyribonucleotide" are used interchangeably herein to refer to a polyribonucleotide that is bound by a sequence-specific endoribonuclease in a sequence-specific manner. A substrate polyribonucleotide can be single stranded. In some instances, a substrate polyribonucleotide is double stranded.

An endoribonuclease binds to and cleaves a substrate polyribonucleotide in a sequence-specific manner. Thus, for example, an endoribonuclease binds to and cleaves a substrate polyribonucleotide at a specific sequence, referred to herein as a "recognition sequence" or a "recognition site."

A recognition sequence can be a tetranucleotide sequence, a pentanucleotide sequence, a hexanucleotide sequence, a heptanucleotide sequence, an octanucleotide sequence, or longer than an octanucleotide. For example, in some embodiments, the recognition sequence is 9 ribonucleotides, 10 ribonucleotides, 11 ribonucleotides, 12 ribonucleotides, 13 ribonucleotides, 14 ribonucleotides, 15 ribonucleotides, 16 ribonucleotides, 17 ribonucleotides, 18 ribonucleotides, 19 ribonucleotides, or 20 ribonucleotides in length. In some embodiments, a sequence-specific endoribonuclease cleaves immediately 5' of a recognition sequence. In some embodiments, a sequence-specific endoribonuclease cleaves immediately 3' of a recognition sequence. In some embodiments, a sequence-specific endoribonuclease cleaves within a recognition sequence. In some cases, a recognition sequence is immediately 5' of a secondary structure. In some cases, a recognition sequence is located 5' of a secondary structure and within 1 nucleotide (nt), 2 nt, 3 nt, 4 nt, 5 nt, or 5 nt to 10 nt of the secondary structure. In some cases, a recognition sequence is immediately 3' of a secondary structure. In some cases, a recognition sequence is located 3' of a secondary structure and within 1 nucleotide (nt), 2 nt, 3 nt, 4 nt, 5 nt, or 5 nt to 10 nt of the secondary structure.

In some embodiments, a substrate polyribonucleotide comprises the structure $X_xX_2X_3X_4X_5X_6X_7X_8X_9X_{10}X_{11}X_{12}X_{13}X_{14}X_{15}$, where nucleotides $X_1$-$X_5$ base pair with $X_{11}$-$X_{15}$ such that $X_1$ and $X_{15}$ form the base of a stem structure, and such that $X_6$, $X_7$, $X_8$, $X_9$, and $X_{10}$ form a loop; the structure is a regular A-form helical structure.

In some embodiments, the substrate polyribonucleotide comprises an affinity tag; and a subject method provides for removal of the affinity tag from the substrate polyribonucleotide.

Sequence-Specific Endoribonucleases

Endoribonucleases that bind to and cleave a substrate polyribonucleotide in a sequence-specific manner include enzymatically active polypeptides that cleave (hydrolyze) a substrate polyribonucleotide in a metal ion-independent fashion.

Suitable endoribonucleases are sequence-specific, enzymatically active endoribonucleases (e.g., Cas5 endoribonucleases; Cas6 endoribonucleases) as described above.

Reaction Conditions

A sequence-specific endoribonuclease can hydrolyze a substrate polyribonucleotide in a sequence-specific manner at a temperature in a range from about 15° C. to about 100° C., e.g., in a range of from about 15° C. to about 17° C., from about 17° C. to about 20° C., from about 20° C. to about 25° C., from about 25° C. to about 30° C., from about 30° C. to about 40° C., from about 40° C. to about 50° C., from about 50° C. to about 60° C., from about 60° C. to about 70° C., from about 70° C. to about 80° C., from about 80° C. to about 90° C., or from about 90° C. to about 100° C.

A sequence-specific endoribonuclease can hydrolyze a substrate polyribonucleotide in a sequence-specific manner in a pH range of from about 4.0 to about 8.0, e.g., from about pH 4.0 to about 4.5, from about pH 4.5 to about 5.0, from about pH 5.0 to about 5.5, from about pH 5.5 to about 6.0, from about pH 6.0 to about 6.5, from about pH 6.5 to about 7.0, from about pH 7.0 to about 7.5, from about pH 6.5 to about 7.5, from about pH 7.5 to about 8.0, from about pH 6.5 to about 8.0, or from about pH 5.5 to about 7.5.

Methods of Detecting a Sequence in a Target Polyribonucleotide

The present disclosure provides a method of detecting a sequence in a target polyribonucleotide. The methods are useful for detecting the presence of a particular sequence in a polyribonucleotide, and can therefore be used to detect a polyribonucleotide comprising a particular sequence. For example, the method can be used to detect the presence of a polyribonucleotide of a pathogen in a sample (e.g., in a biological sample).

A subject method can detect as few as 100 copies, down to a single copy, of a target polyribonucleotide. Thus, e.g., a subject method can detect from 1 to about 5, from about 5 to about 10, from about 10 to about 50, or from about 50 to about 100, or more than 100, copies of a target polyribonucleotide in a sample (e.g., in a single cell, in a single embryo, or other biological sample). A subject method is thus useful for various forensic, research, and diagnostic applications.

In some embodiments, a subject method of detecting a specific sequence in a target polyribonucleotide comprises: a) contacting the target polyribonucleotide with a oligonucleotide probe comprising the specific sequence and an enzymatically active sequence-specific Cas5 endoribonuclease under conditions that favor duplex formation between the oligonucleotide probe and the target polyribonucleotide, wherein the duplex is cleaved by the Cas5 endoribonuclease; and b) detecting specific binding between the oligonucleotide probe and the target polyribonucleotide, wherein detection of duplex formation between the oligonucleotide probe and the target polyribonucleotide indicates the presence of the specific sequence in the target polyribonucleotide.

In other embodiments, a subject method of detecting a specific sequence in a target polyribonucleotide comprises: a) contacting the target polyribonucleotide with a oligonucleotide probe comprising the specific sequence and an enzymatically active sequence-specific Cas6 endoribonuclease under conditions that favor duplex formation between the oligonucleotide probe and the target polyribonucleotide, wherein the duplex is cleaved by the Cas6 endoribonuclease; and b) detecting specific binding between the oligonucleotide probe and the target polyribonucleotide, wherein detection of duplex formation between the oligonucleotide probe and the target polyribonucleotide indicates the presence of the specific sequence in the target polyribonucleotide.

In some cases, the oligonucleotide probe is linked to a peptide, and the peptide is released upon cleavage of the duplex by the Cas5 endoribonuclease or the Cas6 endoribonuclease; in these cases, the detection step involves detection of the released peptide. For example, the released peptide is detected by binding to an antibody specific for the peptide, e.g., where the antibody is immobilized. In some embodiments, the target polyribonucleotide is immobilized on a solid support. Target polyribonucleotides include any of a variety of polynucleotides, e.g., the target polyribonucleotide can be a polyribonucleotide of a pathogen.

As noted above, in some embodiments, the antibody or the target polynucleotide is immobilized on a solid support (insoluble support). Suitable insoluble supports include, but are not limited to agarose beads, magnetic beads, a test strip, a multi-well dish, and the like. The insoluble support can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

In some embodiments, the method generally involves: a) contacting a target polyribonucleotide with a sequence-specific endoribonuclease; and b) detecting cleavage fragments produced by site-specific cleavage of the target polyribonucleotide, where production of cleavage fragments expected upon cleavage at a specific sequence in the polyribonucleotide indicates the presence of the specific sequence.

In other embodiments, a subject method of detecting a sequence in a target polyribonucleotide involves: a) contacting a target polyribonucleotide with: i) a sequence-specific endoribonuclease; and ii) an oligonucleotide probe comprising a linked detection moiety, where the oligonucleotide probe comprises a specific, known nucleotide sequence; wherein the oligonucleotide probe forms a duplex with a complementary sequence in the target polyribonucleotide based on binding of the known nucleotide sequence present in the oligonucleotide probe to a complementary sequence in the target polyribonucleotide, and where the sequence-specific endoribonuclease cleaves the duplex in a sequence-specific manner, thereby releasing the detection moiety from the oligonucleotide probe; and b) detecting the released detection moiety, where release of the detection moiety indicates the presence of the specific sequence. In some embodiments, two or more different oligonucleotide probes are used, each comprising a different specific, known nucleotide sequence.

In some embodiments, the detection moiety is a polypeptide. The polypeptide can be detected using an immunological assay (e.g., an enzyme-linked immunosorbent assay (ELISA); a radioimmunoassay (RIA); etc.), using an antibody specific for the polypeptide detection moiety. The antibody specific for the polypeptide detection moiety can comprise a detectable label. The immunological assay can be carried out on a test strip (e.g., in a lateral flow assay) or other suitable medium such as a multi-well plate.

In some embodiments, the detection moiety is a fluorescent protein, where suitable fluorescent proteins are as described herein. In other embodiments, the detection moiety is luciferin or other substrate for luciferase. Suitable luciferins or other luciferase substrates include, e.g., luciferin (e.g., a firefly luciferin); an aminoluciferin; coelenterazine; a modified coelenterazine as described in U.S. Pat. No. 7,537,912; a coelenterazine analog as described in U.S. Patent Publication No. 2009/0081129 (e.g., a membrane permeant coelenterazine analog as described in U.S. Patent Publication No. 2009/0081129, e.g., one of Structures II, III, IV, V, and VI of U.S. Patent Publication No. 2009/0081129); aminoluciferin; dihydroluciferin; luciferin 6' methylether; or luciferin 6' chloroethylether. See, e.g., Branchini, B. R. et al. *Anal. Biochem.* 2010, 396, 290-296; and Mezzanotte, L. et al., In vivo bioluminescence imaging of murine xenograft cancer models with a red-shifted thermostable luciferase. *Mol. Imaging Biol.* (2009, Nov. 9, online; PubMed ID: 19937390).

Figure 18:
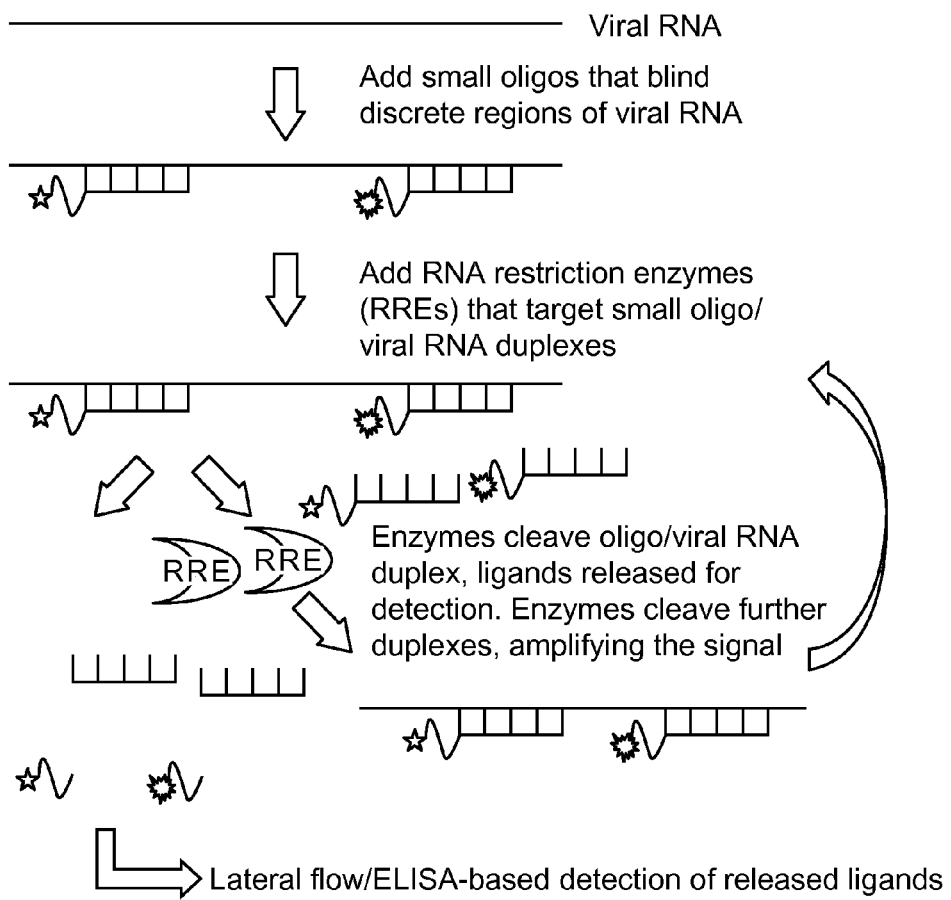
FIG. 18 depicts an example of a method for detecting a specific sequence in a target polyribonucleotide.

A non-limiting example of a subject detection method is illustrated schematically in FIG. 18. In the example depicted in FIG. 18, small oligonucleotides that bind discrete regions of a target polynucleotide (e.g., a viral RNA) are contacted with the target polynucleotide, where the oligonucleotides comprise detectable moieties (e.g., ligands; peptides; etc.). An enzymatically active, sequence-specific restriction endonuclease (RRE) that targets the oligonucleotide/viral RNA duplex is added. The enzyme cleaves the oligonucleotide/viral RNA duplex; and ligands are released for detection. The enzyme cleaves further duplexes, thereby amplifying the signal. Released ligands are detected using a lateral flow (e.g., test strip) or an immunological based assay (e.g., ELISA).

Endoribonucleases suitable for use in a subject method include an enzymatically active sequence-specific endoribonuclease (e.g., a Cas6 polypeptide or a Cas5 polypeptide).

Suitable Cas6 polypeptide amino acid sequences are provided in, e.g., GenBank Accession No. YP_143344 (*Thermus thermophilus* HB8); GenBank Accession No.

YP_145470 (*Thermus thermophilus* HB8); GenBank Accession No. YP_005869 (*Thermus thermophilus* HB27); GenBank Accession No. YP_006059433 (*Thermus thermophilus* JL-18); GenBank Accession No. YP_005654445 (*Thermus* sp. CCB_US3_UF1); GenBank Accession No. ZP_03497188 (*Thermus aquaticus*); GenBank Accession No. YP_003684129 (*Meiothermus silvanus* DSM 9946); GenBank Accession No. YP_004367049 (*Marinithermus hydrothermalis*); GenBank Accession No. YP_005641609 (*Thermus thermophilus* SG0.5JP17-16); GenBank Accession No. YP_006185 (*Thermus thermophilus* HB27); GenBank Accession No. YP_006059769 (*Thermus thermophilus* JL-18); YP_003506022 *Meiothermus ruber* DSM 1279).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIGS. 9A and 9B (SEQ ID NOs: 16-23).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, from about 225 amino acids to about 250 amino acids, or from about 250 amino acids to 264 amino acids, of an amino acid sequence depicted in FIG. 10 (SEQ ID NOs: 24-27).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids (aa) to about 175 amino acids, from about 175 amino acids to about 200 amino acids, from about 200 amino acids to about 225 amino acids, from about 225 amino acids to about 240 amino acids (e.g., 239 aa, 240 aa, 241 aa, 242 aa, 243 aa, 244 aa), from about 240 amino acids to about 250 amino acids, from about 250 amino acids to about 260 amino acids (e.g., 264 amino acids), from about 260 amino acids to about 275 amino acids (e.g., 277 amino acids), or from about 275 amino acids to 314 amino acids, of an amino acid sequence depicted in FIGS. 11A-F or FIG. 12 (SEQ ID NOs: 19, 24, 31, 33, 35, 37, and 39).

In some cases, the substrate recognized by a Cas6 polypeptide comprises a nucleotide sequence having at least about 80%, at least about 85%, at least about 90%, at least about 95%, at least about 98%, at least about 99%, or 100%, nucleotide sequence identity to one of the following sequences:

```
                                            (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';
and (SEQ ID NO: 7)
5'-GUUCCAAUUAAUCUUAAACCCUAUUAGGGAUUGAAAC-3'.
```

In some cases, the substrate recognized by a Cas6 polypeptide comprises one of the following sequences:

```
                                            (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';

(SEQ ID NO: 7)
5'-GUUCCAAUUAAUCUUAAACCCUAUUAGGGAUUGAAAC-3',
``` or a "minimal" sequence depicted in FIGS. 11A-F (SEQ ID NOs: 28-29, 30, 32, 34, 36, and 38).

An RNA substrate recognized by a Cas6 polypeptide can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

Suitable Cas5 polypeptides are provided in, e.g., GenBank Accession No. YP_009170 (*Desulfovibrio vulgaris* Cas5); GenBank Accession No. YP_004513910 (*Methylomonas methanica* MC09 Cas5); GenBank Accession No. YP_004496339 (*Desulfotomaculum carboxydivorans* Cas5); GenBank Accession No. ZP_05883174 (*Vibrio metchnikovii* Cas5); GenBank Accession No. YP_001174211 (*Pseudomonas stutzeri* Cas5); etc.

In some embodiments, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIG. 15 (SEQ ID NOs: 13 and 41-45), or in FIGS. 16A-E (SEQ ID NOs: 13 and 46-49).

In some cases, the substrate recognized by a variant Cas5 polypeptide comprises one of the following sequences:

```
                                        (SEQ ID NO: 8)
5'-GUCGCCCCCACGCGGGGGCGUGGAUUGAAAC-3';

(SEQ ID NO: 9)
5'-CCAGCCGCCUUCGGGCGGCUGUGUGUUGAAAC-3';

(SEQ ID NO: 10)
5'-GUCGCACUCUACAUGAGUGCGUGGAUUGAAAU-3';

(SEQ ID NO: 11)
5'-UGUCGCACCUUAUAUAGGUGCGUGGAUUGAAAU-3';
and (SEQ ID NO: 12)
5'-GUCGCGCCCCGCAUGGGGCGCGUGGAUUGAAA-3',
``` or a "minimal" sequence depicted in FIGS. 16A-E (SEQ ID NOs: 8-12).

An RNA substrate recognized by a Cas5 polypeptide can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

The target polyribonucleotide to be detected can be present in a sample, e.g., a biological sample such as blood, a blood product (e.g., plasma), urine, cerebrospinal fluid, bronchoalveolar lavage fluid, saliva, a tissue, cells, etc. The target polyribonucleotide can be isolated or purified. The target polyribonucleotide can be a messenger RNA (mRNA), a viral RNA, bacterial RNA, parasite RNA, or other RNA species. Viral RNAs include, but are not limited to, any member of the Flaviviridae, e.g., hepatitis C virus, Dengue virus, Yellow Fever Virus, West Nile Virus, etc.; any member of Retroviridae; an immunodeficiency virus (e.g., human immunodeficiency virus); etc.

The target polyribonucleotide to be detected can be present in a cell of a multicellular organism (or can be obtained from a cell of a multicellular organism).

The target polyribonucleotide to be detected can be present in or obtained from a cell or organism of any of the six kingdoms, e.g., Bacteria (e.g., Eubacteria); Archaebacteria; Protista; Fungi; Plantae; and Animalia. Suitable sources of target polyribonucleotides include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g, Apicomplexa, Myxozoa, Microsporidia), and ciliates (e.g., Paramecium). Suitable sources of target polyribonucleotides include members of the kingdom Fungi, including, but not limited to, members of any of the phyla: Basidiomycota (club fungi; e.g., members of Agaricus, Amanita, Boletus, Cantherellus, etc.); Ascomycota (sac fungi, including, e.g., *Saccharomyces*); Mycophycophyta (lichens); Zygomycota (conjugation fungi); and Deuteromycota. Suitable sources of target polyribonucleotides include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sources of target polyribonucleotides include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms); Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, hill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichtyces (cartilaginous fish), Actinopterygii (ray-finned fish), Actinista (coelocanths), Dipnoi (lungfish), Reptilia (reptiles, e.g., snakes, alligators, crocodiles, lizards, etc.), Ayes (birds); and Mammalian (mammals). Suitable plants include any monocotyledon and any dicotyledon.

Thus, e.g., a target polyribonucleotide can be present in or obtained from cells from organisms that include, but are not limited to, a protozoan, a plant, a fungus, an algal cell, a yeast cell, a reptile, an amphibian, a mammal, a marine microorganism, a marine invertebrate, an arthropod, an isopod, an insect, an arachnid, an archaebacterium, and a eubacterium.

A target polyribonucleotide can be present in or obtained from a non-human embryo, e.g., a *Drosophila* embryo; a zebrafish embryo; a mouse embryo; etc.

A target polyribonucleotide can be present in or obtained from a stem cell, e.g., an in vitro stem cell; a non-human stem cell; etc. Suitable stem cells include embryonic stem cells, adult stem cells, and induced pluripotent stem (iPS) cells.

In some embodiments, target polyribonucleotide will be isolated from a tissue taken from an organism; from a particular cell or group of cells isolated from an organism; etc. For example, where the organism is a plant, the target polyribonucleotide will in some embodiments be isolated from the xylem, the phloem, the cambium layer, leaves, roots, etc. Where the organism is an animal, the target polyribonucleotide will in some embodiments be isolated from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

Methods of Regulating Production of a Target RNA

The present disclosure provides a method of regulating production of a target RNA in a cell. The method generally involves contacting a genetically modified host cell with an agent that activates an inducible promoter, where the genetically modified host cell is genetically modified with a recombinant expression vector comprising a nucleotide sequence encoding an enzyme that catalyzes cleavage at a sequence-specific cleavage site in a substrate polyribonucleotide, where the enzyme-encoding nucleotide sequence is operably linked to the inducible promoter, and where, upon activation of the inducible promoter, the enzyme is produced in the cell and cleaves said target RNA from a precursor RNA.

Figure 20:
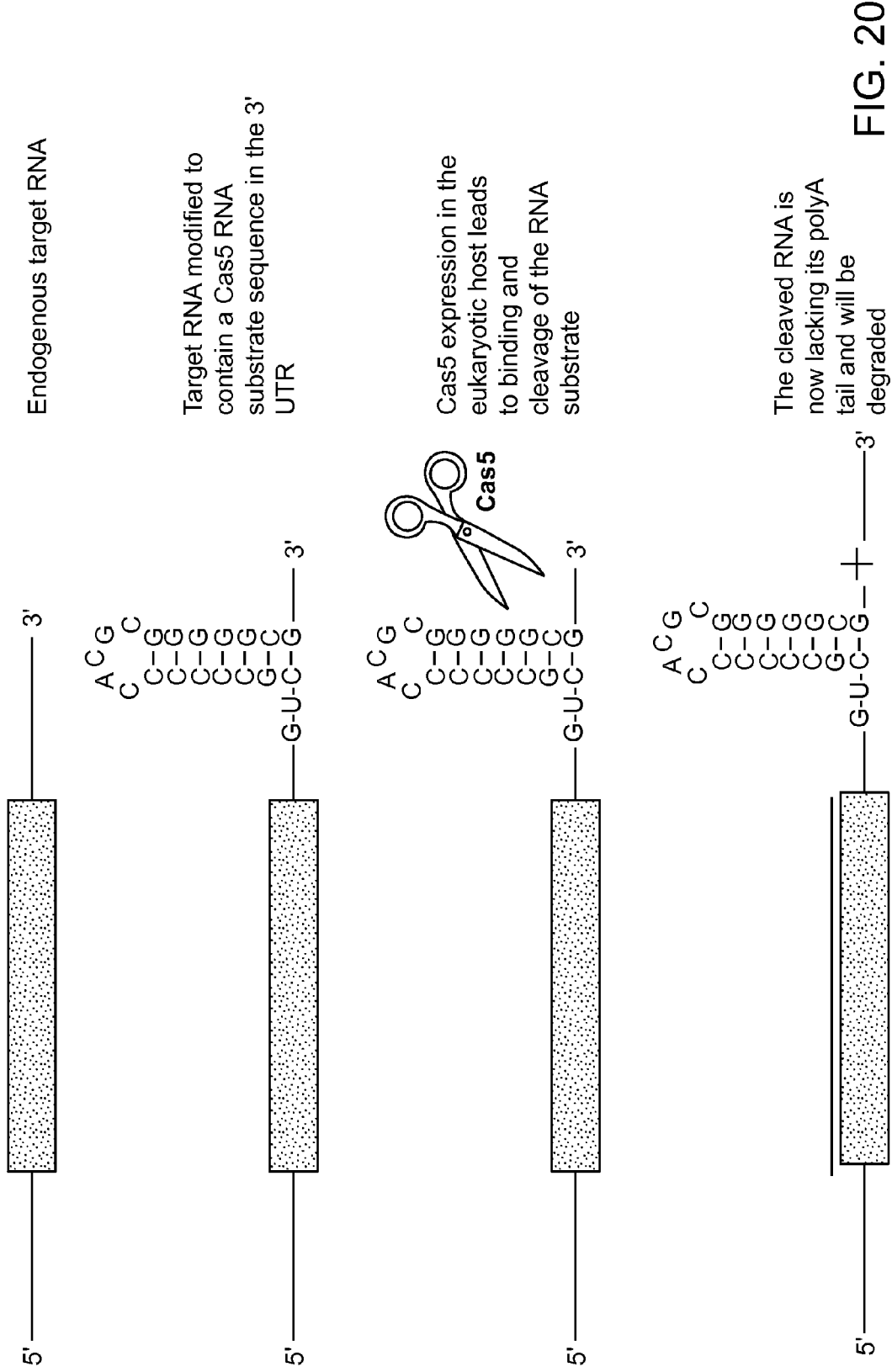
FIG. 20 depicts an exemplary method of regulating expression of a target RNA in a eukaryotic cell. A Cas5 RNA substrate sequence is shown. (SEQ ID NO: 52).

FIG. 20 provides a schematic depiction of an exemplary method of regulating production of a target RNA. In FIG. 20, an endogenous target RNA is modified to include a Cas5 RNA substrate in the 3' untranslated region (3' UTR). Cas5 expression in the host cell leads to binding and cleavage of the RNA substrate. The cleaved RNA now lacks its polyA tail and will be degraded.

For example, in some embodiments, the present disclosure provides a method of regulating production of a target RNA in a eukaryotic cell, where the method involves contacting a genetically modified host cell with an agent that activates an inducible promoter, where the genetically modified host cell is genetically modified with a recombinant expression vector comprising a nucleotide sequence encoding an enzymatically active sequence-specific Cas5 endoribonuclease or a Cas6 endoribonuclease that catalyzes cleavage at a sequence-specific cleavage site in a substrate polyribonucleotide, where the enzyme-encoding nucleotide sequence is operably linked to the inducible promoter, and where, upon activation of the inducible promoter, the enzyme is produced in the cell and cleaves said target RNA from a precursor RNA. In some cases, the target RNA species is a regulatory RNA. In some cases, cleavage of said target RNA from a precursor RNA inactivates the precursor RNA.

Endoribonucleases suitable for use in a subject method include an enzymatically active sequence-specific endoribonuclease (e.g., a Cas6 polypeptide or a Cas5 polypeptide).

Suitable Cas6 polypeptide amino acid sequences are provided in, e.g., GenBank Accession No. YP_143344 (*Thermus thermophilus* HB8); GenBank Accession No. YP_145470 (*Thermus thermophilus* HB8); GenBank Accession No. YP_005869 (*Thermus thermophilus* HB27); GenBank Accession No. YP_006059433 (*Thermus thermophilus* JL-18); GenBank Accession No. YP_005654445 (*Thermus* sp. CCB_US3_UF1); GenBank Accession No. ZP_03497188 (*Thermus aquaticus*); GenBank Accession No. YP_003684129 (*Meiothermus silvanus* DSM 9946); GenBank Accession No. YP_004367049 (*Marinithermus hydrothermalis*); GenBank Accession No. YP_005641609 (*Thermus thermophilus* SG0.5JP17-16); GenBank Accession No. YP_006185 (*Thermus thermophilus* HB27); GenBank Accession No. YP_006059769 (*Thermus thermophilus* JL-18); YP_003506022 *Meiothermus ruber* DSM 1279).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIGS. 9A and 9B (SEQ ID NOs: 16-23).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, from about 225 amino acids to about 250 amino acids, or from about 250 amino acids to 264 amino acids, of an amino acid sequence depicted in FIG. 10 (SEQ ID NOs: 24-27).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids (aa) to about 175 amino acids, from about 175 amino acids to about 200 amino acids, from about 200 amino acids to about 225 amino acids, from about 225 amino acids to about 240 amino acids (e.g., 239 aa, 240 aa, 241 aa, 242 aa, 243 aa, 244 aa), from about 240 amino acids to about 250 amino acids, from about 250 amino acids to about 260 amino acids (e.g., 264 amino acids), from about 260 amino acids to about 275 amino acids (e.g., 277 amino acids), or from about 275 amino acids to 314 amino acids, of an amino acid sequence depicted in FIGS. 11A-F or FIG. 12 (SEQ ID NOs: 19, 24, 31, 33, 35, 37, and 39).

Suitable Cas5 polypeptides are provided in, e.g., GenBank Accession No. YP_009170 (*Desulfovibrio vulgaris* Cas5); GenBank Accession No. YP_004513910 (*Methylomonas methanica* MC09 Cas5); GenBank Accession No. YP_004496339 (*Desulfotomaculum carboxydivorans* Cas5); GenBank Accession No. ZP_05883174 (*Vibrio metchnikovii* Cas5); GenBank Accession No. YP_001174211 (*Pseudomonas stutzeri* Cas5); etc.

In some embodiments, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIG. 15 (SEQ ID NOs: 13 and 41-45), or in FIGS. 16A-E (SEQ ID NOs: 13 and 46-49).

A suitable inducible promoter can include a promoter that is functional in a eukaryotic cell. Suitable inducible promoters are known in the art. For example, suitable inducible promoters include, but are not limited to, a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1. Suitable inducible promoters include tetracycline-inducible promoters; a metallothionein promoter; tetracycline-inducible promoters, methionine-inducible promoters; and galactose-inducible promoters, which promoters are all well known in the art. Other suitable promoters include the ADH2 alcohol dehydrogenase promoter (repressed in glucose, induced when glucose is exhausted and ethanol is made) and the CUP1 metallothionein promoter (induced in the presence of $Cu^{2+}$, $Zn^{2+}$).

Agents that induce any given inducible promoter are known in art. For example, tetracycline-regulatable promoters can be regulated by tetracycline or doxycycline; carbohydrates can be used to induce a carbohydrate-inducible promoter (e.g., galactose for a galactose-inducible promoter); methionine can be used to induce a methionine-inducible promoter; metals can be used to induce a metallothionein promoter.

The target RNA can be a regulatory RNA. Regulator RNAs are well known in the art and include, e.g., microRNAs, short hairpin RNAs (shRNAs), and the like.

In some embodiments, cleavage of the target RNA from a precursor RNA inactivates the precursor RNA.

The genetically modified host cell can be an in vitro cell, e.g., a prokaryotic cell, or a eukaryotic cell (e.g., a mammalian cell, including primary cells, transformed cell lines, and the like). The genetically modified host cell can be an in vivo cell. In some embodiments, the in vivo cell is a non-human cell.

The genetically modified host cell can be a cell of a multicellular organism (or can be obtained from a cell of a multicellular organism).

The genetically modified host cell can be a cell obtained from or present in an organism of any of the six kingdoms, e.g., Bacteria (e.g., Eubacteria); Archaebacteria; Protista; Fungi; Plantae; and Animalia. Suitable organisms include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g, Apicomplexa, Myxozoa, Microsporidia), and ciliates (e.g., Paramecium). Suitable organisms include members of the kingdom Fungi, including, but not limited to, members of any of the phyla: Basidiomycota (club fungi; e.g., members of Agaricus, Amanita, Boletus, Cantherellus, etc.); Ascomycota (sac fungi, including, e.g., *Saccharomyces*); Mycophycophyta (lichens); Zygomycota (conjugation fungi); and Deuteromycota. Suitable organisms include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable organisms include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms); Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Ayes (birds); and Mammalian (mammals). Suitable plants include any monocotyledon and any dicotyledon.

Thus, e.g., a genetically modified host cell can be a cell obtained from or present in a protozoan, a plant, a fungus, an algal cell, a yeast, a reptile, an amphibian, a mammal, a marine microorganism, a marine invertebrate, an arthropod, an isopod, an insect, an arachnid, an archaebacterium, and a eubacterium.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

The genetically modified host cell can be a cell obtained from or present in a non-human embryo, e.g., a *Drosophila* embryo; a zebrafish embryo; a mouse embryo; etc.

The genetically modified host cell can be a stem cell, e.g., an in vitro stem cell; a non-human stem cell; etc. Suitable stem cells include embryonic stem cells, adult stem cells, and induced pluripotent stem (iPS) cells.

Methods of Isolating a Target Nucleic Acid

Figure 19:
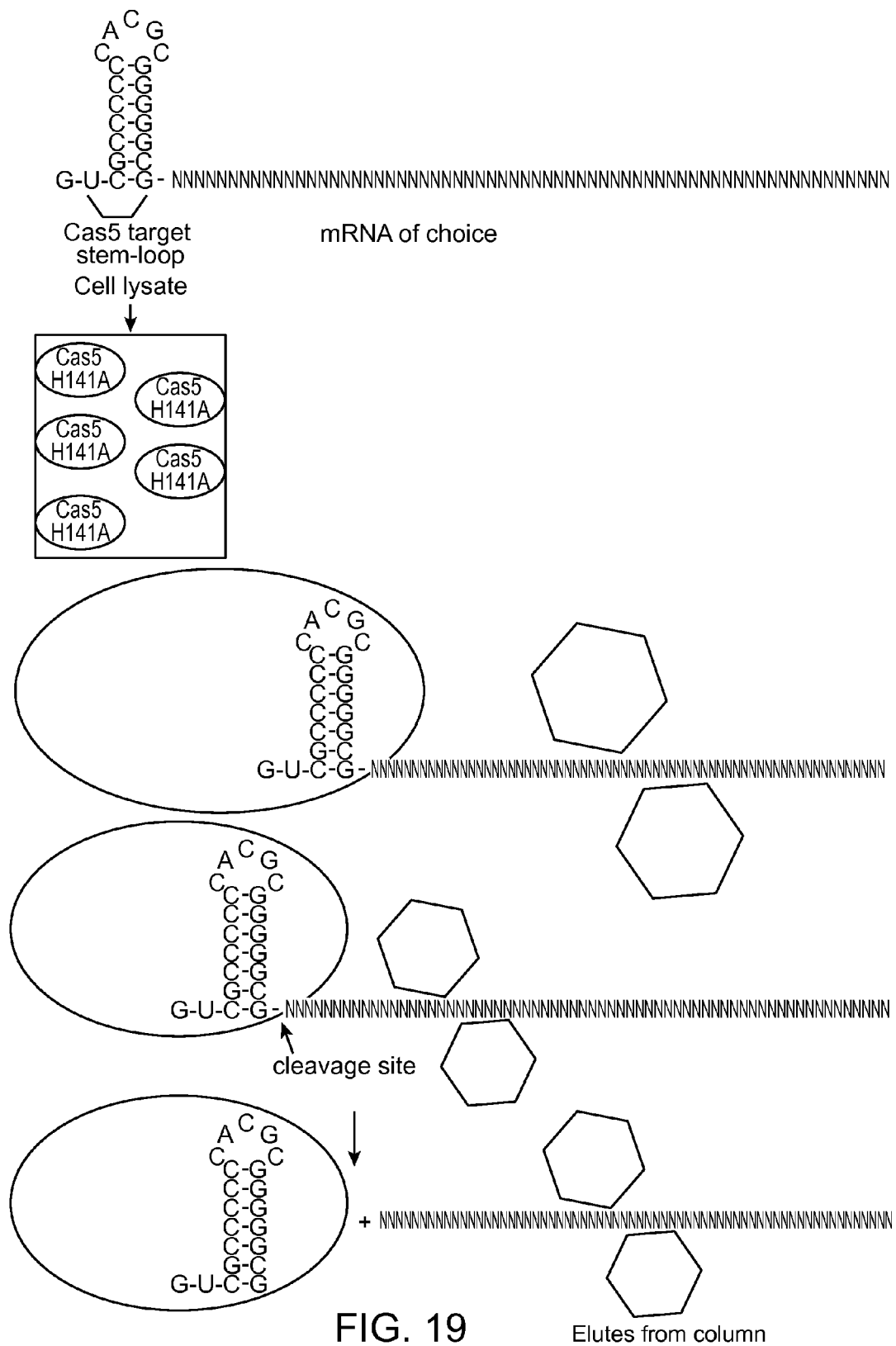
FIG. 19 depicts an exemplary method of isolating a target RNA. A Cas5 target stem-loop is shown. (SEQ ID NO: 51).

The present disclosure provides methods of isolating a target nucleic acid from a mixed population of nucleic acids. The methods generally involve: a) contacting a mixed population of nucleic acids with an immobilized sequence-specific, enzymatically inactive endoribonuclease, wherein the mixed population of nucleic acids includes a target nucleic acid comprising a "tag" (or "recognition") nucleotide sequence that is specifically bound by the immobilized sequence-specific, enzymatically inactive endoribonuclease, such that the target nucleic acid comprising the tag nucleotide sequence ("tagged target nucleic acid") binds to the immobilized sequence-specific, enzymatically inactive endoribonuclease, forming a tagged target nucleic acid/immobilized sequence-specific enzymatically active endoribonuclease complex, wherein the contacting step takes place in a liquid solution (a "binding solution"); and b) adding imidazole to the liquid solution to a final concentration of from about 100 mM to about 500 mM (e.g., from about 100 mM to about 150 mM, from about 150 mM to about 200 mM, from about 200 mM to about 250 mM, from about 250 mM to about 300 mM, from about 300 mM to about 350 mM, from about 350 mM to about 400 mM, from about 400 mM to about 450 mM, or from about 450 mM to about 500 mM), thereby forming a reactivation solution that enzymatically reactivates the enzymatically inactive endoribonuclease such that the endoribonuclease becomes enzymatically active and cleaves the target nucleic acid from the "tag" nucleotide sequence, thereby releasing the target nucleic acid. FIG. 19 is a schematic representation of an exemplary embodiment of a subject method for isolating a target RNA.

The method can further include one or more washing steps. For example, after step (a) and before step (b), the immobilized sequence-specific, enzymatically inactive endoribonuclease that comprises a bound target nucleic acid comprising a "tag" nucleotide sequence can be washed one or more times with the binding solution, such that the target nucleic acid remains bound to the sequence-specific, enzymatically inactive endoribonuclease, and any unbound nucleic acids are washed away.

The mixed population of nucleic acids can include RNA and DNA. The target nucleic acid is an RNA that comprises a "tag" or "recognition" nucleotide sequence that is specifically bound by the sequence-specific endoribonuclease. In its enzymatically inactive state ("uninduced" state), the endoribonuclease can bind, but cannot cleave, the tagged target RNA. In its enzymatically active state ("induced" state) (e.g., in the presence of imidazole in a concentration of from about 100 mM to about 500 mM), the endoribonuclease can both bind and cleave the recognition nucleotide sequence in the tagged target nucleic acid, thereby releasing the target nucleic acid from the tag.

The binding solution can include a buffer and a salt; and lacks imidazole. The reactivation solution can include imidazole in a final concentration of from about 100 mM to about 500 mM, e.g., from about 100 mM to about 150 mM, from about 150 mM to about 200 mM, from about 250 mM to about 350 mM, from about 350 mM to about 400 mM, or from about 400 mM to about 500 mM. The presence of imidazole reactivates the sequence-specific, enzymatically inactive endoribonuclease such that the endoribonuclease becomes enzymatically active, e.g., the endoribonuclease exhibits at least about 50%, at least about 60%, at least about 70%, at least about 80%, at least about 90%, at least about 95%, or more than 95%, of wild-type sequence-specific endoribonuclease (e.g., an amino acid sequence as depicted in any of FIGS. 9, 10, 11, 12, 15, and 16).

Endoribonucleases suitable for use in a subject method include an enzymatically active sequence-specific endoribonuclease (e.g., a Cas6 polypeptide or a Cas5 polypeptide).

Suitable Cas6 polypeptide amino acid sequences that can be modified to be enzymatically in active are provided in, e.g., GenBank Accession No. YP_143344 (*Thermus thermophilus* HB8); GenBank Accession No. YP_145470 (*Thermus thermophilus* HB8); GenBank Accession No. YP_005869 (*Thermus thermophilus* HB27); GenBank Accession No. YP_006059433 (*Thermus thermophilus* JL-18); GenBank Accession No. YP_005654445 (*Thermus sp.* CCB_US3_UF1); GenBank Accession No. ZP_03497188 (*Thermus aquaticus*); GenBank Accession No. YP_003684129 (*Meiothermus silvanus* DSM 9946); GenBank Accession No. YP_004367049 (*Marinithermus hydrothermalis*); GenBank Accession No. YP_005641609 (*Thermus thermophilus* SG0.5JP17-16); GenBank Accession No. YP_006185 (*Thermus thermophilus* HB27); GenBank Accession No. YP_006059769 (*Thermus thermophilus* JL-18); YP_003506022 *Meiothermus ruber* DSM 1279).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIGS. 9A and 9B (SEQ ID NOs: 16-23).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, from about 225 amino acids to about 250 amino acids, or from about 250 amino acids to 264 amino acids, of an amino acid sequence depicted in FIG. 10 (SEQ ID NOs: 24-27).

In some cases, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids (aa) to about 175 amino acids, from about 175 amino acids to about 200 amino acids, from about 200 amino acids to about 225 amino acids, from about 225 amino acids to about 240 amino acids (e.g., 239 aa, 240 aa, 241 aa, 242 aa, 243 aa, 244 aa), from about 240 amino acids to about 250 amino acids, from about 250 amino acids to about 260 amino acids (e.g., 264 amino acids), from about 260 amino acids to about 275 amino acids (e.g., 277 amino acids), or from about 275 amino acids to 314 amino acids, of an amino acid sequence depicted in FIGS. 11A-F or FIG. 12 (SEQ ID NOs: 19, 24, 31, 33, 35, 37, and 39).

In some cases, the substrate (e.g., the "tag" or recognition sequence) recognized by a Cas6 polypeptide comprises a nucleotide sequence having at least about 80%, at least about 85%, at least about 90%, at least about 95%, at least about 98%, at least about 99%, or 100%, nucleotide sequence identity to one of the following sequences:

```
                                              (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';
and (SEQ ID NO: 7)
5'-GUUCCAAUUAAUCUUAAACCCUAUUAGGGAUUGAAAC-3'.
```

In some cases, the substrate (e.g., the "tag" or recognition sequence) recognized by a Cas6 polypeptide comprises one of the following sequences:

```
                                              (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';

(SEQ ID NO: 7)
5'-GUUCCAAUUAAUCUUAAACCCUAUUAGGGAUUGAAAC-3',
``` or a "minimal" sequence depicted in FIGS. 11A-F (SEQ ID NOs: 28-29, 30, 32, 34, 36, and 38).

An RNA substrate recognized by a Cas6 polypeptide can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

Suitable Cas5 polypeptides are provided in, e.g., GenBank Accession No. YP_009170 (*Desulfovibrio vulgaris* Cas5); GenBank Accession No. YP_004513910 (*Methylomonas methanica* MC09 Cas5); GenBank Accession No. YP_004496339 (*Desulfotomaculum carboxydivorans* Cas5); GenBank Accession No. ZP_05883174 (*Vibrio metchnikovii* Cas5); GenBank Accession No. YP_001174211 (*Pseudomonas stutzeri* Cas5); etc.

In some embodiments, an enzymatically active, sequence-specific endoribonuclease comprises an amino acid sequence having at least about 55%, at least about 60%, at least about 65%, at least about 70%, at least about 75%, at least about 80%, at least about 85%, at least about 90%, at least about 95%, at least about 98%, at least about 99%, or 100%, amino acid sequence identity with a contiguous stretch of from about 150 amino acids to about 175 amino acids, from about 175 amino acids to about 200 amino acids, from about 200 amino acids to about 225 amino acids, or from about 225 amino acids to the full length (e.g., 235 amino acids, 236 amino acids, 237 amino acids, 238 amino acids, 239 amino acids, 247 amino acids, 251 amino acids, 262 amino acids, or 267 amino acids) of an amino acid sequence depicted in FIG. 15 (SEQ ID NOs: 13 and 41-45), or in FIGS. 16A-E (SEQ ID NOs: 13 and 46-49).

In some cases, the substrate (e.g., the "tag" or recognition sequence) recognized by a Cas5 polypeptide comprises a nucleotide sequence having at least about 80%, at least about 85%, at least about 90%, at least about 95%, at least about 98%, at least about 99%, or 100%, nucleotide sequence identity to one of the following sequences:

```
                                              (SEQ ID NO: 8)
5'-GUCGCCCCCACGCGGGGGCGUGGAUUGAAAC-3';

(SEQ ID NO: 9)
5'-CCAGCCGCCUUCGGGCGGCUGUGUGUUGAAAC-3';

(SEQ ID NO: 10)
5'-GUCGCACUCUACAUGAGUGCGUGGAUUGAAAU-3';

(SEQ ID NO: 11)
5'-UGUCGCACCUUAUAUAGGUGCGUGGAUUGAAAU-3';
and (SEQ ID NO: 12)
5'-GUCGCGCCCCGCAUGGGGCGCGUGGAUUGAAA-3',
``` or a "minimal" sequence depicted in FIGS. 16A-E (SEQ ID NOs: 8-12).

In some cases, the substrate (e.g., the "tag" or recognition sequence) recognized by a Cas5 polypeptide comprises one of the following sequences:

```
                                              (SEQ ID NO: 8)
5'-GUCGCCCCCACGCGGGGGCGUGGAUUGAAAC-3';

(SEQ ID NO: 9)
5'-CCAGCCGCCUUCGGGCGGCUGUGUGUUGAAAC-3';

(SEQ ID NO: 10)
5'-GUCGCACUCUACAUGAGUGCGUGGAUUGAAAU-3';

(SEQ ID NO: 11)
5'-UGUCGCACCUUAUAUAGGUGCGUGGAUUGAAAU-3';
and (SEQ ID NO: 12)
5'-GUCGCGCCCCGCAUGGGGCGCGUGGAUUGAAA-3',
``` or a "minimal" sequence depicted in FIGS. 16A-E (SEQ ID NOs: 8-12).

An RNA substrate recognized by a variant Cas5 polypeptide of the present disclosure can have a length of from about 15 nucleotides (nt) to about 20 nt (e.g., 15 nt, 16 nt, 17 nt, 18 nt, 19 nt, or 20 nt), from about 20 nt to about 25 nt (e.g., 20 nt, 21 nt, 22 nt, 23 nt, 24 nt, or 25 nt), from about 25 nt to about 30 nt (e.g., 25 nt, 26 nt, 27 nt, 28 nt, 29 nt, or 30 nt), from about 30 nt to about 35 nt (e.g., 30 nt, 31 nt, 32 nt, 33 nt, 34 nt, or 35 nt), from about 35 nt to about 40 nt, from about 40 nt to about 50 nt, or more than 50 nt.

The "tag" or "recognition" nucleotide sequence can be introduced into a nucleic acid using standard recombinant methods. Thus, the tagged target nucleic acid will include a tag that is enzymatically cleaved, thereby releasing the target nucleic acid.

In some embodiments, the tagged target nucleic acid (RNA) will have one or more polypeptides bound thereto. A tagged target RNA that has one or more polypeptides bound thereto is referred to herein as a RNA protein complex. Thus, in some embodiments, the target RNA that is isolated using a subject method is an RNA protein complex. In some embodiments, a subject method can further comprise analyzing the polypeptide(s) bound to the isolated target RNA.

A subject method provides for isolation of a target RNA (or RNA protein complex). In some embodiments, a subject method provides for purification of a target RNA (or RNA protein complex) such that the target RNA (or RNA protein complex) is at least about 50% pure, at least about 60% pure, at least about 70% pure, at least about 80% pure, at least about 90% pure, at least about 95% pure, at least about 98% pure, or greater than 98% pure.

In some embodiments, a protein bound to a target RNA in a target RNA/protein complex can be eluted from the RNA/protein complex. The eluted protein can be further characterized, e.g., by sequencing, enzymatic digestion, a functional assay, etc.

The mixed population of nucleic acids can be present in a cell lysate. For example, an expression vector comprising a nucleotide sequence encoding a tagged target RNA is introduced into a cell (e.g., in vitro or in vivo), such that the cell synthesizes the tagged target RNA. A lysate is made from the cell and the lysate (optionally subjected to one or more steps to enrich for nucleic acids) is applied to the immobilized sequence-specific enzymatically-inactive endoribonuclease.

The sequence-specific enzymatically-inactive endoribonuclease can be immobilized on any of a variety of insoluble support. Suitable insoluble supports include, but are not limited to agarose beads, magnetic beads, a test strip, a multi-well dish, and the like. The insoluble support can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

The present disclosure also provides a method of isolating a polypeptide that binds a target RNA, where the method comprises: a) contacting an immobilized complex with a liquid solution comprising a polypeptide that binds the target RNA, where the immobilized complex comprises the variant Cas5 endoribonuclease or the variant Cas6 endoribonuclease and a tagged target RNA comprising a recognition nucleotide sequence that is specifically bound by the variant Cas5 or Cas6 endoribonuclease, where said contacting results in binding of the polypeptide to the target RNA, where said contacting is carried out in a binding solution lacking imidazole; and b) eluting the bound polypeptide.

Kits

The present disclosure also provides kits for determining the nucleotide sequence of a target polyribonucleotide. The present disclosure provides kits for carrying out sequence-specific cleavage of a substrate polyribonucleotide. The present disclosure provides kits for carrying out detection of an RNA sequence in a target polyribonucleotide. The present disclosure provides kits for carrying out isolation of a target RNA. The present disclosure provides kits for carrying out isolation of a polypeptide that binds a target RNA.

Kits for Carrying Out Direct Sequencing of a Polyribonucleotide

A subject kit for carrying out direct sequencing of a polyribonucleotide includes at least a subject sequence-specific, enzymatically inactive endoribonuclease, where the sequence-specific, enzymatically inactive endoribonuclease is purified. In some embodiments, the enzymatically inactive, sequence-specific endoribonuclease is linked to an acceptor molecule or a donor molecule, for FRET detection.

A subject kit for carrying out direct sequencing of a polyribonucleotide includes at least a subject sequence-specific, enzymatically inactive endoribonuclease; and can include one or more additional components, where the one or more additional components can be: 1) a buffer; 2) a probe oligonucleotide comprising a defined sequence; 3) a probe oligonucleotide comprising a defined sequence, where the probe oligonucleotide is linked to an acceptor molecule or a donor molecule, for FRET detection; 4) an insoluble support, for linking to a target polyribonucleotide; 5) a positive control polyribonucleotide, where the positive control polyribonucleotide comprises a known nucleotide sequence; 6) a positive control probe oligonucleotide that binds to and forms a duplex with the known sequence of the positive control polyribonucleotide.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Kits for Carrying Out Sequence-Specific Cleavage of a Substrate Polyribonucleotide A subject kit for carrying out sequence-specific cleavage of a substrate polyribonucleotide includes at least a purified sequence-specific endoribonuclease and/or a nucleic acid comprising a nucleotide sequence encoding the sequence-specific endoribonuclease. A subject kit for carrying out sequence-specific cleavage of a substrate polyribonucleotide can include, in addition to a purified sequence-specific endoribonuclease (and/or a nucleic acid comprising a nucleotide sequence encoding the sequence-specific endoribonuclease), one or more additional components. Suitable additional components include, e.g., a buffer; a polyribonucleotide substrate that serves as a positive control; polyribonucleotide size standards; a negative control substrate; and the like. The components can each be in separate containers. The kit can further include one or more positive and negative controls.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Kits for Carrying Out Detection of a Sequence in a Target Polyribonucleotide

A subject kit for carrying out detection of a sequence in a target polyribonucleotide (e.g., for carrying out detection of a polyribonucleotide) can include an oligonucleotide probe comprising a known sequence. In some embodiments, the kit will include an oligonucleotide probe comprising a known sequence and comprising a detectable moiety, e.g., a polypeptide that can be detected using an immunological assay; a fluorescent protein; a luciferin; etc. The kit can further include a positive control polyribonucleotide that comprises a nucleotide sequence capable of forming a duplex with the oligonucleotide probe. The kit can further include an enzymatically active, sequence-specific endoribonuclease that specifically detects and cleaves a duplex formed by the oligonucleotide probe and a target polyribonucleotide. The kit can further include one or more of a buffer; components for detecting the detectable moiety; a test strip; and the like. The kit can further include one or more positive and negative controls.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Kits for Carrying Out Isolation of a Target RNA

A subject kit for carrying out isolation (e.g., purification) of a target RNA can include one or more of: 1) a subject sequence-specific, enzymatically inactive endoribonuclease; 2) an expression construct comprising a "tag" nucleotide sequence, i.e., a nucleotide sequence that is specifically bound by the sequence-specific, enzymatically inactive endoribonuclease, where a nucleotide sequence encoding a target RNA of choice can be inserted 3' of the "tag" nucleotide sequence; and 3) imidazole. The sequence-specific, enzymatically inactive endoribonuclease can be immobilized on an insoluble support. The kit can further include a liquid composition for contacting a mixed population of nucleic acids with the immobilized sequence-specific, enzymatically inactive endoribonuclease. The kit can further include a wash buffer. The kit can further include one or more positive and negative controls. A positive control could include an expression vector comprising a nucleotide sequence encoding a tagged target RNA, where the tag is specifically bound by the sequence-specific, enzymatically inactive endoribonuclease. The components can each be in separate containers.

For example, a subject kit can include a subject sequence-specific, enzymatically inactive endoribonuclease. A subject kit can further include a recombinant expression vector comprising, in order from 5' to 3' and in operable linkage: a) a nucleotide sequence encoding an RNA substrate that is specifically bound by a subject variant Cas5 or Cas6 endoribonuclease; and b) a multiple cloning site suitable for insertion of a nucleic acid encoding the target RNA. The nucleotide sequence encoding the RNA substrate can be operably linked to a promoter. In some instances, the promoter is an inducible promoter. The RNA substrate can comprise a substrate nucleotide sequence, as described above. In some cases, the recombinant expression vector comprises, inserted into the multiple cloning site, a nucleotide sequence encoding the target RNA. The kit can further include a buffer that lacks imidazole. The kit can further include imidazole or an imidazole solution. The kit can further include one or more wash buffers. In some cases, the kit will include a positive control expression vector. The variant Cas5 or Cas6 endoribonuclease can be immobilized on an insoluble support, where suitable insoluble supports include, but are not limited to agarose beads, magnetic beads, a test strip, a multi-well dish, and the like. The insoluble support can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Generation and Characterization of Cas6 Mutants

Figure 2:
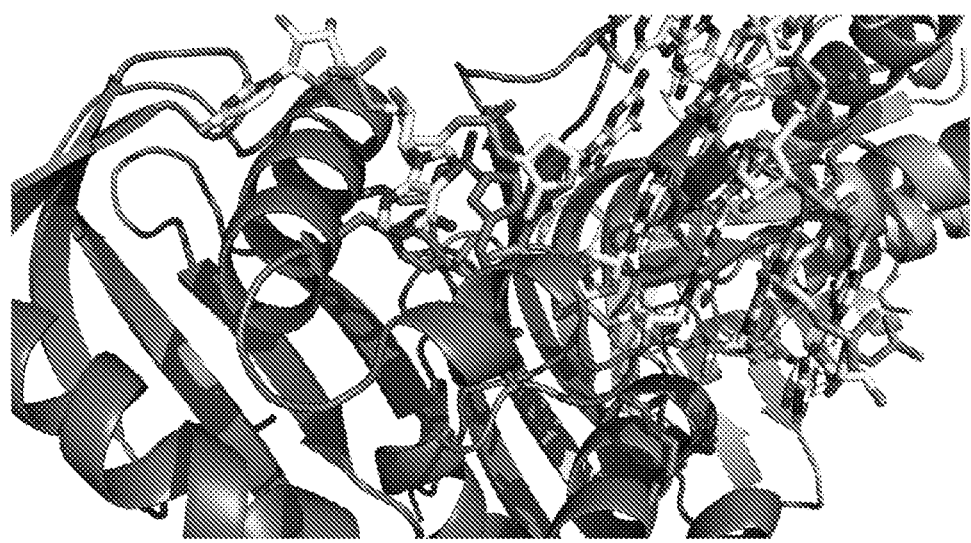
FIG. 2 depicts a close up of catalytic residue H37 in close proximity to the RNA backbone between G28 and A29.
Figure 3:
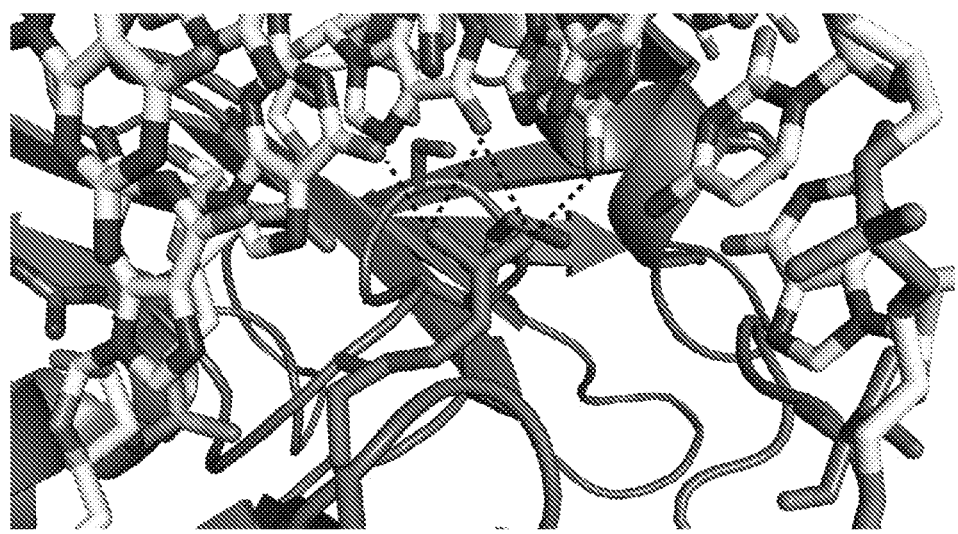
FIG. 3 depicts involvement of R129 in multiple base specific interactions with nucleotides G26, G27 and G28.
Figure 21:
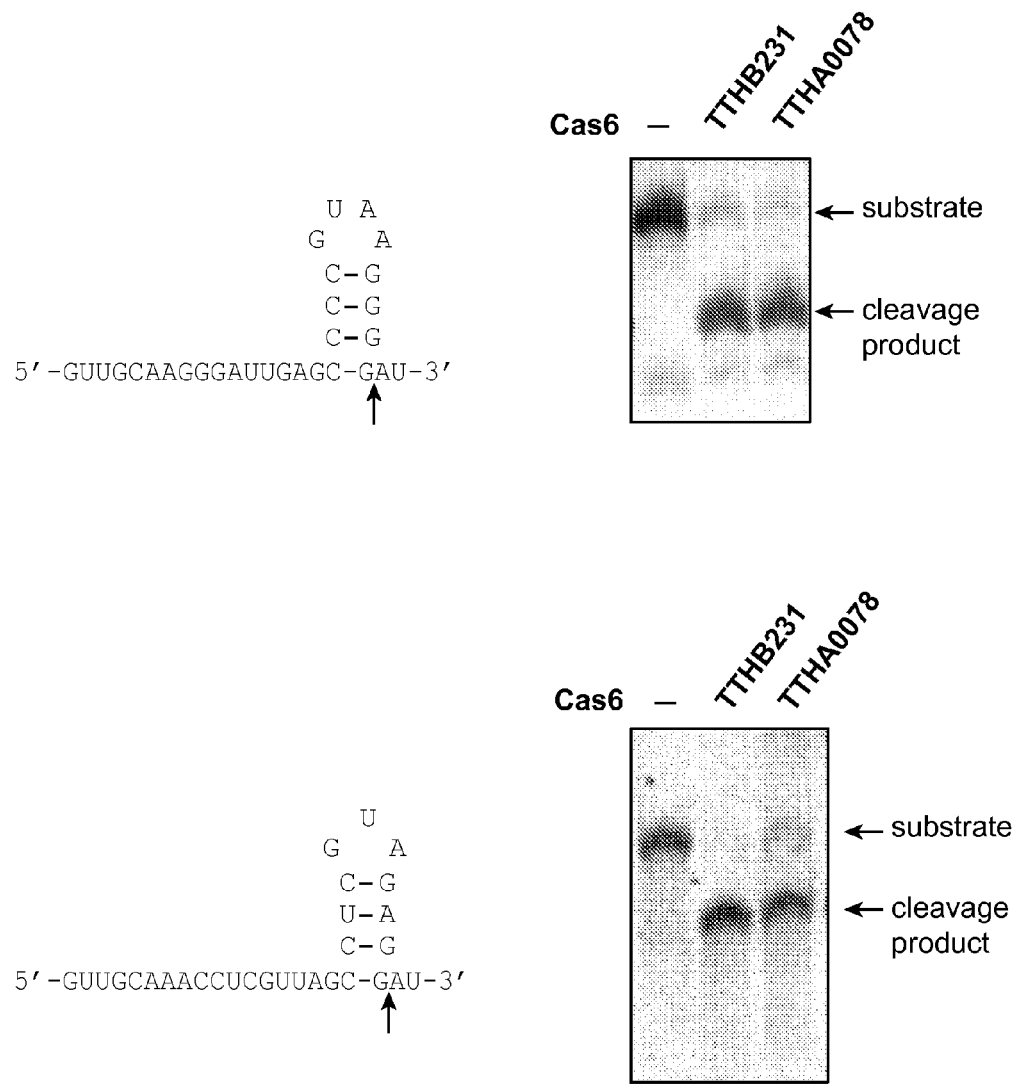
FIG. 21 depicts cleavage of target RNAs by *Thermus thermophilus* Cas6 proteins at a position immediately downstream of the stem loop structure. (Top to bottom: SEQ ID NOs: 53, 54).

Cas6 proteins TTHA0078 (TtCas6A) (SEQ ID NO: 19) and TTHB231(TtCas6B) (SEQ ID NO: 24) were characterized.
Crystal Structure of TTHA0078 with an RNA Substrate
Protein TTHA0078 was grown under the following conditions: 0.1 M Bis_Tris-Propane pH 6.5; 14-18% poly (ethylene glycol) (PEG) 3350; and 0.2 M Sodium Sulfate.
On the gel sizing column, the crystal consisted of two copies of the protein. FIG. 1 shows Cas6 protein TTHA0078 bound to nucleotides 15-30 of Tt_R1 containing a 2' deoxy at position G28. The putative catalytic residue H37 is highlighted in red. The unbound part of the homodimer does not show density for residues 32-40, which indicates that the loop becomes ordered only when it's bound to the substrate.
FIG. 2 provides a close-up of catalytic residue H37 in close proximity to the RNA backbone between G28 and A29. The RNA substrate contained a 2' deoxy at position G28 to avoid cleavage.
FIG. 3 depicts involvement of R129 of TTHA0078 in multiple base specific interactions with nucleotides G26, G27 and G28.
FIG. 21 shows cleavage of target RNAs by *Thermus thermophilus* Cas6 proteins at a position immediately downstream of the stem loop structure. Cleavage positions are indicated with a red arrow. Synthetic RNAs (1 microM) were incubated with recombinant Cas6 proteins (10 microM) in 150 mM KCl and 20 mM Hepes pH 7.5 at 65° C. for 5 min. Reaction products were isolated by phenol-chloroform extraction, resolved by electrophoresis on a 15% denaturing polyacrylamide gel, and visualized by staining with ethidium bromide.
Characterization of TTHA0078 and TTHB231 Binding Affinity
It was found that TTHA0078 and TTHB231 bind their substrates with different affinities and discriminate between targets; and that the stem and the 5' handle are both of major importance for binding of substrate.
Biochemical analyses were performed on TTHA0078 and TTHB231. TTHA0078 binds its substrates with affinities of ~60 pM (Tt_R1) and ~1.6 nM (Tt_R2) and therefore strongly favors binding of Tt_R1 over Tt_R2 while binding affinities of ~4 nM (Tt_R1) and ~15 nM (Tt_R2) indicate the opposite for TTHB231. Biochemical analysis focused on TTHA0078 and its interactions with Tt_R1. To determine the importance of the stem for Protein-RNA binding, a series of mutated RNAs, which had an A-U instead of a C-G at different positions of the 4 nt long stem, was created.

Figure 4:
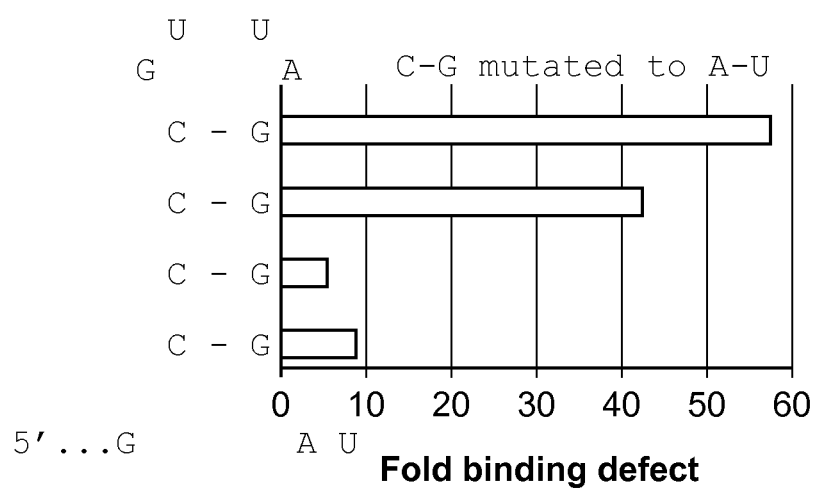
FIG. 4 depicts the impact of mutations at different parts of the stem of the RNA substrate on binding affinity of TTHA0078 to its substrate. (SEQ ID NO: 14).
Figure 5:
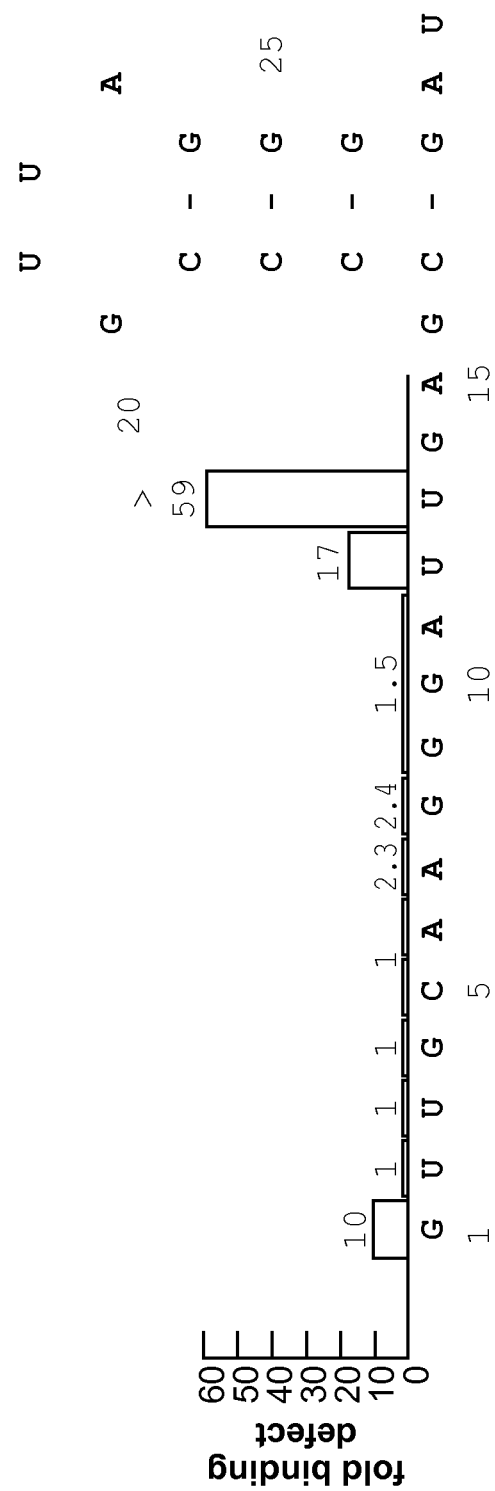
FIG. 5 depicts the effect of RNA substrate length on binding affinity to TTHA0078. (SEQ ID NO: 15).
Figure 6A:
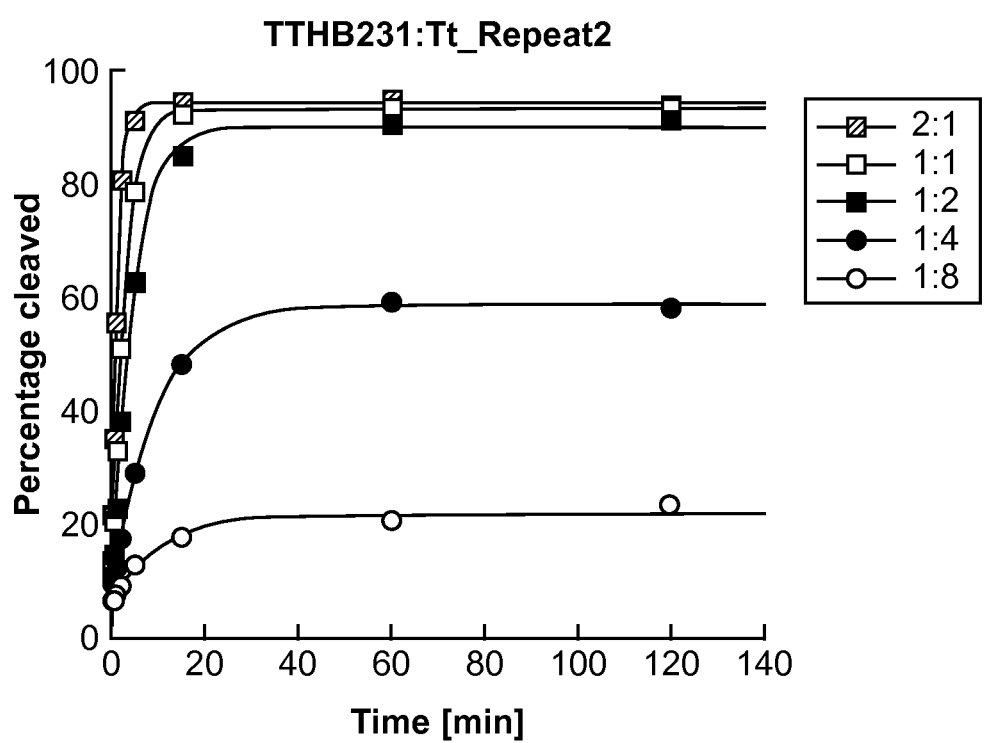
FIGS. 6A and 6B are graphs showing cleavage assay in multiple turnover conditions and gradually increased stoichiometric excess of substrate.
Figure 6B:
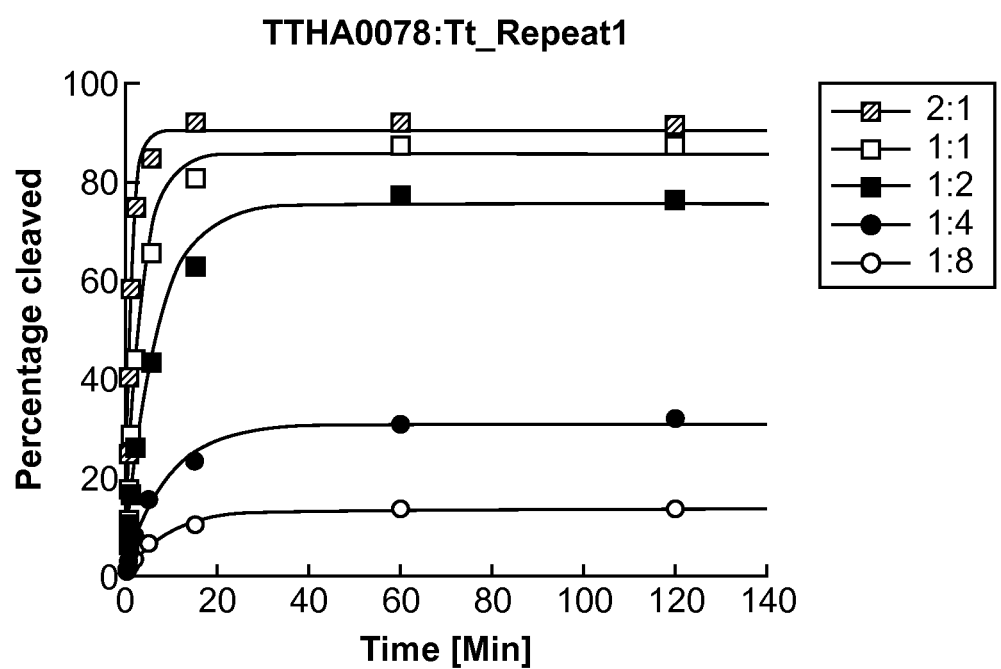
Figure 7A:
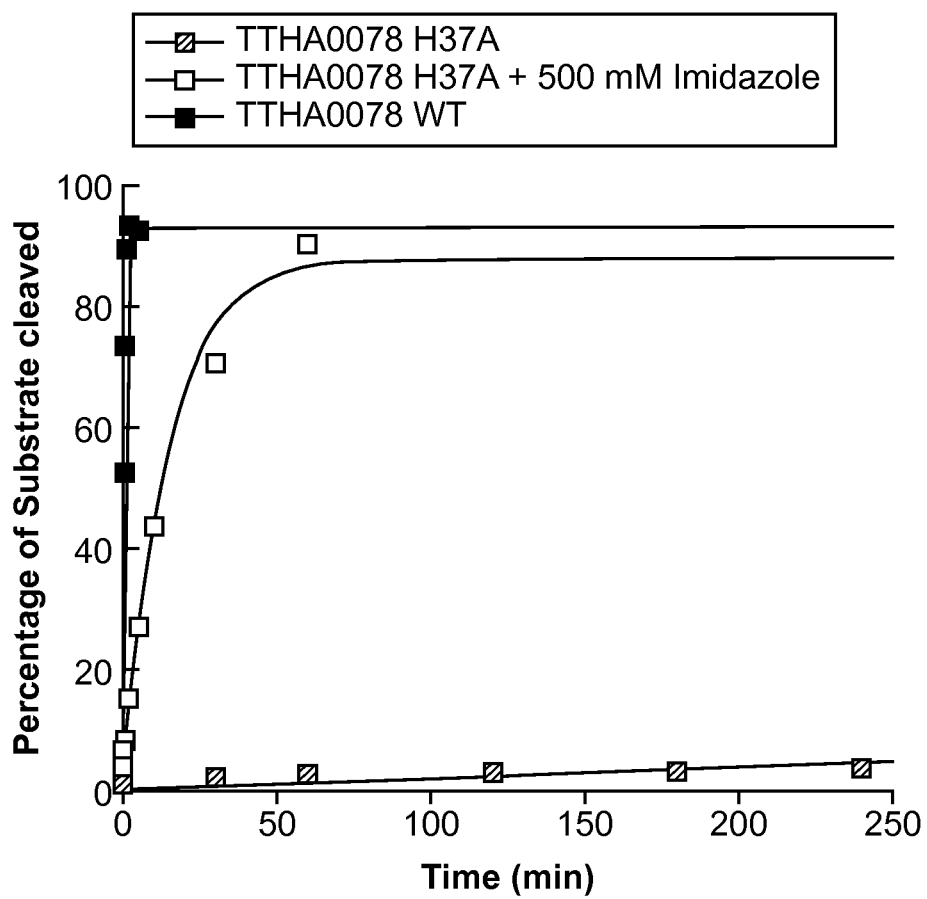
FIGS. 7A and 7B depict results of a cleavage assay of TTHA0078 (FIG. 7A) and TTHB231 (FIG. 7B) with their respective Histidine mutants and Tt_R1 as a substrate under single turnover conditions.
Figure 7B:
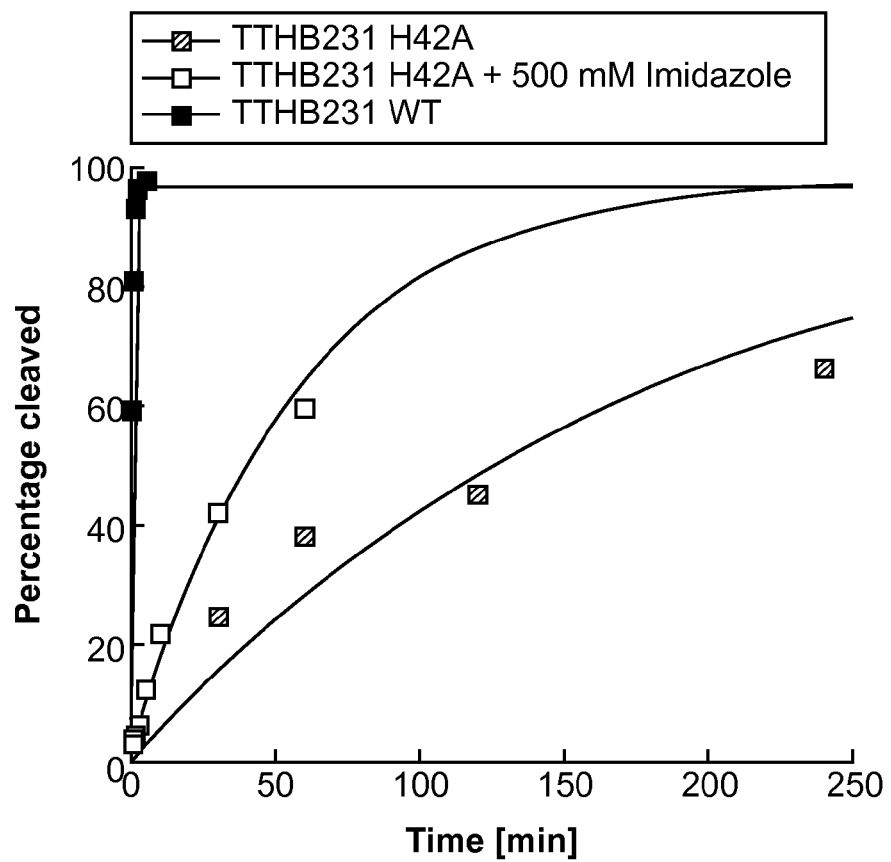
Figure 8A:
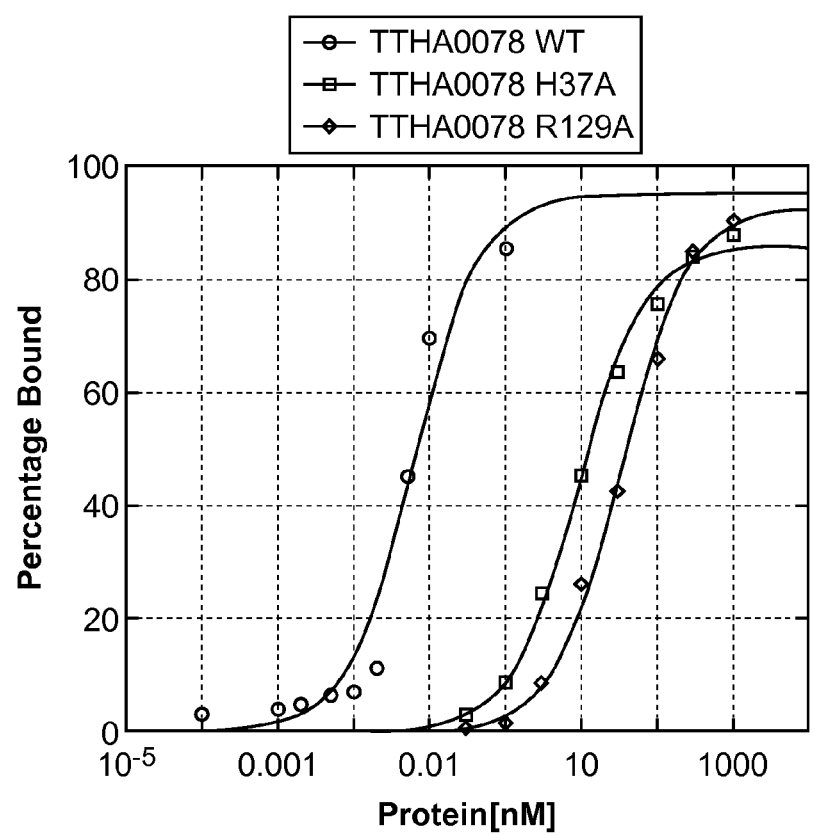
FIGS. 8A and 8B depict binding affinities of TTHA0078 wild type (WT) and TTHA0078 mutants at residues H37 and R129 for substrate binding to Tt_Repeat1 RNA (FIG. 8A) and Tt_Repeat2 RNA (FIG. 8B).
Figure 8B:
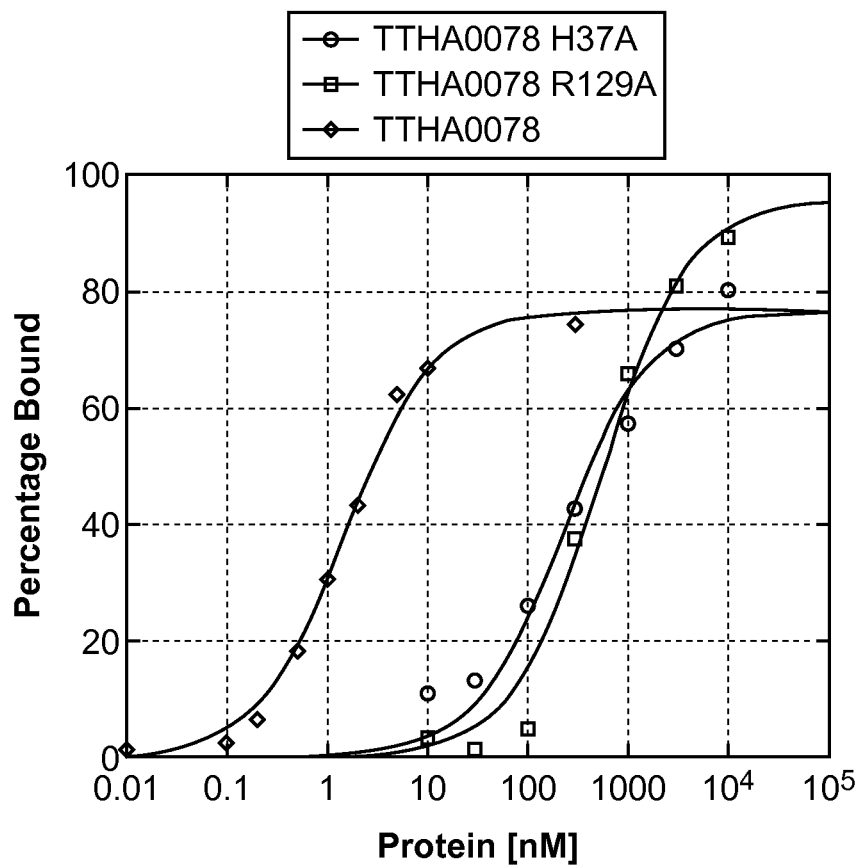

The data presented in FIG. 4 show that mutations at different parts of the stem have significant impact on binding affinity of TTHA0078 to its substrate.
In contrast to comparable previous studies, binding of TTHA0078 to the RNA in absence of its 5' handle was not observed. To determine which parts of the 5' handle have a major effect on binding affinity, a series of RNAs that are gradually truncated was created; and the binding affinities of the truncated forms was determined. In FIG. 5, the number at position n indicates that RNA of that length binds x-fold stronger than the next shorter RNA. For example, nts [7 . . . 29] bind 2.3 fold stronger to TTHA0078 than nts [8 . . . 29].
TTHA0078 and TTHB231 are Single Turnover Enzymes.
To determine if the two Cas6 proteins are capable of cleaving multiple substrates an assay was performed in which the enzyme was present in sub-stoichiometric amounts. Both enzymes seem to be single turnover enzymes, since the cleaved fractions greatly fit a single exponential decay curve that flattens out proportional to the stoichiometric excess of RNA. The data are shown in FIGS. 6A and 6B. FIGS. 6A and 6B are graphs showing the results of the cleavage assay in multiple turnover conditions and gradually increased stoichiometric excess of substrate. FIG. 6A shows the data for TTHB231 with Tt_Repeat2 substrate; FIG. 6B shows the data for TTHA0078 with Tt_Repeat 1 substrate. At higher excess of RNA the percentage of cleaved RNA flattens out significantly below 100% even after 120 minutes of incubation.

Example 2

Cas5 Mutant

The bacterium *Desulfovibrio vulgaris* (Dvu) possesses a CRISPR system of the subtype I-C. Each of its four uncharacterized Cas genes (Cas5, Cas8c, Cas7, and Cas4) was tagged with maltose-binding protein (MBP), purified, and tested for in vitro cleavage of the *D. vulgaris* CRISPR RNA hairpin. Cas5 was identified as the endoribonuclease of this subtype I-C system.
The amino acid sequence of Dvu Cas5 is as follows:

(SEQ ID NO: 13)
MTHGAVKTYGIRLRVWGDYACFTRPEMKVERVSYDVMPPSAARGILEA

IHWKPAIRWIVDRIHVLRPIVFDNVRRNEVSSKIPKPNPATAMRDRKP

LYFLVDDGSNRQQRAATLLRNVDYVIEAHFELTDKAGAEDNAGKHLDI

FRRRARAGQSFQQPCLGCREFPASFELLEGDVPLSCYAGEKRDLGYML

LDIDFERDMTPLFFKAVMEDGVITPPSRTSPEVRA, where His-141 is bolded and underlined.
As shown from the cleavage assay data provided in FIG. 11, Cas5 is an endoribonuclease that cleaves pre-crRNA.
As shown in FIG. 12, comparison between the Cas5-processed RNA product and a hydrolysis ladder and T1 digest demonstrates that Cas5 cleaves at the bottom of the pre-crRNA stem loop, after base G21.
Electrostatic mapping of a known Cas5 family protein structure (see PDB entry 3KG4) revealed a positively charged region of the protein suggestive of a nucleic acid binding pocket. Conservation mapping based on BLAST results of the *D. vulgaris* Cas5 protein sequence and displayed on the 3KG4 protein structure showed high conservation of residues in the putative substrate-binding site.

Histidine 141 was chosen as a target for site-directed mutagenesis based on its location within the putative RNA binding region.

Figure 13:
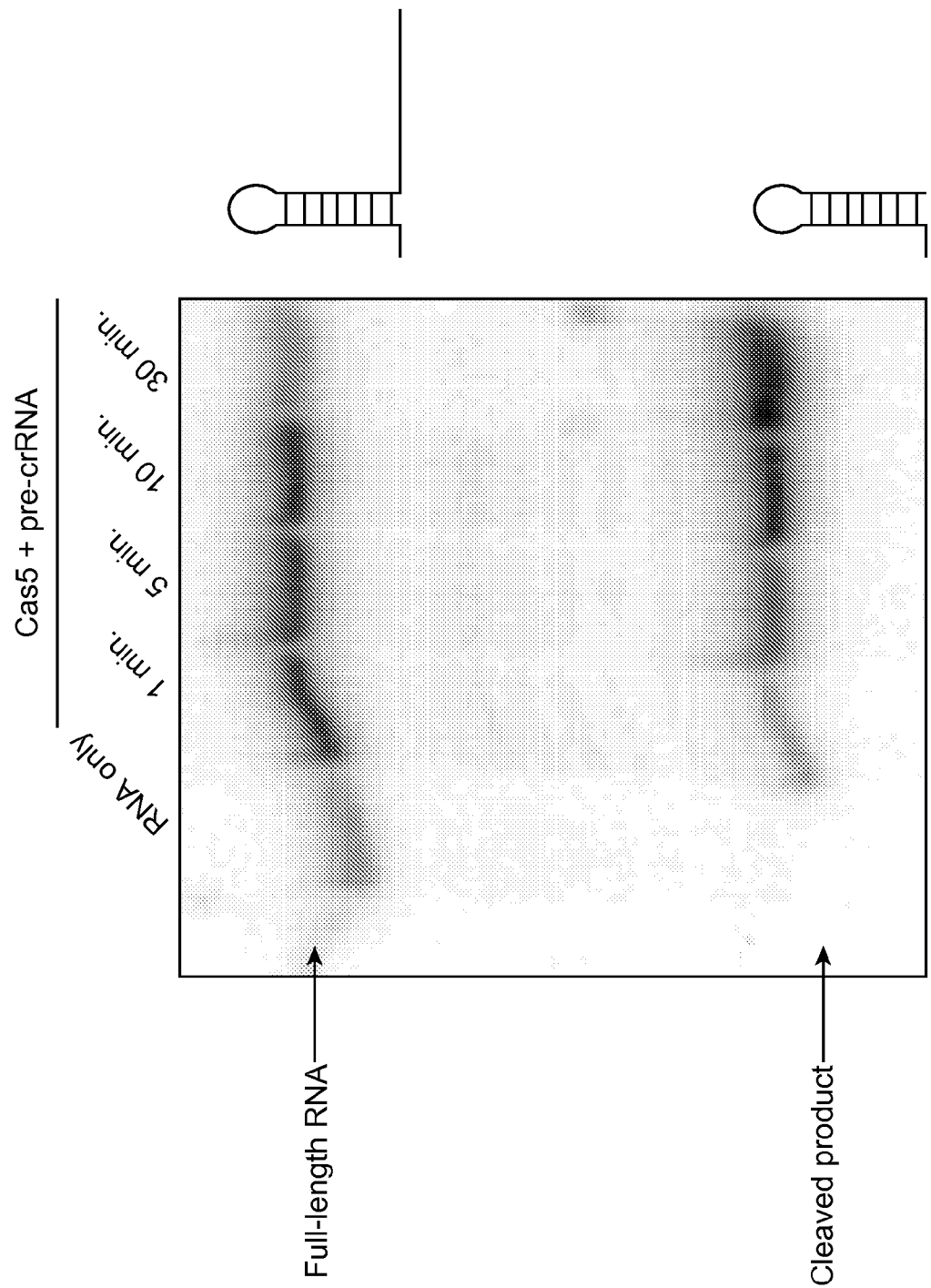
FIG. 13 depicts cleavage of pre-crRNA by Cas5.
Figure 14A:
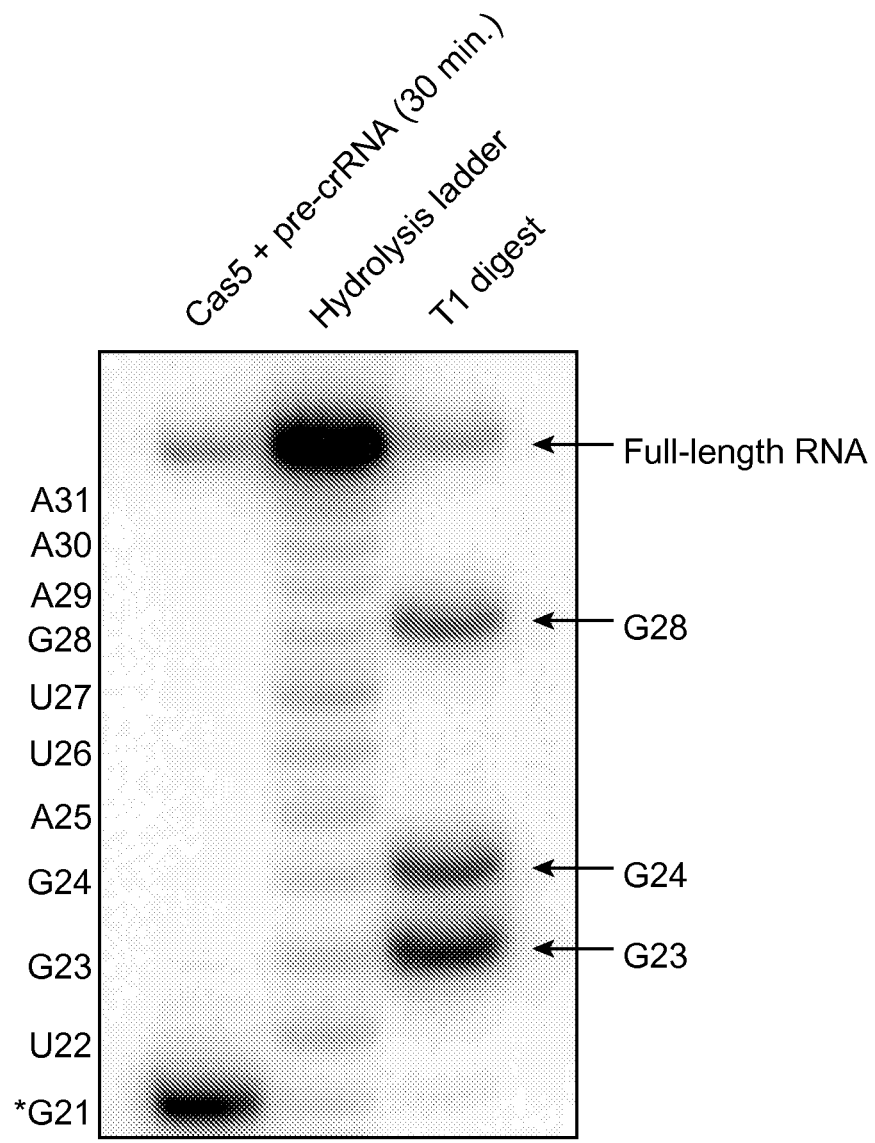
FIGS. 14A and 14B present data showing that Cas5 cleaves pre-crRNA at base G21.
Figure 14B:
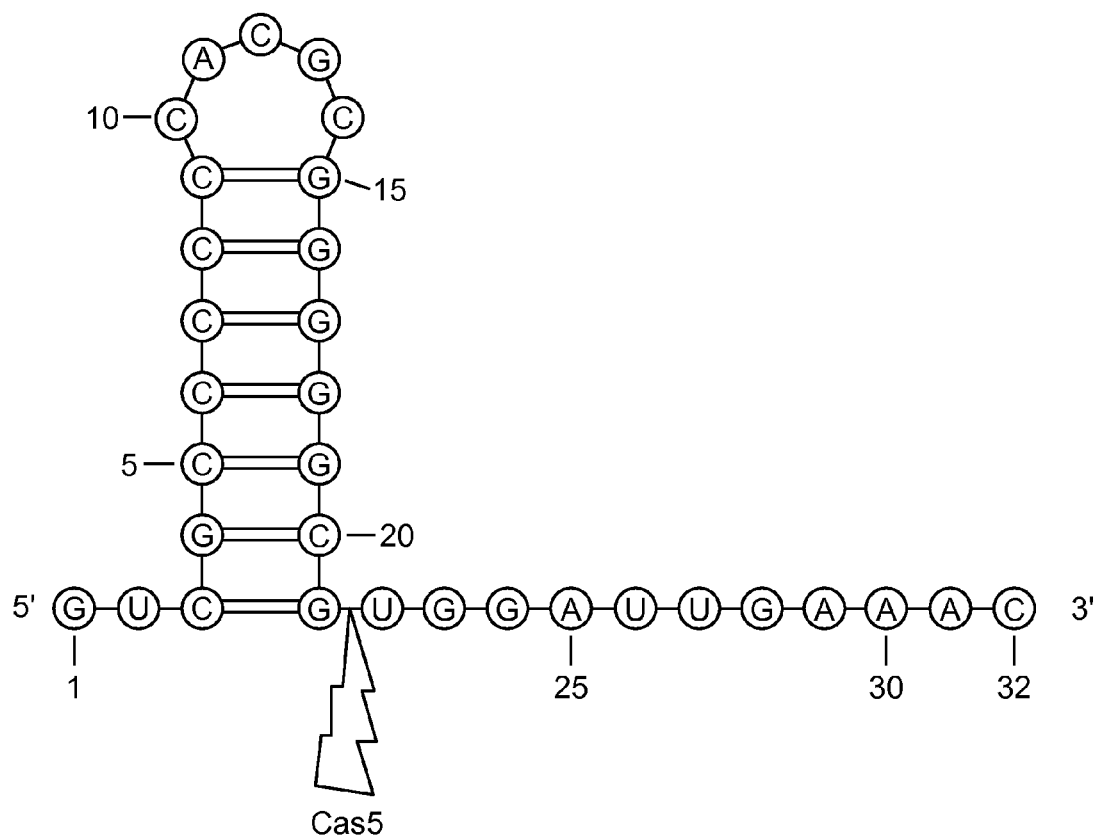

Data are shown in FIGS. 13 and 14 (FIGS. 14A and 14B). FIG. 13 depicts cleavage of pre-crRNA by Cas5. FIGS. 14A and 14B present data showing that Cas5 cleaves pre-crRNA at base G21.

Example 3

Evolution of CRISPR RNA Recognition and Processing by Cas6 Endonucleases

Results

Figure 26:
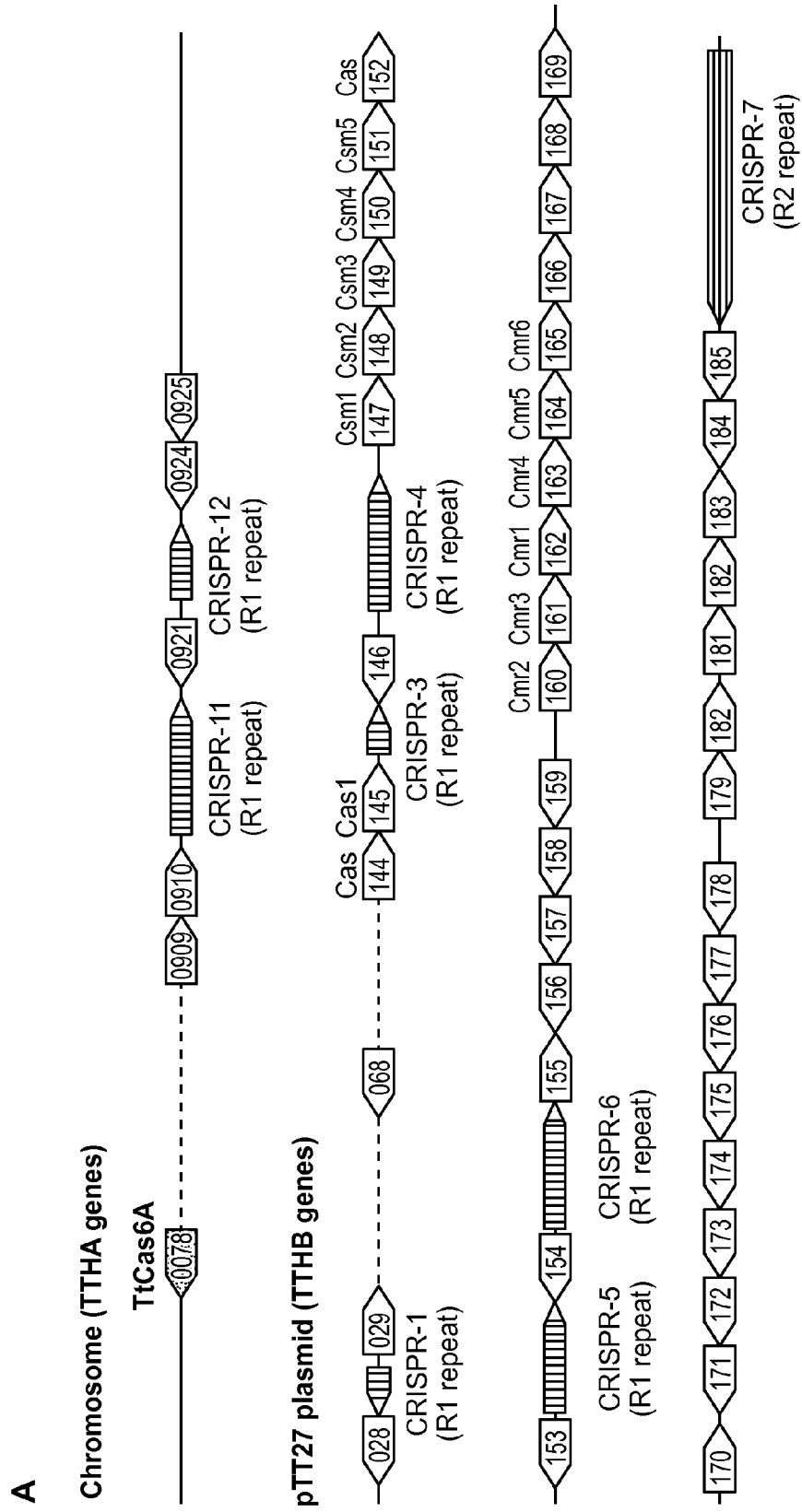
FIGS. 26A-B depict cleavage of repeats R1 and R3, but not R2, by TtCas6A and TtCas6B.

TtCas6A and TtCas6B Bind and Cleave CRISPR Repeats R1 and R3 and Retain their Product RNAs after Cleavage The genome of *Thermus thermophilus* HB8 harbors eleven CRISPR loci containing three distinct types of repeats, termed R1-3 herein (FIG. 22A; FIG. 26). All CRISPR loci are constitutively transcribed (Agari et al, 2010; Juranek et al, 2012). Irrespective of the CRISPR locus of origin, all crRNAs in *T. thermophilus* contain a 5'-terminal 8-nucleotide handle derived from the repeat sequence that results from sequence-specific cleavage at the 3' end of the hairpin structure predicted in each crRNA repeat (Juranek et al, 2012). Three Cas6-superfamily genes have been identified in the *T. thermophilus* genome: TTHB231, TTHB192 and TTHA0078 (FIG. 26A). Previous structural and biochemical studies showed that the TTHB192 gene product, a member of the Cas6e family, cleaves the R2 repeat found in the two spacer/repeat arrays flanking the type I-E (*E. coli* subtype) Cas operon in the *T. thermophilus* genome. While TTHB231 is embedded in a hybrid type I operon flanked by R3 repeat loci, TTHA0078 is not part of any CRISPR locus.

To determine whether TTHA0078 and TTHB231 (hereafter referred to as TtCas6A and TtCas6B, respectively) are responsible for processing pre-crRNAs originating from R1 and/or R3 repeat loci, recombinant TtCas6A and TtCas6B proteins were expressed and purified from *Escherichia coli* and tested for endonucleolytic activity using in vitro transcribed RNAs. Both proteins cleaved R1 and R3 repeat RNAs efficiently, while neither was able to cleave R2 repeat RNA (FIG. 26B). To characterize the binding affinities of TtCas6A and TtCas6B to their cognate crRNA repeats, we performed electrophoretic mobility shift assays (EMSAs) using 5'-[$^{32}$P]-radiolabeled R1 and R3 repeat RNAs. As endonucleolytic cleavage occurred to completion during the course of the binding reactions, the calculated equilibrium dissociation constants reflect product, rather than substrate, binding. TtCas6A bound to the R1 repeat cleavage product with an apparent $K_d$ of 90±21 pM, while binding to the R3 repeat cleavage product was approximately nine-fold weaker (808±154 pM). TtCas6B bound to R1 and R3 repeats with comparable dissociation constants of 1.96±0.28 nM and 3.90±0.78 nM, respectively (FIG. 1B). The observed high-affinity product binding is consistent with the conclusion that, like many other Cas6-superfamily endonucleases, both TtCas6A and TtCas6B function as single-turnover enzymes. To test this hypothesis, we performed cleavage assays at a range of substrate:enzyme molar ratios, measured the rate of cleavage, and quantified the product yield (FIG. 22C). The cleavage reaction yields scaled proportionally to enzyme concentration at sub-stoichiometric enzyme concentrations, while the apparent first order rate constants remained essentially unchanged, indicating single-turnover catalysis. Collectively, these findings suggest that TtCas6A and TtCas6B are involved in processing precursor transcripts of repeat R1 and R3-containing CRISPR loci in *T. thermophilus* and that both enzymes likely remain bound to their products following cleavage.

FIG. 22 illustrates that TtCas6A and TtCas6B both cleave repeats R1 and R3 and retain their cleaved products. (A) Sequences and predicted secondary structures of *T. thermophilus* CRISPR repeats. Sites of cleavage are indicated with blue arrows. TtCas6e (TTHB192) cleaves repeat R2, while TtCas6A (TTHA0078) and TtCas6B (TTHB231) both cleave repeats R1 and R3. (B) Cleavage product binding affinities of TtCas6A and TtCas6B enzymes. Maltose binding protein (MBP)-fused TtCas6A or TtCas6B were bound to in 5'-radiolabelled, vitro transcribed R1 and R3 RNAs. Bound and unbound fractions were resolved by electrophoresis on a native polyacrylamide gel and visualized by phosphorimaging. The data for these and all subsequent binding assays were fit with standard binding isotherms (solid line). Error bars on each data point denote standard error of the mean (SEM) from three independent experiments. (C) Experiments to confirm single turnover. RNA cleavage assays were carried out at indicated protein:RNA ratios. RNA cleavage was monitored using denaturing polyacrylamide gel electrophoresis. The data from these and all subsequent endoribonuclease activity assays were fit with single exponential curves to yield first-order rate constants. (Top to bottom: FIG. 22A, SEQ ID NOs: 1, 2, 55).

FIG. 26 demonstrates that TtCas6A and TtCas6B cleave repeats R1 and R3, but not R2. (A) Diagram of CRISPR loci and cas genes in the genome of *Thermus thermophilus* HB8 based on the CRISPRdb database (Grissa et al, 2007). The diagram was modified after Agari et al, 2010 (Agari et al, 2010) and includes the present annotation of the *T. thermophilus* CRISPR loci. cas genes are depicted as white arrowheads and numerals in the arrowheads indicate gene numbers for TTHA (chromosomal) and TTHB (plasmid pTT27) genes, respectively. Gene names are shown above the arrowheads, and the three Cash-encoding genes are colored in teal (TTHA0078), blue (TTHB231) and light green (TTHB192), respectively. CRISPR arrays are depicted as patterned arrowheads and those that share a pattern have the same or similar repeat sequences (R1 to R3). (B) RNA cleavage by TtCas6A and TTCas6B enzymes. In vitro transcribed repeat R1-3 RNAs were incubated with purified recombinant TtCas6A or TtCas6B. Cleavage products were resolved by denaturing polyacrylamide gel electrophoresis and visualized by staining with SYBR Gold.

Crystal Structures of RNA-Bound TtCas6A and TtCas6B Reveal the Mechanism of Substrate Recognition and Cleavage.

To determine how TtCas6A and TtCas6B bind and cleave their RNA substrates, we solved crystal structures of these proteins both alone and in complexes with their cognate RNAs (FIG. 23A, FIG. 30). For TtCas6A, we obtained a structure of the enzyme bound to a substrate mimic based on the R1 repeat sequence, consisting of the R1 stem-loop flanked by two additional nucleotides on either end of the stem. Cleavage of the substrate mimic RNA was prevented by introducing a 2'-deoxyribonucleotide at the G28 position, thereby removing the 2'-hydroxyl nucleophile required for the cleavage reaction. In addition to the substrate mimic complex, a crystal structure of a complex of TtCas6A and a cleaved RNA product was obtained when full-length R1 repeat was bound to wild-type TtCas6A and allowed to undergo cleavage during subsequent complex purification and crystallization. Finally, we determined the crystal structure of the TtCas6A H37A mutant, lacking a critical active site residue, in the absence of bound RNA. For TtCas6B, we determined crystal structures of the wild-type enzyme alone and in complex with a product of the R3 repeat cleavage reaction.

In all crystal structures, both TtCas6A and TtCas6B form crystallographic (RNA-free TtCas6B) or non-crystallographic (all TtCas6A structures and the TtCas6B-product complex) dimers (FIG. 27), consistent with size exclusion chromatography results indicating that both enzymes are dimers in solution. The buried surface area of the TtCas6A dimer is 924 Å$^2$, while the TtCas6B dimer buries 1008 Å$^2$. Strikingly, while the TtCas6B-R3 product crystal structure reveals a 2:2 stoichiometry, both substrate and product TtCas6A-R1 RNA complexes crystallized with an apparent 2:1 stoichiometry, with only one RNA molecule bound to the non-crystallographic TtCas6A dimer. Size exclusion chromatography of TtCas6A and TtCas6B-RNA complexes used for crystallization as well as their absorbance ratios at 280 and 260 nm were indicative of 2:2 stoichiometry. Additionally, both proteins behaved similarly in cleavage assays (FIG. 22C) and no negative cooperativity was observed for TtCas6A in binding assays. The apparent 2:1 stoichiometry of the TtCas6A-RNA complexes is therefore likely a crystallization-induced artifact.

FIG. 27 depicts dimeric structures of TtCas6A and TtCas6B enzymes bound to substrate mimic and product RNAs. Proteins are depicted in ribbon format and colored in teal (TtCas6A) or blue (TTCas6B). Bound RNAs are depicted in cartoon format and colored in yellow. In all cases, the two protein molecules form a non-crystallographic dimer in the asymmetric unit of the crystal. (A) Ribbon diagram showing the 2:1 TtCas6A-R1 substrate mimic complex. (B) Ribbon diagram showing the 2:1 TtCas6A-R1 product complex (C) Ribbon diagram showing the 2:2 TtCas6B-R3 product complex.

Overall, both TtCas6A and TtCas6B adopt double-ferredoxin folds similar to those observed for TtCas6e, PfCas6 and a non-catalytic Cas6 homolog from *Pyrococcus horikoshii* (FIG. 28A,B). The N-terminal ferredoxin domains of the two TtCas6 proteins also superimpose well with the single ferredoxin fold found in the structure of PaCas6f. The two TtCas6 enzymes are highly similar to each other and superimpose with a root-mean-square deviation (rmsd) of 2.1 Å over 227 Cα atoms, reflecting the high degree of sequence identity (32%) between the two proteins (FIG. 28A,B).

As anticipated, the R1 and R3 repeat RNAs form stem-loop structures. In both proteins, the RNAs bind in a positively charged cleft located between the two ferredoxin folds, as observed in the structures of TtCas6e-R2 repeat complexes. In further analogy with TtCas6e, TtCas6A and TtCas6B complexes also insert a beta-hairpin from their C-terminal ferredoxin domains into the major groove of the dsRNA stems (FIG. 23A). In the TtCas6A-substrate mimic complex, the two nucleotides downstream of the scissile phosphate are recognized in a sequence-specific manner through base-specific interactions (described in detail below). The structures of the RNA product complexes of both TtCas6A and TtCas6B reveal 2'-3' cyclic phosphate groups in the respective active sites, consistent with a catalytic mechanism involving nucleophilic attack by the 2'-hydroxyl of the upstream nucleotide (G28) (FIG. 23A, B).

The active site of TtCas6A is located in a pocket surrounded by helix α1 and the α1-β2 and β10-β11 loops (FIG. 23B). The scissile phosphate group is contacted by Arg22 and His37, and positioned in an extended conformation that would permit an in-line attack by the 2'-hydroxyl of G28 (FIG. 23B). His37 is positioned to hydrogen bond with the 5' or 3' bridging oxygen atoms, and might therefore act as the general acid that protonates the leaving group during catalysis, in addition to charge-stabilizing the scissile phosphate. The active site of TtCas6B is composed of His23, His42 and Tyr256, whereby Tyr256 and His42 hydrogen bond to the 2' and 3' oxygens of the cyclic phosphate product. In a substrate complex, Tyr256 would likely be positioned to deprotonate the 2'-hydroxyl of G28 during nucleophilic attack, while His42, in analogy with His37 in TtCas6A, would stabilize the scissile phosphate and protonate the leaving group.

To shed light on the catalytic mechanism of TtCas6A and TtCas6B, we performed cleavage assays using wild type proteins as well as active site mutants TtCas6A H37A and TtCas6B H42A using repeat R1 as a substrate (FIG. 2C). The first order rate constant determined under single-turnover conditions for wild type TtCas6A (3.2 min$^{-1}$) and TtCas6B (3.7 min$^{-1}$) are in good agreement with first order rate constants previously determined for PaCas6f and TtCas6e. Strikingly, we found TtCas6A H37A to be almost inactive (17,000-fold cleavage defect), while TtCas6B H42A showed only a ~300-fold cleavage defect, indicating that despite considerable structural homology, the catalytic mechanisms of TtCas6A and TtCas6B might be substantially different. To confirm the role of the active site histidine His37 in TtCas6A, we sought to replace the histidine side chain by adding imidazole (a histidine mimic) to the cleavage reaction. This imidazole complementation strategy has been used recently to convert PaCsy4 into an inducible endoribonuclease. In the presence of 500 mM imidazole, the cleavage rate of TtCas6A H37A was enhanced ~360-fold, underscoring the importance of the active site histidine in the catalytic mechanism of TtCas6A.

The Active Site of TtCas6A Undergoes a Conformational Ordering Upon RNA Binding

The crystal structures of TtCas6A-RNA complexes allow comparisons of the RNA-free and RNA-bound states of the enzyme due to the presence of an RNA-free TtCas6 molecule in the crystallographic asymmetric unit. In the RNA-free TtCas6A, the loop connecting helix α1 and strand β2 (residues 33-40), which contains the active site histidine His37, is disordered (FIG. 23D). Upon substrate RNA binding, the loop becomes ordered and forms a short helical segment, as the backbone carbonyls of Pro40 and His37 form hydrogen bonds with the 2' hydroxyl groups of G26 and G27, respectively, and the His37 side chain forms a hydrogen bond with the 3'-hydroxyl oxygen of G28. Additional interactions mediate substrate recognition downstream of the scissile phosphate; the 6-amino group of A29 forms a hydrogen bond with the amide carbonyl of Pro34, while the U30 is specifically recognized through hydrogen bonding interactions with the backbone amide of Gly85 and carbonyl of Arg83. The ordering of the His37-containing active site loop persists in the product complex, suggesting that scissile phosphate recognition by His37 and additional interactions with the ribose-phosphate backbone upstream of the cleavage site drive the conformational change upon substrate recognition.

FIG. 23 depicts various structures of TtCas6A and TtCas6B enzymes bound to substrate mimic and product RNAs. (A) Ribbon diagrams showing the overall views of Cash-RNA complexes: TtCas6A-R1 substrate mimic (left), TtCas6A-R1 product (middle) and TtCas6B-R3 product (right). Bound RNAs are depicted in cartoon format. The scissile phosphate groups are depicted as spheres. All cartoon molecular diagrams were generated using Pymol. ("www" followed by ".pymol.org"). (B) Zoomed-in views of the TtCas6 active sites, shown in the same orientation as in A. Hydrogen bonding interactions are denoted with dashed lines; numbers indicate interatomic distances in A. (C) Endonuclease activity assays of wild-type (WT) and active site mutant proteins. For the TtCas6A H37A mutant, the cleavage assay was also carried out in the presence of 500 mM imidazole. (D) Active site of TtCas6A undergoes conformational ordering upon substrate recognition. Left: zoomed-in view of the active site in the RNA-free TtCas6A molecule in the 2:1 protein-R1 substrate mimic complex. Right: zoomed-in view of the active site in the RNA-bound TtCas6A molecule. Hydrogen-bonding interactions are denoted with dashed lines. (SEQ ID NO: 53).

FIG. 28 depicts sequence and structural alignments of TtCas6A and TtCas6B enzymes. (A) Structure-based sequence alignment of TtCas6A and TtCas6B with *Pyrococcus furiosus* Cas6 (PfCas6, PDB code 3PKM), *T. thermophilus* Cas6e (TtCas6e, also known as Cse3 or CasE, PDB code 2Y8W) and *Pseudomonas aeruginosa* Cas6f (PaCas6f, also known as Csy4, PDB code 2XLK). The structures were aligned using the PDBeFold server (Velankar et al, 2011). The sequence alignment was generated using ESPript 2.2 (Gouet et al, 1999). Active site residues are highlighted in green. Secondary structure elements present in the TtCas6A protein are shown above the sequence. (B) Structural superpositions of Cas6-RNA complexes. Top; from left to right: Ribbon diagrams of TtCas6B-R3 product RNA complex (blue, this study), PfCas6-RNA complex (pink, PDB code 3PKM), TtCas6e-20 nt substrate mimic RNA complex (light green, PDB code 2Y8W) and PaCas6f-substrate mimic complex (light blue, PDB code 2XLK). The structures were superimposed using DALI (Holm & Sander, 1995) and are shown in identical orientations. Bottom: Structural superpositions of Cas6 enzymes with TtCas6A. Pairwise root mean square deviations (rmsds) and the number of Cα atoms in each superposition are indicated.

FIG. 30 depicts a table of X-ray data collection and refinement statistics.

Recognition of RNA Sequence and Geometry by TtCas6A and TtCas6B

In both TtCas6A and TtCas6B, extensive networks of ionic and hydrogen bonding interactions are involved in RNA recognition (FIG. 24A,B). In both proteins, the RNA-stem loop straddles the β10-β11 loop, and is positioned in a cleft between the active site loop and the beta-hairpin (β7-β8) that inserts into the major groove. In TtCas6A, the hairpin presents Arg129 for sequence-specific hydrogen bonding contacts with the lower three C-G base pairs in the stem (FIG. 24A). TtCas6B lacks an equivalent residue in the major groove-binding hairpin. Instead, the side chain of Ser147 hydrogen bonds to the base of G25 as the only sequence-specific contact with the RNA (FIG. 24A). In both Cas6-RNA complexes, the ribose-phosphate backbone in the 3' half of the stem-loop is anchored through a series of hydrogen bonding contacts involving the phosphate groups of nucleotides 25-28 and the 2'-hydroxyl groups of nucleotide G26 in the TtCas6A-RNA complexes and nucleotide G27 in the TTCas6B-product complex, respectively (FIG. 24A,B). Thus, as in the structures of PaCas6f (PaCsy4) and TtCas63 (TtCse3), the RNAs are recognized both via their sequence and their shape.

To test the importance of the stem sequence for substrate RNA recognition by TtCas6A, a series of EMSAs was performed using R1 repeat-derived RNAs that carried single base pair substitutions (C-G→A-U). All mutant RNAs contained the complete 5' segment and additional two nucleotides downstream of the cleavage site. Compared to the wild-type RNA, substitution of any of the four C-G base pairs in the stem led to about five-fold decrease in affinity (FIG. 24C). This is consistent with the observation that the lower three C-G base pairs are specifically read out by Arg129. The binding defect observed upon mutation of the closing (uppermost) base pair could be due to loss of stability of the stem-loop structure, which is determined by the closing base-pair (Serra et al, 1993). To further investigate the protein determinants of RNA binding, we tested the TtCas6A mutants H37A and R129A and performed binding assays using substrates R1 and R3 (FIG. 24D). Mutation of Arg129 resulted in a strong binding defect with ~260- and ~290-fold decrease in affinity for R1 and R3, respectively, when compared to wild-type TtCas6A, in agreement with the observed function of this residue in simultaneous recognition of the lower three C-G base pairs in the RNA stem-loop. A similar, but somewhat weaker effect was observed for TtCas6A H37A, which yielded ~70- and ~90-fold reduction in affinities for R1 and R3 repeat RNAs, respectively. The binding defects indicate that besides playing a key role in the catalysis of RNA cleavage, the His37 side-chain also contributes to substrate binding. This is consistent with the ordering of the active site loop observed upon substrate recognition, which appears to be driven in part by the interaction between the His37 side chain and the scissile phosphate group.

Figure 24:
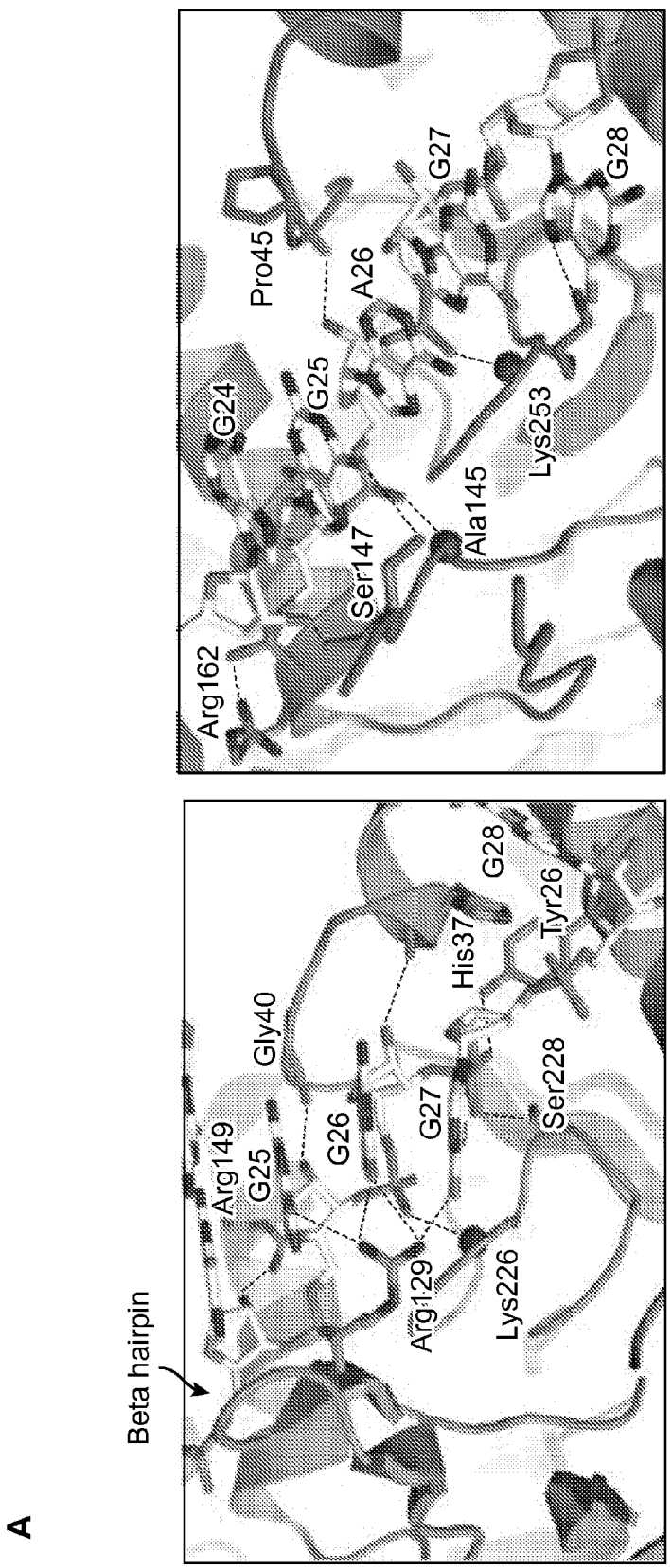
FIGS. 24A-D depict features of RNA recognition by TtCas6A and TtCas6B.

FIG. 24 depicts RNA recognition by TtCas6A and TtCas6B. (A) Detailed views of RNA binding by TtCas6A (left) and TtCas6B (right). Hydrogen bonding interactions are indicated with dashed lines. Spheres denote backbone amide nitrogen atoms of Lys226 in TtCas6A (left) and Ala145 and Lys253 in TtCas6B (right). (B) Schematic diagrams of protein-RNA contacts in the TtCas6A-R1 substrate mimic (left) and TtCas6B-R3 product complexes. Amino acid residues contacting the bound RNA via ionic or hydrogen-bonding interactions are highlighted. Arrows mark the scissile phosphates. Circles denote phosphodiester groups in the RNA backbone. Lines indicate base-pairing interactions. (C) Base-pair contributions to R1 repeat recognition by TtCas6A. A series of RNAs in which individual C-G base pairs were substituted with A-U were prepared and assayed for binding to TtCas6A using EMSAs. The data for each base pair substitution is expressed as Kd and as fold reduction in affinity relative to wild-type R1 RNA. (D) R1 (left) or R3 (right) product RNA binding by WT TtCas6A or R129A and H37A mutants was quantified using EMSAs. The data are plotted as in FIG. 22B.

Recognition of the 5'-Segment of the Repeat Suggests a Two-Site Model for RNA Binding The structures of TtCas6A- and TtCas6B-product RNA complexes reveal that besides recognizing the stem-loop, the enzymes also make specific interactions with the upstream RNA sequence. In the TtCas6A-R1 product complex, two nucleotides upstream of the stem-loop are observed in $2F_o$-$F_c$ electron density maps. The remainder of the 5' segment of the R1 repeat RNA is not ordered, although the RNA is intact in the crystal. The purine bases of the two ordered nucleotides in the 5' segment are inserted into a crevice at the interface of the two TtCas6A molecules in the non-crystallographic dimer (FIG. 25A). G16 engages in hydrogen bonding with the side chain of His134 and the backbone carbonyl of Asp188. The base of A15 is hydrogen bonded to the backbone amide and carbonyl groups of His134. In the TtCas6B-R3 product complex, the two RNA molecules in the asymmetric unit adopt slightly different conformations at their 5' ends. In one molecule, only one nucleotide (G17) upstream of the repeat stem-loop is ordered, forming hydrogen bonds with the side chains of Arg208 and Glu197, each contributed by one TtCas6B molecule in the non-crystallographic dimer (FIG. 25A). In the other RNA molecule, both G17 and A16 are ordered, and the base of A16 is tucked in and stacks below the terminal base pair of the R3 repeat stem-loop (FIG. 29A).

Inspection of the molecular surface of TtCas6A reveals a deep groove tracing the interface of the two ferredoxin folds. This groove extends from the A15-binding site towards a highly positively charged patch located on the reverse side of the protein from the active site (FIG. 25B). A similar groove is observed in TtCas6B (FIG. 29B). A sulfate ion is bound to the basic patch in the structures of both TtCas6A-R1 substrate and TtCas6A-R1 product complexes, and is contacted by the side chains of Arg121 and Arg223 (FIG. 29C). In the structure of PfCas6 bound to a fragment of its cognate repeat RNA, nucleotides 2-10 of the repeat bind to a positively charged groove located on the face of the protein opposite from the active site. Superposition of the PfCas6 and TtCas6A RNA complex structures reveals that the basic groove in TtCas6A overlaps with the PfCas6A RNA binding site such that the 3' end of the bound PfCas6 RNA fragment (nucleotide A10) aligns with the 5' end (nucleotide A15) of the R1 repeat RNA (FIG. 25C). This suggests that the basic groove in TtCas6A might constitute an additional RNA binding site that interacts with the unstructured 5' segment of the R1 repeat RNA upstream of A15. Neither nucleotides G1-G14 of the R1 product RNA, nor nucleotides G1-U15 of the R3 RNA are ordered in the crystal structures of the TtCas6A and TtCas6B complex complexes. However, it is possible that in both cases, this is a consequence of the high ionic strength of the crystallization condition and the presence of sulfate in the TtCas6A crystals. We therefore hypothesized that the unstructured 5' segment contributes to R1 RNA binding by TtCas6A. To test this, we measured the affinity of TtCas6A for a series of RNAs based on the R1 repeat in which nucleotides were progressively removed from the 5' end (FIG. 25D). Deletion of nucleotides 1-8 had little effect on binding affinity. Truncation of the R1 repeat RNA beyond nucleotide G9 led to a gradual loss of binding affinity, with an approximately 900-fold increase in $K_d$ upon deletion of residues 1-13 of the R1 repeat RNA. These results indicate that nucleotides 9-13 in the unstructured 5' segment of the repeat RNA make a considerable contribution to binding, which would be consistent with the existence of a second RNA binding site in TtCas6A.

Figure 25:
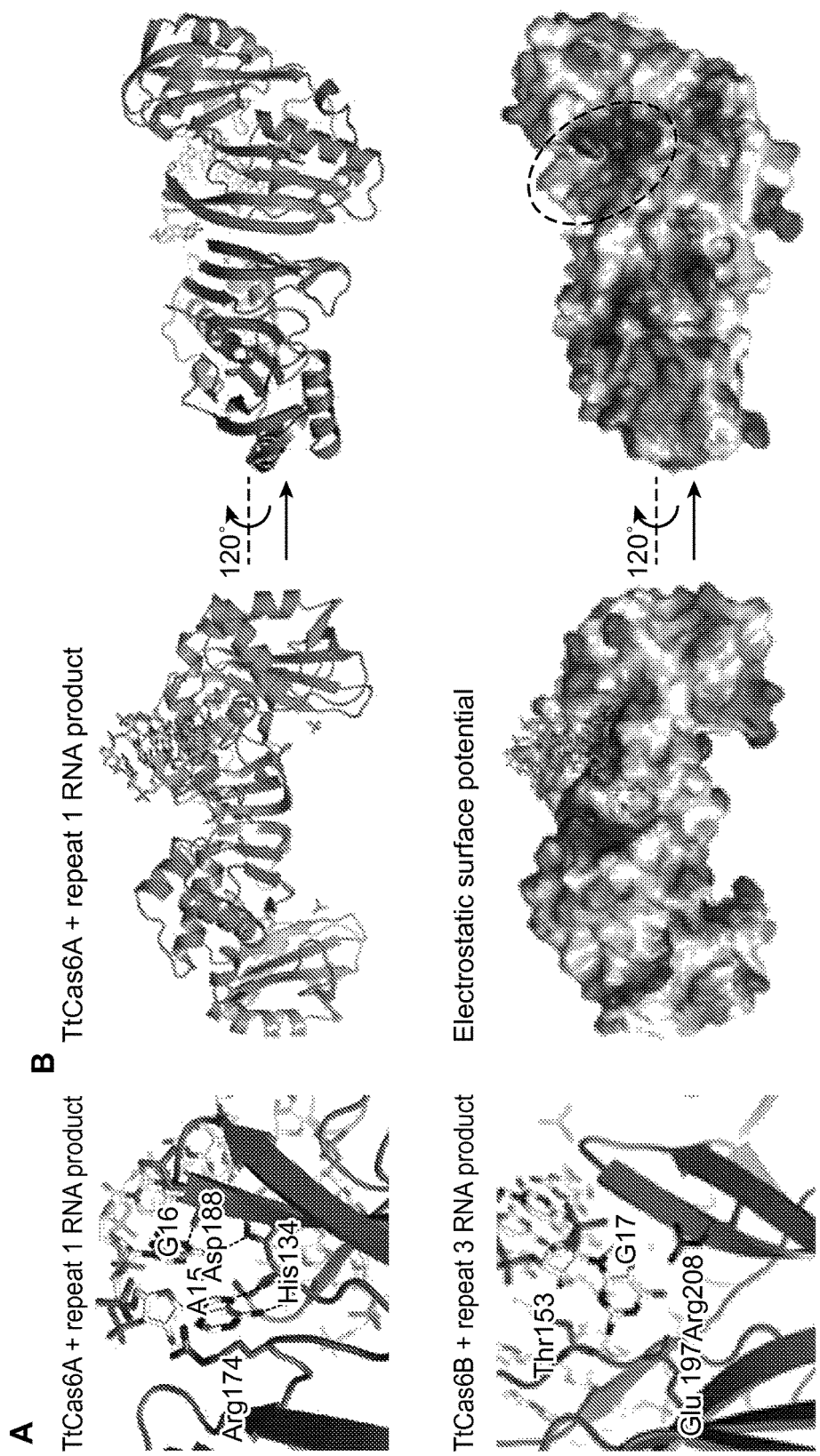
FIGS. 25A-F depict recognition of the 5' segment of the repeat RNA.

FIG. 25 demonstrates recognition of the 5' segment of the repeat RNA. (A) Details of sequence-specific recognition of nucleotides upstream of the stem-loop in RNA repeats. Top: TtCas6A-R1 product complex. Nucleotides 1-14 of the R1 product RNA are disordered. Bottom: TtCas6B-R3 product complex. Nucleotides 1-15 of the R3 product RNA are disordered. (B) Surface electrostatic potential map of TtCas6A identifies a second RNA binding site. Top: Cartoon diagram of the 2:1 TtCas6A-R1 product RNA complex. RNA is shown. Bound sulfate ions are depicted in stick format. Bottom: Electrostatic surface potential map of TtCas6A, shown in the same orientations as above. Positively charged region and negatively charged regions are shown. The positively charged patch located on the surface opposite from the active site is highlighted with a black ellipse. (C) Structural superposition of the TtCas6A-R1 product RNA (TtR1) and PfCas6-repeat RNA (PfRNA) (PDB code: 3PKM) complexes. TtCas6A; PfCas6. *T. thermophilus* R1 repeat RNA. PfRNA is colored black. Nucleotide A15 of TtR1 aligns with G10 of PfRNA. (D) Nucleotides in the single-stranded 5' segment of R1 repeat RNA contribute to binding. TtCas6A binding to a series of truncated RNAs based on the R1 repeat was quantified by EMSAs as in FIG. 22B. The data are expressed as Kd and as a fold binding defect relative to wild type R1 repeat. 5'-terminal G nucleotides resulting from in vitro transcription are shown in G. (E) Structural superposition of TtCas6A dimer with *P. furiosus* repeat RNA, based on the superposition shown in D. TtCas6A is colored according to surface electrostatic potential and shown in the same orientations as in B. TtR1 is colored orange; PfRNA is colored black. (F) Cartoon model of RNA recognition by TtCas6 enzymes. TtCas6A binds the stem-loop RNA (solid line) at the interface of the two ferrdoxin-like domains. Additionally, the 5' segment of the repeat RNA (dashed line) is bound by a distal positively charged cleft on the opposite surface from the active site. (FIG. 25D: left, SEQ ID NO: 56)(FIG. 25D: right bottom, SEQ ID NO: 57).

Figure 29:
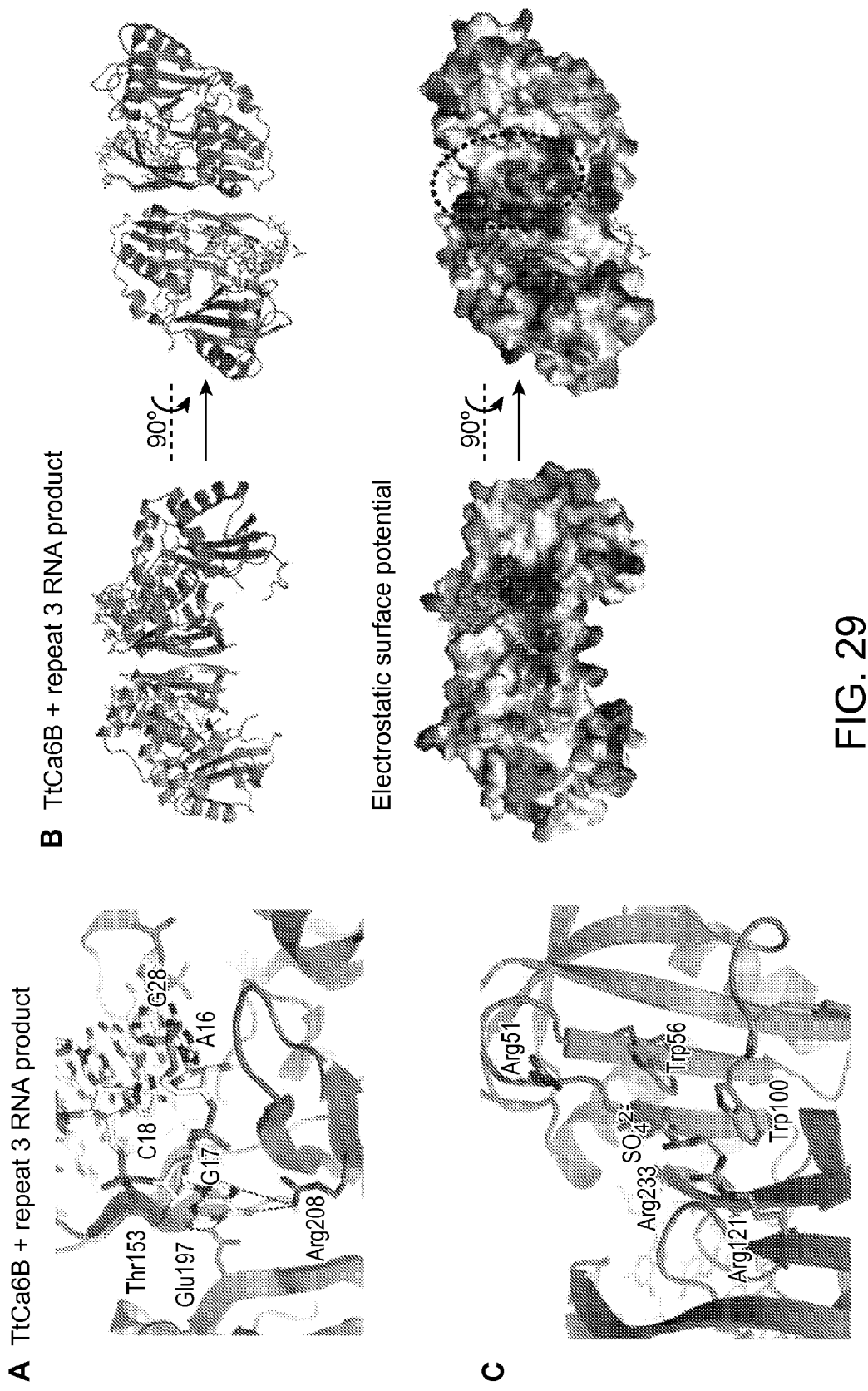
FIGS. 29A-C depict various structural views of TtCas6A and TtCas6B complexed with substrate and/or product.

FIG. 29 depicts various structural views of TtCas6A and TtCas6B complexed with substrate and/or product. (A) Details of sequence-specific recognition of nucleotides upstream of the stem-loop in TtCas6B-R3 product RNA complex. Nucleotides 1-14 of the R3 product RNA are disordered. (B). Top: Cartoon diagram of the 2:2 TtCas6B-R3 product RNA complex. RNA is shown in orange. Bottom: Electrostatic surface potential map of TtCas6A, shown in the same orientations as above. Blue, positively charged region; red, negatively charged region. The positively charged patch located on the surface opposite from the active site is highlighted with a black ellipse. (C) Detailed view of the sulfate binding site in TtCas6A-R1 product RNA complex. The sulfate ion and neighboring amino acid residues are shown in stick format.

REFERENCES

Adams P D, Afonine P V, Bunkóczi G, Chen V B, Davis I W, Echols N, Headd J J, Hung L-W, Kapral G J, Grosse-Kunstleve R W, McCoy A J, Moriarty N W, Oeffner R, Read R J, Richardson D C, Richardson J S, Terwilliger T C & Zwart P H (2010) PHENIX: a comprehensive Python-based system for macromolecular structure solution. Acta Crystallogr D Biol Crystallogr 66: 213-221

Afonine P V, Grosse-Kunstleve R W, Echols N, Headd J J, Moriarty N W, Mustyakimov M, Terwilliger T C, Urzhumtsev A, Zwart P H & Adams P D (2012) Towards automated crystallographic structure refinement with phenix.refine. Acta Crystallogr D Biol Crystallogr 68: 352-367

Agari Y, Sakamoto K, Tamakoshi M, Oshima T, Kuramitsu S & Shinkai A (2010) Transcription profile of *Thermus thermophilus* CRISPR systems after phage infection. J Mol Biol 395: 270-281

Al-Attar S, Westra E R, van der Oost J & Brouns S J J (2011) Clustered regularly interspaced short palindromic repeats (CRISPRs): the hallmark of an ingenious antiviral defense mechanism in prokaryotes. Biol. Chem. 392: 277-289

Brouns S J J, Jore M M, Lundgren M, Westra E R, Slijkhuis R J H, Snijders A P L, Dickman M J, Makarova K S, Koonin E V & van der Oost J (2008) Small CRISPR RNAs guide antiviral defense in prokaryotes. Science 321: 960-964

Carte J, Wang R, Li H, Terns R M & Terns M P (2008) Cas6 is an endoribonuclease that generates guide RNAs for invader defense in prokaryotes. Genes Dev 22: 3489-3496

Ebihara A, Yao M, Masui R, Tanaka I, Yokoyama S & Kuramitsu S (2006) Crystal structure of hypothetical protein TTHB192 from *Thermus thermophilus* HB8 reveals a new protein family with an RNA recognition motif-like domain. Protein Sci 15: 1494-1499

Emsley P, Lohkamp B, Scott W G & Cowtan K (2010) Features and development of Coot. Acta Crystallogr D Biol Crystallogr 66: 486-501

Gesner E M, Schellenberg M J, Garside E L, George M M & Macmillan A M (2011) Recognition and maturation of effector RNAs in a CRISPR interference pathway. Nat Struct Mol Biol 18: 688-692

Gouet P, Courcelle E, Stuart DI & Métoz F (1999) ESPript: analysis of multiple sequence alignments in PostScript. Bioinformatics 15: 305-308

Grissa I, Vergnaud G & Pourcel C (2007) The CRISPRdb database and tools to display CRISPRs and to generate dictionaries of spacers and repeats. BMC Bioinformatics 8: 172

Hale C R, Zhao P, Olson S, Duff M O, Graveley B R, Wells L, Terns R M & Terns M P (2009) RNA-guided RNA cleavage by a CRISPR RNA-Cas protein complex. Cell 139: 945-956

Haurwitz R E, Jínek M, Wiedenheft B, Zhou K & Doudna J A (2010) Sequence- and structure-specific RNA processing by a CRISPR endonuclease. Science 329: 1355-1358

Haurwitz R E, Sternberg S H & Doudna J A (2012) Csy4 relies on an unusual catalytic dyad to position and cleave CRISPR RNA. EMBO J: 1-9

Holm L & Sander C (1995) Dali: a network tool for protein structure comparison. Trends Biochem Sci 20: 478-480

Jore M M, Lundgren M, van Duijn E, Bultema J B, Westra E R, Waghmare S P, Wiedenheft B, Pul U, Wurm R, Wagner R, Beijer M R, Barendregt A, Zhou K, Snijders A P L, Dickman M J, Doudna J A, Boekema E J, Heck A J R, van der Oost J & Brouns S J J (2011) Structural basis for CRISPR RNA-guided DNA recognition by Cascade. Nat Struct Mol Biol 18: 529-536

Juranek S, Eban T, Altuvia Y, Brown M, Morozov P, Tuschl T & Margalit H (2012) A genome-wide view of the expression and processing patterns of *Thermus thermophilus* HB8 CRISPR RNAs. RNA 18: 783-794

Kabsch W (2010) XDS. Acta Crystallogr D Biol Crystallogr 66: 125-132

Kunin V, Sorek R & Hugenholtz P (2007) Evolutionary conservation of sequence and secondary structures in CRISPR repeats. Genome Biol 8: R61

Lee H Y, Haurwitz R E, Apffel A, Zhou K, Smart B, Wenger C D, Laderman S, Bruhn L & Doudna J A (2013) RNA-protein analysis using a conditional CRISPR nuclease. Proc Natl Acad Sci USA Lintner N G, Kerou M, Brumfield S K, Graham S, Liu H, Naismith J H, Sdano M, Peng N, She Q, Copie V, Young M J, White M F & Lawrence C M (2011) Structural and functional characterization of an archaeal clustered regularly interspaced short palindromic repeat (CRISPR)-associated complex for antiviral defense (CASCADE). Journal of Biological Chemistry 286: 21643-21656

Makarova K S, Aravind L, Wolf Y I & Koonin E V (2011a) Unification of Cas protein families and a simple scenario for the origin and evolution of CRISPR-Cas systems. Biol Direct 6: 38

Makarova K S, Haft D H, Barrangou R, Brouns S J J, Charpentier E, Horvath P, Moineau S, Mojica F J M, Wolf Y I, Yakunin A F, van der Oost J & Koonin E V (2011b) Evolution and classification of the CRISPR-Cas systems. Nat Rev Microbiol 9: 467-477

Marraffini L A & Sontheimer E J (2010) CRISPR interference: RNA-directed adaptive immunity in bacteria and archaea. Nat Rev Genet 11: 181-190

McCoy A J, Grosse-Kunstleve R W, Adams P D, Winn M D, Storoni L C & Read R J (2007) Phasercrystallographic software. J Appl Crystallogr 40: 658-674

Morris R J, Perrakis A & Lamzin V S (2003) ARP/wARP and automatic interpretation of protein electron density maps. Meth Enzymol 374: 229-244

Sashital D G, Jínek M & Doudna J A (2011) An RNA-induced conformational change required for CRISPR RNA cleavage by the endoribonuclease Cse3. Nat Struct Mol Biol 18: 680-687

Serra M J, Lyttle M H, Axenson T J, Schadt C A & Turner D H (1993) RNA hairpin loop stability depends on closing base pair. Nucleic Acids Res 21: 3845-3849

Shao Y & Li H (2013) Recognition and Cleavage of a Nonstructured CRISPR RNA by Its Processing Endoribonuclease Cas6. Structure 21: 385-393

Sternberg S H, Haurwitz R E & Doudna J A (2012) Mechanism of substrate selection by a highly specific CRISPR endoribonuclease. RNA 18: 661-672

Terns M P & Terns R M (2011) CRISPR-based adaptive immune systems. Curr Opin Microbiol 14: 321-327

Terwilliger T C (2004) Using prime-and-switch phasing to reduce model bias in molecular replacement. Acta Crystallogr D Biol Crystallogr 60: 2144-2149

Velankar S, Alhroub Y, Best C, Caboche S, Conroy M J, Dana J M, Fernandez Montecelo M A, van Ginkel G, Golovin A, Gore S P, Gutmanas A, Haslam P, Hendrickx P M S, Heuson E, Hirshberg M, John M, Lagerstedt I, Mir S, Newman L E, Oldfield T J, et al (2011) PDBe: Protein Data Bank in Europe. Nucleic Acids Res 40: D445-D452

Vonrhein C, Blanc E, Roversi P & Bricogne G (2007) Automated structure solution with autoSHARP. Methods Mol Biol 364: 215-230

Wang R, Preamplume G, Terns M P, Terns R M & Li H (2011) Interaction of the Cas6 riboendonuclease with CRISPR RNAs: recognition and cleavage. Structure 19: 257-264

Wang R, Zheng H, Preamplume G, Shao Y & Li H (2012) The impact of CRISPR repeat sequence on structures of a Cas6 protein-RNA complex. Protein Sci 21: 405-417

Wiedenheft B, Lander G C, Zhou K, Jore M M, Brouns S J J, van der Oost J, Doudna JA & Nogales E (2011a) Structures of the RNA-guided surveillance complex from a bacterial immune system. Nature 477: 486-489

Wiedenheft B, Sternberg S H & Doudna JA (2012) RNA-guided genetic silencing systems in bacteria and archaea. Nature 482: 331-338

Wiedenheft B, van Duijn E, Bultema J B, Bultema J, Waghmare S P, Waghmare S, Zhou K, Barendregt A, Westphal W, Heck A J R, Heck A, Boekema E J, Boekema E, Dickman M J, Dickman M & Doudna JA (2011b) RNA-guided complex from a bacterial immune system enhances target recognition through seed sequence interactions. Proc Natl Acad Sci USA 108: 10092-10097

Zwart P H, Afonine P V, Grosse-Kunstleve R W, Hung L-W, Ioerger T R, McCoy A J, McKee E, Moriarty N W, Read R J, Sacchettini J C, Sauter N K, Storoni L C, Terwilliger T C & Adams P D (2008) Automated structure solution with the PHENIX suite. Methods Mol Biol 426: 419-435

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant Cas endoribonuclease comprising an amino acid sequence having at least 95% amino acid sequence identity to the amino acid sequence set forth in SEQ ID NO:19, wherein the endoribonuclease comprises an amino acid substitution at a histidine residue such that the variant Cas endoribonuclease is enzymatically inactive in the absence of imidazole, and wherein the variant Cas endoribonuclease is activatable in the presence of imidazole.

2. The variant Cas endoribonuclease of claim 1, wherein the amino acid substitution is a substitution at His37.

3. The variant Cas endoribonuclease of claim 1, wherein the variant Cas endoribonuclease comprises a moiety that provides a detectable signal.

4. The variant Cas endoribonuclease of claim 1, wherein the endoribonuclease is immobilized on an insoluble support.

5. The variant Cas endoribonuclease of claim 1, wherein the variant Cas endoribonuclease binds an RNA substrate comprising a nucleotide sequence selected from:

```
                                            (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';
```

```
                                                       (SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';

(SEQ ID NO: 6)
5'-CCCCAGUCACCUCGGGAGGGGACGGAAAC-3';

(SEQ ID NO: 7)
5'-GUUCCAAUUAAUCUUAAACCCUAUUAGGGAUUGAAAC-3';

(SEQ ID NO: 8)
5'-GUCGCCCCCACGCGGGGCGUGGAUUGAAAC-3';

(SEQ ID NO: 9)
5'-CCAGCCGCCUUCGGGCGGCUGUGUGUUGAAAC-3';

(SEQ ID NO: 10)
5'-GUCGCACUCUACAUGAGUGCGUGGAUUGAAAU-3';

(SEQ ID NO: 11)
5'-UGUCGCACCUUAUAUAGGUGCGUGGAUUGAAAU-3';
and (SEQ ID NO: 12)
5'-GUCGCGCCCCGCAUGGGCGCGUGGAUUGAAA-3'.
```

6. A kit for purifying a target RNA present in a mixed population of nucleic acids, the kit comprising:

the variant Cas endoribonuclease of claim 1.

7. The kit of claim 6, further comprising a recombinant expression vector comprising, in order from 5' to 3' and in operable linkage:

a) a nucleotide sequence encoding an RNA substrate that is specifically bound by the variant Cas endoribonuclease of claim 1; and b) a multiple cloning site suitable for insertion of a nucleic acid encoding the target RNA.

8. The kit of claim 7, wherein the nucleotide sequence encoding the RNA substrate is operably linked to a promoter.

9. The kit of claim 7, wherein the RNA substrate comprises a nucleotide sequence selected from:

```
                                                       (SEQ ID NO: 1)
5'-GUUGCAAGGGAUUGAGCCCCGUAAGGGGAUUGCGAC-3';

(SEQ ID NO: 2)
5'-GUUGCAAACCUCGUUAGCCUCGUAGAGGAUUGAAAC-3';

(SEQ ID NO: 3)
5'-GGAUCGAUACCCACCCCGAAGAAAAGGGGACGAGAAC-3';

(SEQ ID NO: 4)
5'-GUCGUCAGACCCAAAACCCCGAGAGGGGACGGAAAC-3';

(SEQ ID NO: 5)
5'-GAUAUAAACCUAAUUACCUCGAGAGGGGACGGAAAC-3';
```

```
                                                       (SEQ ID NO: 6)
5'-CCCCAGUCACCUCGGGAGGGGACGGAAAC-3';

(SEQ ID NO: 7)
5'-GUUCCAAUUAAUCUUAAACCCUAUUAGGGAUUGAAAC-3';

(SEQ ID NO: 8)
5'-GUCGCCCCCACGCGGGGCGUGGAUUGAAAC-3';

(SEQ ID NO: 9)
5'-CCAGCCGCCUUCGGGCGGCUGUGUGUUGAAAC-3';

(SEQ ID NO: 10)
5'-GUCGCACUCUACAUGAGUGCGUGGAUUGAAAU-3';

(SEQ ID NO: 11)
5'-UGUCGCACCUUAUAUAGGUGCGUGGAUUGAAAU-3';
and (SEQ ID NO: 12)
5'-GUCGCGCCCCGCAUGGGCGCGUGGAUUGAAA-3'.
```

10. The kit of claim 7, wherein the recombinant expression vector comprises, inserted into the multiple cloning site, a nucleotide sequence encoding the target RNA.

11. A method of isolating a target RNA present in a mixed population of nucleic acids, the method comprising:

a) contacting a mixed population of nucleic acids with the variant Cas endoribonuclease of claim 1, where the variant Cas endoribonuclease is immobilized on an insoluble support, wherein the mixed population of nucleic acids comprises a tagged target RNA comprising a recognition nucleotide sequence that is specifically bound by the immobilized variant Cas endoribonuclease, forming a tagged target RNA-immobilized variant Cas endoribonuclease complex, wherein said contacting is carried out in a binding solution lacking imidazole;

b) adding imidazole to the binding solution to a final concentration of from about 100 mM to about 500 mM, thereby forming a reactivation solution that enzymatically reactivates the immobilized variant Cas endoribonuclease, wherein the reactivated immobilized variant Cas endoribonuclease cleaves the target RNA from the tag; and c) collecting the released target RNA.

12. The method of claim 11, further comprising a wash step carried out after step (a) and before step (b).

13. A method of isolating a polypeptide that binds a target RNA, the method comprising:

a) contacting an immobilized complex with a liquid solution comprising a polypeptide that binds the target RNA, wherein the immobilized complex comprises the variant Cas endoribonuclease of claim 1 and a tagged target RNA comprising a recognition nucleotide sequence that is specifically bound by the variant Cas endoribonuclease, wherein said contacting results in binding of the polypeptide to the target RNA, wherein said contacting is carried out in a binding solution lacking imidazole; and b) eluting the bound polypeptide.

\* \* \* \* \*

```
                            SEQUENCE LISTING

<160> NUMBER OF SEQ ID NOS: 60

<210> SEQ ID NO 1
<211> LENGTH: 36
<212> TYPE: RNA
<213> ORGANISM: Artificial sequence
<220> FEATURE:
<223> OTHER INFORMATION: Synthetic nucleic acid sequence

<400> SEQUENCE: 1
guugcaaggg auugagcccc guaaggggau ugcgac                              36

<210> SEQ ID NO 2
<211> LENGTH: 36
<212> TYPE: RNA
<213> ORGANISM: Artificial sequence
<220> FEATURE:
<223> OTHER INFORMATION: Synthetic nucleic acid sequence

<400> SEQUENCE: 2
guugcaaacc ucguuagccu cguagaggau ugaaac                              36

<210> SEQ ID NO 3
<211> LENGTH: 37
<212> TYPE: RNA
<213> ORGANISM: Artificial sequence
<220> FEATURE:
<223> OTHER INFORMATION: Synthetic nucleic acid sequence

<400> SEQUENCE: 3
ggaucgauac ccaccccgaa gaaaagggga cgagaac                             37

<210> SEQ ID NO 4
<211> LENGTH: 36
<212> TYPE: RNA
<213> ORGANISM: Artificial sequence
<220> FEATURE:
<223> OTHER INFORMATION: Synthetic nucleic acid sequence

<400> SEQUENCE: 4
gucgucagac ccaaaacccc gagaggggac ggaaac                              36

<210> SEQ ID NO 5
<211> LENGTH: 36
<212> TYPE: RNA
<213> ORGANISM: Artificial sequence
<220> FEATURE:
<223> OTHER INFORMATION: Synthetic nucleic acid sequence

<400> SEQUENCE: 5
gauauaaacc uaauuaccuc gagaggggac ggaaac                              36

<210> SEQ ID NO 6
<211> LENGTH: 29
<212> TYPE: RNA
<213> ORGANISM: Artificial sequence
<220> FEATURE:
<223> OTHER INFORMATION: Synthetic nucleic acid sequence

<400> SEQUENCE: 6
ccccagucac cucgggaggg gacggaaac                                      29
```

<210> SEQ ID NO 7
<211> LENGTH: 37
<212> TYPE: RNA
<213> ORGANISM: Artificial sequence
<220> FEATURE:
<223> OTHER INFORMATION: Synthetic nucleic acid sequence

<400> SEQUENCE: 7
guuccaauua aucuuaaacc cuauuaggga uugaaac                    37

<210> SEQ ID NO 8
<211> LENGTH: 32
<212> TYPE: RNA
<213> ORGANISM: Artificial sequence
<220> FEATURE:
<223> OTHER INFORMATION: Synthetic nucleic acid sequence

<400> SEQUENCE: 8
gucgcccccc acgcggggc guggauugaa ac                          32

<210> SEQ ID NO 9
<211> LENGTH: 32
<212> TYPE: RNA
<213> ORGANISM: Artificial sequence
<220> FEATURE:
<223> OTHER INFORMATION: Synthetic nucleic acid sequence

<400> SEQUENCE: 9
ccagccgccu ucgggcggcu guguguugaa ac                         32

<210> SEQ ID NO 10
<211> LENGTH: 32
<212> TYPE: RNA
<213> ORGANISM: Artificial sequence
<220> FEATURE:
<223> OTHER INFORMATION: Synthetic nucleic acid sequence

<400> SEQUENCE: 10
gucgcacucu acaugagugc guggauugaa au                         32

<210> SEQ ID NO 11
<211> LENGTH: 33
<212> TYPE: RNA
<213> ORGANISM: Artificial sequence
<220> FEATURE:
<223> OTHER INFORMATION: Synthetic nucleic acid sequence

<400> SEQUENCE: 11
ugucgcaccu uauauaggug cguggauuga aau                        33

<210> SEQ ID NO 12
<211> LENGTH: 32
<212> TYPE: RNA
<213> ORGANISM: Artificial sequence
<220> FEATURE:
<223> OTHER INFORMATION: Synthetic nucleic acid sequence

<400> SEQUENCE: 12
gucgcgcccc gcaugggggcg cguggauuga aa                        32

<210> SEQ ID NO 13
<211> LENGTH: 227
<212> TYPE: PRT
<213> ORGANISM: Desulfovibrio vulgaris str. Hildenborough

<400> SEQUENCE: 13

```
Met Thr His Gly Ala Val Lys Thr Tyr Gly Ile Arg Leu Arg Val Trp
1               5                   10                  15

Gly Asp Tyr Ala Cys Phe Thr Arg Pro Glu Met Lys Val Glu Arg Val
            20                  25                  30

Ser Tyr Asp Val Met Pro Ser Ala Ala Arg Gly Ile Leu Glu Ala
        35                  40                  45

Ile His Trp Lys Pro Ala Ile Arg Trp Ile Val Asp Arg Ile His Val
    50                  55                  60

Leu Arg Pro Ile Val Phe Asp Asn Val Arg Arg Asn Glu Val Ser Ser
65                  70                  75                  80

Lys Ile Pro Lys Pro Asn Pro Ala Thr Ala Met Arg Asp Arg Lys Pro
                85                  90                  95

Leu Tyr Phe Leu Val Asp Asp Gly Ser Asn Arg Gln Gln Arg Ala Ala
                100                 105                 110

Thr Leu Leu Arg Asn Val Asp Tyr Val Ile Glu Ala His Phe Glu Leu
            115                 120                 125

Thr Asp Lys Ala Gly Ala Glu Asp Asn Ala Gly Lys His Leu Asp Ile
130                 135                 140

Phe Arg Arg Arg Ala Arg Ala Gly Gln Ser Phe Gln Gln Pro Cys Leu
145                 150                 155                 160

Gly Cys Arg Glu Phe Pro Ala Ser Phe Glu Leu Leu Glu Gly Asp Val
                165                 170                 175

Pro Leu Ser Cys Tyr Ala Gly Glu Lys Arg Asp Leu Gly Tyr Met Leu
            180                 185                 190

Leu Asp Ile Asp Phe Glu Arg Asp Met Thr Pro Leu Phe Phe Lys Ala
        195                 200                 205

Val Met Glu Asp Gly Val Ile Thr Pro Pro Ser Arg Thr Ser Pro Glu
    210                 215                 220

Val Arg Ala
225
```

<210> SEQ ID NO 14
<211> LENGTH: 15
<212> TYPE: RNA
<213> ORGANISM: Artificial sequence
<220> FEATURE:
<223> OTHER INFORMATION: Synthetic nucleic acid sequence

<400> SEQUENCE: 14
gccccguuag gggau                                                15

<210> SEQ ID NO 15
<211> LENGTH: 30
<212> TYPE: RNA
<213> ORGANISM: Artificial sequence
<220> FEATURE:
<223> OTHER INFORMATION: Synthetic nucleic acid sequence

<400> SEQUENCE: 15
guugcaaggg auugagcccc guuaggggau                                30

<210> SEQ ID NO 16
<211> LENGTH: 267
<212> TYPE: PRT
<213> ORGANISM: Meiothermus silvanus DSM 9946

<400> SEQUENCE: 16

Met Met Leu Ala Ala Leu Val Leu Pro Leu Glu Gly Gln Ala Arg Pro

```
               1               5                  10                 15
            Asp Pro Asp Gly Trp Arg Gly Leu Val Tyr Gly Leu Leu Lys Glu Ile
                            20                 25                 30

Asp Pro Glu Leu His Thr Ala Gln His Asn Pro Phe Ser Leu Gly Leu
                            35                 40                 45

Gly Gly Ala Glu Gly Gln Trp Trp Val Arg Ile Ala Leu Leu Glu Glu
             50                 55                 60

Gly Leu Tyr Ala Arg Leu Ser Pro His Leu Phe Gly Leu Val Gly Gln
             65                 70                 75                 80

Ser Val Lys Leu Lys Glu Pro Phe Arg Val Arg Ala Val Leu Gln Glu
                            85                 90                 95

Glu His Pro Trp Ala Ser Leu Ser Thr Tyr Pro Arg Leu Phe Gln Gly
                            100                105                110

Gln Ala Ser Pro Ser Leu Gly Leu Gln Phe Ala Ser Pro Thr Phe Phe
                            115                120                125

Arg Arg Lys Gly Asn Ser Tyr Pro Leu Pro Glu Pro Lys Leu Val Phe
                            130                135                140

Asp Ser Leu Thr Gln Arg Trp Asn Ala Phe Ala Pro Val Lys Val Pro
            145                150                155                160

Pro Glu Met Ala Glu Thr Trp Glu Arg Val Thr Ile Thr Arg Leu Gln
                            165                170                175

Gly His Thr Gln Ala Ile Arg Pro Asn Pro Asp Glu Arg Gly Val Gly
                            180                185                190

Phe Val Gly Arg Val Val Tyr His Leu Pro Ala Ala Lys Pro Thr Glu
                            195                200                205

Ala Gln Trp Met Gln Ala Leu Gly Arg Phe Ala Phe Tyr Ala Gly Val
                            210                215                220

Gly Ala Lys Thr Ser Leu Gly Phe Gly Arg Val Arg Gly Phe Asp Pro
            225                230                235                240

Ile Leu Lys Glu Glu Ser Ala Asn Gly Arg Leu Asp Ala Glu Asp Ser
                            245                250                255

Ser Ser Leu Ala Thr Pro Gln Asp Pro Gly Ala
                            260                265

<210> SEQ ID NO 17
<211> LENGTH: 267
<212> TYPE: PRT
<213> ORGANISM: Meiothermus silvanus DSM 9946

<400> SEQUENCE: 17

Met Met Leu Ala Ala Leu Val Leu Pro Leu Glu Gly Gln Ala Arg Pro
            1               5                  10                 15

Asp Pro Asp Gly Trp Arg Gly Leu Val Tyr Gly Leu Leu Lys Glu Ile
                            20                 25                 30

Asp Pro Glu Leu His Thr Ala Gln His Asn Pro Phe Ser Leu Gly Leu
                            35                 40                 45

Gly Gly Ala Glu Gly Gln Trp Trp Val Arg Ile Ala Leu Leu Glu Glu
             50                 55                 60

Gly Leu Tyr Ala Arg Leu Ser Pro His Leu Phe Gly Leu Val Gly Gln
             65                 70                 75                 80

Ser Val Lys Leu Lys Glu Pro Phe Arg Val Arg Ala Val Leu Gln Glu
                            85                 90                 95

Glu His Pro Trp Ala Ser Leu Ser Thr Tyr Pro Arg Leu Phe Gln Gly
                            100                105                110
```

```
Gln Ala Ser Pro Ser Leu Gly Leu Gln Phe Ala Ser Pro Thr Phe Phe
            115                 120                 125

Arg Arg Lys Gly Asn Ser Tyr Pro Leu Pro Glu Pro Lys Leu Val Phe
130                 135                 140

Asp Ser Leu Thr Gln Arg Trp Asn Ala Phe Ala Pro Val Lys Val Pro
145                 150                 155                 160

Pro Glu Met Ala Glu Thr Trp Glu Arg Val Thr Ile Thr Arg Leu Gln
                165                 170                 175

Gly His Thr Gln Ala Ile Arg Pro Asn Pro Asp Glu Arg Gly Val Gly
            180                 185                 190

Phe Val Gly Arg Val Val Tyr His Leu Pro Ala Ala Lys Pro Thr Glu
            195                 200                 205

Ala Gln Trp Met Gln Ala Leu Gly Arg Phe Ala Phe Tyr Ala Gly Val
            210                 215                 220

Gly Ala Lys Thr Ser Leu Gly Phe Gly Arg Val Arg Gly Phe Asp Pro
225                 230                 235                 240

Ile Leu Lys Glu Glu Ser Ala Asn Gly Arg Leu Asp Ala Glu Asp Ser
                245                 250                 255

Ser Ser Leu Ala Thr Pro Gln Asp Pro Gly Ala
            260                 265

<210> SEQ ID NO 18
<211> LENGTH: 262
<212> TYPE: PRT
<213> ORGANISM: Meiothermus ruber DSM 1279

<400> SEQUENCE: 18

Met Ile Leu Ala Ala Leu Ile Leu Pro Leu Glu Gly Pro Thr Arg Pro
1               5                   10                  15

Asp Pro Asp Gly Trp Arg Gly Leu Val Tyr Gly Leu Leu Lys Glu Ile
            20                  25                  30

Asp Pro Glu Leu His Ala Ala Gln His Asn Pro Phe Ser Leu Gly Leu
        35                  40                  45

Gly Gly Ala Leu Gly Gln Trp Trp Val Arg Ile Ala Phe Leu Glu Glu
    50                  55                  60

Gly Leu Tyr Ala Arg Leu Ser Pro His Leu Phe Gly Leu Ala Gly Gln
65                  70                  75                  80

Thr Val Arg Leu Lys Glu Ala Phe Gln Val Arg Ala Val Leu Gln Glu
                85                  90                  95

Ala His Pro Trp Ala Gly Val Ser Thr Tyr Pro Lys Leu Phe Gln Gly
            100                 105                 110

Gln Ala Thr Ala Ser Leu Gly Leu Gln Phe Ala Ser Pro Thr Phe Phe
            115                 120                 125

Arg Arg Lys Gly His Ser Tyr Pro Leu Pro Glu Pro Arg Leu Val Phe
130                 135                 140

Glu Ser Leu Thr Gln Arg Trp Asn Ala Phe Ala Pro Val Lys Val Pro
145                 150                 155                 160

Gln Glu Val Gln Glu Ala Trp Glu Arg Leu Leu Val Gly Gln Phe Gln
                165                 170                 175

Gly Arg Thr His His Ile Ala Pro Asn Gln Asp Glu Arg Gly Val Gly
            180                 185                 190

Phe Val Gly Arg Val Val Tyr Tyr Leu Pro Lys Ala Ser Pro Thr Glu
            195                 200                 205

Ala Gln Trp Leu Gln Ala Leu Gly Arg Phe Ala Phe Tyr Ala Gly Val
            210                 215                 220
```

```
Gly Ala Lys Thr Ser Leu Gly Phe Gly Arg Val Arg Met Phe Asp Pro
225                 230                 235                 240

Leu Gln Gln Glu Arg Pro Asp Glu Ser Glu Gln Gly Ala Leu Thr
            245                 250                 255

Gly Thr Val Gly Gly Val
            260

<210> SEQ ID NO 19
<211> LENGTH: 239
<212> TYPE: PRT
<213> ORGANISM: Thermus thermophilus HB8

<400> SEQUENCE: 19

Met Val Leu Ala Ala Leu Val Leu Val Leu Glu Gly Glu Gly Leu Pro
1               5                   10                  15

Glu Pro Leu Gly Leu Arg Gly Phe Phe Tyr Gly Leu Leu Arg Glu Val
            20                  25                  30

Ala Pro Glu Val His Asp Gln Gly Glu Asn Pro Phe Ala Leu Gly Phe
        35                  40                  45

Gly Gly Arg Glu Gly Ala Ala Trp Ala Arg Val Ser Leu Leu Val Glu
50                  55                  60

Gly Leu Tyr Ala Arg Leu Ala Pro Arg Leu Tyr Ala Leu Glu Gly Glu
65                  70                  75                  80

Glu Val Arg Leu Gly Pro Pro Phe Arg Val Arg Ala Val Leu Gln Glu
                85                  90                  95

Gly His Pro Trp Ala Gly Val Ser Thr Tyr Pro Arg Leu Phe Gln Gly
            100                 105                 110

Pro Pro Ser Arg Asp Leu Ala Leu Arg Phe Ala Ser Pro Thr Phe Phe
        115                 120                 125

Arg Arg Lys Gly Val His Tyr Pro Val Pro Glu Pro Arg Leu Val Leu
130                 135                 140

Glu Ser Leu Leu Arg Arg Leu Glu Ala Phe Gly Pro Leu Lys Ala Pro
145                 150                 155                 160

Glu Gly Val Arg Glu Ala Leu Leu Glu Arg Thr Thr Val Arg Ser Leu
                165                 170                 175

Glu Gly Arg Thr Leu Pro Ala Arg Thr Glu Val Asp Thr Ala Gly Phe
            180                 185                 190

Val Gly Arg Val Val Tyr His Leu Pro Arg Ala Thr Glu Glu Glu Ala
        195                 200                 205

Leu Trp Leu Ser Ala Leu Gly Arg Phe Ala Phe Tyr Ser Gly Val Gly
    210                 215                 220

Ala Lys Thr Ser Leu Gly Tyr Gly Arg Ala Arg Ala Glu Ser Ala
225                 230                 235

<210> SEQ ID NO 20
<211> LENGTH: 239
<212> TYPE: PRT
<213> ORGANISM: Thermus thermophilus JL-18

<400> SEQUENCE: 20

Met Val Leu Ala Ala Leu Val Leu Val Leu Glu Gly Glu Gly Leu Pro
1               5                   10                  15

Glu Pro Leu Gly Leu Arg Gly Phe Phe Tyr Gly Leu Leu Arg Glu Val
            20                  25                  30

Ala Pro Glu Val His Asp Gln Gly Glu Asn Pro Phe Ala Leu Gly Phe
        35                  40                  45
```

```
Gly Gly Arg Glu Gly Ala Ser Trp Ala Arg Val Ser Leu Leu Arg Glu
        50                  55                  60

Glu Leu Tyr Ala Arg Leu Ala Pro Arg Leu Tyr Ala Leu Glu Gly Glu
 65                  70                  75                  80

Glu Val Arg Leu Gly Pro Pro Phe Arg Val Arg Ala Val Leu Gln Glu
                85                  90                  95

Gly His Pro Trp Ala Gly Val Ser Thr Tyr Pro Arg Leu Phe Gln Gly
            100                 105                 110

Pro Pro Ser Arg Asp Leu Ala Leu Arg Phe Ala Ser Pro Thr Phe Phe
            115                 120                 125

Arg Arg Lys Gly Val His Tyr Pro Val Pro Glu Pro Arg Leu Val Leu
            130                 135                 140

Glu Ser Leu Leu Arg Arg Leu Glu Ala Phe Gly Pro Leu Lys Ala Pro
145                 150                 155                 160

Glu Gly Val Arg Glu Ala Leu Leu Glu Arg Thr Thr Val Arg Ser Leu
                165                 170                 175

Glu Gly Arg Thr Leu Pro Ala Arg Thr Glu Val Asp Thr Ala Gly Phe
            180                 185                 190

Val Gly Arg Val Val Tyr His Leu Pro Arg Ala Thr Glu Glu Ala
            195                 200                 205

Leu Trp Leu Ser Ala Leu Gly Arg Phe Ala Phe Tyr Ser Gly Val Gly
    210                 215                 220

Ala Lys Thr Ser Leu Gly Tyr Gly Arg Ala Arg Ala Glu Ser Pro
225                 230                 235

<210> SEQ ID NO 21
<211> LENGTH: 236
<212> TYPE: PRT
<213> ORGANISM: Thermus sp. CCB_US3_UF1

<400> SEQUENCE: 21

Met Leu Ala Ala Leu Val Leu Thr Leu Glu Gly Glu Ala Pro Pro Glu
  1               5                  10                  15

Pro Arg Gly Leu Arg Gly Phe Phe Tyr Gly Leu Leu Gln Glu Val Ala
                20                  25                  30

Pro Glu Val His Asp Gln Gly Glu Asn Pro Phe Ala Leu Gly Phe Gly
            35                  40                  45

Gly Lys Glu Gly Ala Tyr Trp Ala Arg Phe Ser Leu Leu Gln Glu Gly
        50                  55                  60

Leu Tyr Ala Arg Leu Ala Pro Arg Leu Phe Ala Leu Glu Gly Lys Glu
 65                  70                  75                  80

Val Arg Leu Gly Lys Pro Phe Arg Val Arg Gly Val Leu Gln Glu Gly
                85                  90                  95

His Pro Trp Ala Gly Val Ser Thr Tyr Ala Arg Leu Phe Gln Gly Glu
            100                 105                 110

Ala Leu Pro Asp Leu Pro Leu Arg Phe Ala Ser Pro Thr Phe Phe Arg
            115                 120                 125

Arg Lys Gly Val His Tyr Pro Leu Pro Glu Pro Arg Leu Val Val Glu
            130                 135                 140

Ser Leu Leu Arg Arg Leu Glu Ala Phe Gly Pro Leu Lys Ala Pro Glu
145                 150                 155                 160

Gly Val Arg Glu Ala Leu Leu Glu Arg Thr Thr Val Arg Trp Phe Glu
                165                 170                 175

Gly Lys Thr Leu Lys Ala Glu Thr Glu Val Glu Ala Val Gly Phe Val
```

```
                     180                 185                 190
Gly Lys Val Val Tyr His Leu Pro Arg Ala Thr Glu Glu Ala Arg
                 195                 200                 205

Trp Leu Gln Ala Leu Gly Arg Phe Ala Phe Tyr Ser Gly Val Gly Ala
            210                 215                 220

Lys Thr Gly Leu Gly Tyr Gly Arg Ala Arg Val Gly
225                 230                 235
```

<210> SEQ ID NO 22
<211> LENGTH: 247
<212> TYPE: PRT
<213> ORGANISM: Thermus aquaticus Y51MC23

<400> SEQUENCE: 22

```
Met Val Leu Val Ala Leu Val Leu Val Leu Glu Gly Glu Gly Pro Pro
1               5                   10                  15

Glu Pro Leu Gly Leu Arg Gly Phe Phe Tyr Thr Leu Leu Lys Glu Ala
            20                  25                  30

Phe Pro Glu Leu His Asp Gln Gly Glu Asn Pro Phe Ala Leu Gly Phe
        35                  40                  45

Gly Leu Arg Gly Glu Pro Trp Ala Arg Val Ser Leu Leu Arg Glu
    50                  55                  60

Asp Leu Tyr Gly Arg Leu Ser Pro Ala Leu Phe Gly Leu Glu Gly Arg
65                  70                  75                  80

Glu Val Arg Leu Gly Arg Leu Phe Arg Val Arg Ala Val Leu Gln Glu
                85                  90                  95

Gly His Pro Trp Ala Gly Leu Thr Thr Tyr Ala Arg Leu Phe Gln Gly
            100                 105                 110

Pro His Ser Pro Asn Leu Pro Leu Arg Phe Tyr Ser Pro Thr Phe Phe
        115                 120                 125

Arg Arg Lys Gly Val Gln Tyr Pro Leu Pro Glu Pro Arg Leu Val Leu
    130                 135                 140

Glu Ser Leu Leu Arg Arg Leu Glu Ala Phe Gly Pro Leu Lys Ala Pro
145                 150                 155                 160

Gln Glu Val Arg Glu Ala Leu Leu Glu Arg Thr Thr Val Arg Phe Leu
                165                 170                 175

Glu Gly Arg Thr Gln Met Ala Arg Thr Glu Val Asp Thr Val Gly Phe
            180                 185                 190

Val Gly Lys Val Val Tyr His Leu Pro Lys Ala Thr Glu Glu Glu Ala
        195                 200                 205

Leu Trp Leu Ser Ala Leu Gly Arg Tyr Ala Phe Phe Ser Gly Val Gly
    210                 215                 220

Ala Lys Thr Ser Leu Gly Tyr Gly Leu Ala Arg Ala Phe Thr Gln Val
225                 230                 235                 240

Gly Pro Gln Asp Ala Glu Thr
                245
```

<210> SEQ ID NO 23
<211> LENGTH: 251
<212> TYPE: PRT
<213> ORGANISM: Marinithermus hydrothermalis DSM 14884

<400> SEQUENCE: 23

```
Met Leu Leu Ala Ala Leu Val Leu Pro Leu Glu Gly Pro Asp Arg Pro
1               5                   10                  15

Gln Pro Leu His Ala Arg Gly Trp Val Tyr Arg Leu Leu Arg Glu Ala
```

-continued

```
                20                  25                  30
Ala Pro Glu Ile His Asp Ala Glu Gly Pro Lys Pro Phe Thr Val Gly
            35                  40                  45

Val Gly Gly Arg Pro Asn Ala Val Trp Val Arg Leu Thr Cys Leu Ala
 50                  55                  60

Glu Val Tyr Ala Ala Leu Ser Pro Arg Leu Trp Ser Gln Val Gly
 65                  70                  75                  80

Leu Glu Val Arg Leu Gly Glu Asp Thr Tyr Arg Ile Lys Ala Val Leu
                85                  90                  95

Glu Ala Glu His Pro Trp Ala Gly Leu Ala Thr Trp Pro Arg Leu Phe
            100                 105                 110

Gln Gly Glu Ala Gly Pro Asp Leu Gly Leu Glu Phe Ala Ser Pro Thr
        115                 120                 125

Phe Phe Arg Arg Gln Gly Ala Asn Tyr Pro Leu Pro Glu Pro Arg Leu
    130                 135                 140

Val Leu Gly Ser Leu Ile Glu Arg Trp Asn Ala His Ala Pro Thr Pro
145                 150                 155                 160

Val Pro Pro Glu Val Ala Glu Arg Leu Val Glu Ala Thr Thr Leu Arg
                165                 170                 175

Tyr Leu Lys Gly His Thr Val Ser Ala Val Gly His Asp Arg Thr Val
            180                 185                 190

Gly Phe Arg Gly Arg Val Thr Tyr His Leu Pro Arg Ala Ser Thr Glu
        195                 200                 205

Glu Ala Arg Trp Leu Ala Ala Leu Gly Arg Phe Ala Phe Ser Gly
    210                 215                 220

Val Gly Ala Lys Thr Thr Leu Gly Phe Gly Gln Val Arg Pro Tyr Pro
225                 230                 235                 240

Leu Leu Ala Pro Ser Ala Ala Pro Pro Gly Pro
                245                 250

<210> SEQ ID NO 24
<211> LENGTH: 264
<212> TYPE: PRT
<213> ORGANISM: Thermus thermophilus HB8

<400> SEQUENCE: 24

Met Pro Gln Ala Val Val Leu Glu Leu Val Gly Glu Lys Pro Pro Leu
 1               5                  10                  15

Tyr Pro Ala Arg Tyr Ala His Gly Leu Phe Phe Ala Leu Leu Ser Arg
            20                  25                  30

Val Ser Pro Glu Leu Ala Gln Lys Leu His Glu Ala Pro Arg Lys Pro
        35                  40                  45

Phe Thr Leu Ala Pro Leu Pro Arg Ala Gly Pro Glu Gly Ala Thr Leu
    50                  55                  60

Lys Gly Thr Leu Arg Leu Arg Leu Thr Thr Leu Asp Asp Gly Leu Phe
 65                  70                  75                  80

Ala Pro Phe Leu Arg Ala Leu Leu Glu Ala Ala Pro Asp Gly Leu Pro
                85                  90                  95

Leu Gly Asp Ser Ser Tyr Arg Leu Ala Arg Val Leu Ala Thr Arg Glu
            100                 105                 110

Gly His Pro Leu Ala Gly Ala Thr Ser Trp Glu Glu Leu Lys Glu Ala
        115                 120                 125

Pro Lys Arg Glu Lys Ala Thr Phe Arg Phe Leu Thr Pro Thr Val Phe
    130                 135                 140
```

Ala Thr Ser Lys Pro Gly Gly Arg Thr Arg Tyr Thr Pro Leu Pro Asp
145                 150                 155                 160

Pro Arg Leu Ile Ala Gly Ser Leu Leu Asp Lys Trp Gln Ala His Ser
            165                 170                 175

Pro Phe Pro Tyr Asn Pro Lys Glu Glu Ala Ala Leu Arg Glu Leu Phe
            180                 185                 190

Glu Leu Asp Leu Glu Val Ala Gly Phe Arg Asn Leu Arg Phe His Arg
            195                 200                 205

Val Gln Ala Gly Lys Gly Phe Phe Pro Gly Phe Thr Gly Glu Ala Thr
    210                 215                 220

Leu Arg Leu Trp Ser Gln Ser Leu Glu Ala Gln Glu Ala Leu Gly Arg
225                 230                 235                 240

Leu His Ala Leu Ala Phe Phe Ser Gly Val Gly Ala Lys Thr Pro Tyr
            245                 250                 255

Gly Met Gly Leu Ala Val Pro Leu
            260

<210> SEQ ID NO 25
<211> LENGTH: 264
<212> TYPE: PRT
<213> ORGANISM: Thermus thermophilus HB27

<400> SEQUENCE: 25

Met Pro Gln Ala Val Val Leu Glu Leu Val Gly Glu Lys Pro Pro Leu
1               5                   10                  15

Tyr Pro Ala Arg Tyr Ala His Gly Leu Phe Phe Ala Leu Leu Ser Arg
                20                  25                  30

Val Ser Pro Glu Leu Ala Gln Lys Leu His Glu Ala Pro Arg Lys Pro
            35                  40                  45

Phe Thr Leu Ala Pro Leu Pro Arg Ala Gly Pro Glu Gly Ala Thr Leu
    50                  55                  60

Lys Gly Thr Leu Arg Leu Arg Leu Thr Thr Leu Asp Asp Gly Leu Phe
65                  70                  75                  80

Ala Pro Phe Leu Arg Ala Leu Leu Glu Ala Ala Pro Asp Gly Leu Pro
                85                  90                  95

Leu Gly Asp Ser Ser Tyr Arg Leu Ala Arg Val Leu Ala Thr Arg Glu
            100                 105                 110

Gly His Pro Leu Ala Gly Ala Thr Ser Trp Glu Glu Leu Lys Glu Ala
            115                 120                 125

Pro Lys Arg Glu Lys Val Thr Phe Arg Phe Leu Thr Pro Thr Val Phe
    130                 135                 140

Ala Thr Ser Lys Pro Gly Gly Arg Thr Arg Tyr Thr Pro Leu Pro Asp
145                 150                 155                 160

Pro Arg Leu Ile Ala Gly Ser Leu Leu Asp Lys Trp Gln Ala His Ser
            165                 170                 175

Pro Phe Pro Tyr Asn Pro Lys Glu Glu Ala Ala Leu Arg Gly Leu Phe
            180                 185                 190

Glu Leu Asp Leu Glu Val Ala Gly Phe Arg Asn Leu Arg Phe His Arg
            195                 200                 205

Val Gln Ala Gly Lys Gly Phe Phe Pro Gly Phe Thr Gly Glu Met Thr
    210                 215                 220

Leu Arg Leu Trp Ser Gln Ser Leu Glu Ala Arg Glu Ala Leu Gly Arg
225                 230                 235                 240

Leu His Ala Leu Ala Phe Phe Ser Gly Val Gly Ala Lys Thr Pro Tyr
            245                 250                 255

Gly Met Gly Leu Ala Val Pro Leu
            260

<210> SEQ ID NO 26
<211> LENGTH: 264
<212> TYPE: PRT
<213> ORGANISM: Thermus thermophilus SG0.5JP17-16

<400> SEQUENCE: 26

Met Pro Gln Ala Val Val Leu Glu Leu Val Gly Glu Lys Pro Pro Leu
1               5                   10                  15

Tyr Pro Gly Arg Tyr Ala His Gly Leu Phe Phe Ala Leu Leu Ser Arg
            20                  25                  30

Val Ser Pro Glu Leu Ala Gln Lys Leu His Glu Ala Pro Arg Lys Pro
        35                  40                  45

Phe Thr Leu Ala Pro Leu Pro Arg Val Gly Pro Glu Gly Ala Thr Leu
    50                  55                  60

Lys Gly Ile Leu Arg Leu Arg Leu Thr Ala Leu Asp Asp Gly Leu Phe
65                  70                  75                  80

Ala Pro Phe Leu Arg Ala Leu Leu Glu Ala Ala Pro Asp Gly Leu Pro
                85                  90                  95

Leu Gly Asp Ser Ser Tyr Arg Leu Ala Arg Val Leu Ala Thr Arg Glu
            100                 105                 110

Gly His Pro Leu Ala Gly Ala Thr Ser Trp Glu Leu Lys Glu Ala
        115                 120                 125

Pro Lys Arg Glu Lys Ala Thr Phe Arg Phe Leu Thr Pro Thr Val Phe
    130                 135                 140

Ala Thr Ser Lys Pro Gly Gly Arg Thr Arg Tyr Thr Pro Leu Pro Asp
145                 150                 155                 160

Pro Arg Leu Ile Ala Gly Ser Leu Leu Asp Lys Trp Gln Ala His Ser
                165                 170                 175

Pro Phe Pro Tyr Asn Pro Lys Glu Glu Ala Ala Leu Arg Glu Leu Phe
            180                 185                 190

Glu Leu Asp Leu Glu Val Ala Gly Phe Arg Asn Leu Arg Phe His Arg
        195                 200                 205

Val Gln Ala Gly Lys Gly Phe Phe Pro Gly Phe Thr Gly Glu Ala Thr
    210                 215                 220

Leu Arg Leu Trp Ser Gln Ser Leu Glu Ala Gln Ala Leu Gly Arg
225                 230                 235                 240

Leu His Ala Leu Ala Phe Phe Ser Gly Val Gly Ala Lys Thr Pro Tyr
                245                 250                 255

Gly Met Gly Leu Ala Val Pro Leu
            260

<210> SEQ ID NO 27
<211> LENGTH: 264
<212> TYPE: PRT
<213> ORGANISM: Thermus thermophilus JL-18

<400> SEQUENCE: 27

Met Pro Gln Ala Val Val Leu Glu Leu Val Gly Glu Glu Ser Pro Leu
1               5                   10                  15

Tyr Pro Ala Arg Tyr Ala His Gly Leu Phe Phe Ala Leu Leu Ser Arg
            20                  25                  30

Val Ser Pro Glu Leu Ala Gln Lys Leu His Glu Ala Pro Arg Lys Pro
        35                  40                  45

-continued

```
Phe Thr Leu Ala Pro Leu Pro Arg Val Gly Ser Glu Gly Ala Thr Leu
     50                  55                  60
Lys Gly Ile Leu Arg Leu Arg Leu Thr Ile Leu Asp Asp Gly Leu Phe
 65                  70                  75                  80
Ala Pro Phe Leu Arg Ala Leu Leu Glu Ala Pro Asp Gly Leu Pro
                 85                  90                  95
Leu Gly Asp Ser Ser Tyr Arg Leu Ala Arg Val Leu Ala Thr Arg Glu
                100                 105                 110
Gly His Pro Leu Ala Gly Ala Thr Ser Trp Glu Glu Leu Lys Glu Ala
            115                 120                 125
Pro Lys Arg Glu Lys Ala Thr Phe Arg Phe Leu Thr Pro Thr Val Phe
        130                 135                 140
Ala Thr Ser Lys Pro Gly Gly Arg Thr Arg Tyr Thr Pro Leu Pro Asp
145                 150                 155                 160
Pro Arg Leu Ile Ala Gly Ser Leu Leu Asp Lys Trp Gln Ala His Ser
                165                 170                 175
Pro Phe Pro Tyr Asn Pro Lys Glu Glu Ala Ala Leu Arg Glu Leu Phe
            180                 185                 190
Glu Leu Asp Leu Glu Val Ala Gly Phe Arg Asn Leu Arg Phe His Arg
        195                 200                 205
Val Gln Ala Gly Lys Ser Phe Phe Pro Gly Phe Thr Gly Glu Met Thr
    210                 215                 220
Leu Arg Leu Trp Ser Gln Ser Leu Glu Ala Gln Gly Ala Leu Gly Arg
225                 230                 235                 240
Leu His Ala Leu Ala Phe Phe Ser Gly Val Gly Ala Lys Thr Pro Tyr
                245                 250                 255
Gly Met Gly Leu Ala Val Pro Leu
            260

<210> SEQ ID NO 28
<211> LENGTH: 20
<212> TYPE: RNA
<213> ORGANISM: Artificial sequence
<220> FEATURE:
<223> OTHER INFORMATION: Synthetic nucleic acid sequence

<400> SEQUENCE: 28
auugagcccc guaaggggau                                                  20

<210> SEQ ID NO 29
<211> LENGTH: 19
<212> TYPE: RNA
<213> ORGANISM: Artificial sequence
<220> FEATURE:
<223> OTHER INFORMATION: Synthetic nucleic acid sequence

<400> SEQUENCE: 29
cguuagccuc guagaggau                                                   19

<210> SEQ ID NO 30
<211> LENGTH: 24
<212> TYPE: RNA
<213> ORGANISM: Artificial sequence
<220> FEATURE:
<223> OTHER INFORMATION: Synthetic nucleic acid sequence

<400> SEQUENCE: 30
uacccacccc gaagaaaagg ggac                                             24
```

<210> SEQ ID NO 31
<211> LENGTH: 244
<212> TYPE: PRT
<213> ORGANISM: Staphylococcus epidermidis RP62A

<400> SEQUENCE: 31

```
Met Ile Asn Lys Ile Thr Val Glu Leu Asp Leu Pro Glu Ser Ile Arg
1               5                   10                  15

Phe Gln Tyr Leu Gly Ser Val Leu His Gly Val Leu Met Asp Tyr Leu
            20                  25                  30

Ser Asp Asp Ile Ala Asp Gln Leu His His Glu Phe Ala Tyr Ser Pro
        35                  40                  45

Leu Lys Gln Arg Ile Tyr His Lys Asn Lys Lys Ile Ile Trp Glu Ile
    50                  55                  60

Val Cys Met Ser Asp Asn Leu Phe Lys Glu Val Val Lys Leu Phe Ser
65                  70                  75                  80

Ser Lys Asn Ser Leu Leu Leu Lys Tyr Tyr Gln Thr Asn Ile Asp Ile
                85                  90                  95

Gln Ser Phe Gln Ile Glu Lys Ile Asn Val Gln Asn Met Met Asn Gln
            100                 105                 110

Leu Leu Gln Val Glu Asp Leu Ser Arg Tyr Val Arg Leu Asn Ile Gln
        115                 120                 125

Thr Pro Met Ser Phe Lys Tyr Gln Asn Ser Tyr Met Ile Phe Pro Asp
    130                 135                 140

Val Lys Arg Phe Phe Arg Ser Ile Met Ile Gln Phe Asp Ala Phe Phe
145                 150                 155                 160

Glu Glu Tyr Arg Met Tyr Asp Lys Glu Thr Leu Asn Phe Leu Glu Lys
                165                 170                 175

Asn Val Asn Ile Val Asp Tyr Lys Leu Lys Ser Thr Arg Phe Asn Leu
            180                 185                 190

Glu Lys Val Lys Ile Pro Ser Phe Thr Gly Glu Ile Val Phe Lys Ile
        195                 200                 205

Lys Gly Pro Leu Pro Phe Leu Gln Leu Thr His Phe Leu Leu Lys Phe
    210                 215                 220

Gly Glu Phe Ser Gly Ser Gly Ile Lys Thr Ser Leu Gly Met Gly Lys
225                 230                 235                 240

Tyr Ser Ile Ile
```

<210> SEQ ID NO 32
<211> LENGTH: 20
<212> TYPE: RNA
<213> ORGANISM: Artificial sequence
<220> FEATURE:
<223> OTHER INFORMATION: Synthetic nucleic acid sequence

<400> SEQUENCE: 32
ccaaaacccc gagagggggac                                              20

<210> SEQ ID NO 33
<211> LENGTH: 314
<212> TYPE: PRT
<213> ORGANISM: Mycobacterium tuberculosis H37Rv

<400> SEQUENCE: 33

```
Met Ala Ala Arg Arg Gly Gly Ile Arg Arg Thr Asp Leu Leu Arg Arg
1               5                   10                  15

Ser Gly Gln Pro Arg Gly Arg His Arg Ala Ser Ala Ala Glu Ser Gly
```

20                  25                  30
Leu Thr Trp Ile Ser Pro Thr Leu Ile Leu Val Gly Phe Ser His Arg
                35                  40                  45

Gly Asp Arg Arg Met Thr Glu His Leu Ser Arg Leu Thr Leu Thr Leu
 50                  55                  60

Glu Val Asp Ala Pro Leu Glu Arg Ala Arg Val Ala Thr Leu Gly Pro
 65                  70                  75                  80

His Leu His Gly Val Leu Met Glu Ser Ile Pro Ala Asp Tyr Val Gln
                 85                  90                  95

Thr Leu His Thr Val Pro Val Asn Pro Tyr Ser Gln Tyr Ala Leu Ala
                100                 105                 110

Arg Ser Thr Thr Ser Leu Glu Trp Lys Ile Ser Thr Leu Thr Asn Glu
                115                 120                 125

Ala Arg Gln Gln Ile Val Gly Pro Ile Asn Asp Ala Ala Phe Ala Gly
            130                 135                 140

Phe Arg Leu Arg Ala Ser Gly Ile Ala Thr Gln Val Thr Ser Arg Ser
145                 150                 155                 160

Leu Glu Gln Asn Pro Leu Ser Gln Phe Ala Arg Ile Phe Tyr Ala Arg
                165                 170                 175

Pro Glu Thr Arg Lys Phe Arg Val Glu Phe Leu Thr Pro Thr Ala Phe
                180                 185                 190

Lys Gln Ser Gly Glu Tyr Val Phe Trp Pro Asp Pro Arg Leu Val Phe
                195                 200                 205

Gln Ser Leu Ala Gln Lys Tyr Gly Ala Ile Val Asp Gly Glu Glu Pro
            210                 215                 220

Asp Pro Gly Leu Ile Ala Glu Phe Gly Gln Ser Val Arg Leu Ser Ala
225                 230                 235                 240

Phe Arg Val Ala Ser Ala Pro Phe Ala Val Gly Ala Ala Arg Val Pro
                245                 250                 255

Gly Phe Thr Gly Ser Ala Thr Phe Thr Val Arg Gly Val Asp Thr Phe
                260                 265                 270

Ala Ser Tyr Ile Ala Ala Leu Leu Trp Phe Gly Glu Phe Ser Gly Cys
                275                 280                 285

Gly Ile Lys Ala Ser Met Gly Met Gly Ala Ile Arg Val Gln Pro Leu
            290                 295                 300

Ala Pro Arg Glu Lys Cys Val Pro Lys Pro
305                 310

<210> SEQ ID NO 34
<211> LENGTH: 20
<212> TYPE: RNA
<213> ORGANISM: Artificial sequence
<220> FEATURE:
<223> OTHER INFORMATION: Synthetic nucleic acid sequence

<400> SEQUENCE: 34
uaauuaccuc gagaggggac                                          20

<210> SEQ ID NO 35
<211> LENGTH: 243
<212> TYPE: PRT
<213> ORGANISM: Streptococcus thermophilus LMG 18311

<400> SEQUENCE: 35

Met Lys Lys Leu Val Phe Thr Phe Lys Arg Ile Asp His Pro Ala Gln
 1               5                  10                  15

```
Asp Leu Ala Val Lys Phe His Gly Phe Leu Met Glu Gln Leu Asp Ser
                20                  25                  30

Asp Tyr Val Asp Tyr Leu His Gln Gln Gln Thr Asn Pro Tyr Ala Thr
            35                  40                  45

Lys Val Ile Gln Gly Lys Glu Asn Thr Gln Trp Val Val His Leu Leu
 50                  55                  60

Thr Asp Asp Ile Glu Asp Lys Val Phe Met Thr Leu Leu Gln Ile Lys
 65                  70                  75                  80

Glu Val Ser Leu Asn Asp Leu Pro Lys Leu Ser Val Glu Lys Val Glu
                85                  90                  95

Ile Gln Glu Leu Gly Ala Asp Lys Leu Leu Glu Ile Phe Asn Ser Glu
            100                 105                 110

Glu Asn Gln Thr Tyr Phe Ser Ile Ile Phe Glu Thr Pro Thr Gly Phe
        115                 120                 125

Lys Ser Gln Gly Ser Tyr Val Ile Phe Pro Ser Met Arg Leu Ile Phe
130                 135                 140

Gln Ser Leu Met Gln Lys Tyr Gly Arg Leu Val Glu Asn Gln Pro Glu
145                 150                 155                 160

Ile Glu Glu Asp Thr Leu Asp Tyr Leu Ser Glu His Ser Thr Ile Thr
                165                 170                 175

Asn Tyr Arg Leu Glu Thr Ser Tyr Phe Arg Val His Arg Gln Arg Ile
            180                 185                 190

Pro Ala Phe Arg Gly Lys Leu Thr Phe Lys Val Gln Gly Ala Gln Thr
        195                 200                 205

Leu Lys Ala Tyr Val Lys Met Leu Leu Thr Phe Gly Glu Tyr Ser Gly
210                 215                 220

Leu Gly Met Lys Thr Ser Leu Gly Met Gly Gly Ile Lys Leu Glu Glu
225                 230                 235                 240

Arg Lys Asp

<210> SEQ ID NO 36
<211> LENGTH: 20
<212> TYPE: RNA
<213> ORGANISM: Artificial sequence
<220> FEATURE:
<223> OTHER INFORMATION: Synthetic nucleic acid sequence

<400> SEQUENCE: 36
cagucaccuc gggaggggac                                              20

<210> SEQ ID NO 37
<211> LENGTH: 244
<212> TYPE: PRT
<213> ORGANISM: Streptococcus sanguinis SK36

<400> SEQUENCE: 37

Met Lys Lys Ile Arg Leu His Leu Ser Lys Val Ser Leu Lys Asp Asp
 1               5                  10                  15

Asp Leu Val Cys Lys Leu Gln Gly Phe Leu Met Glu Lys Leu Ser Asp
                20                  25                  30

Asp Phe Ala Ser Phe Leu His Gln Gln Glu Thr Asn Pro Tyr Ser Met
            35                  40                  45

Asn Leu Arg Ser Glu Arg Glu Glu Ser Ile Trp Thr Val Asn Leu Leu
 50                  55                  60

Ser Glu Glu Ala Glu Gln Gln Ile Leu Pro Gln Leu Leu Ser Leu Glu
 65                  70                  75                  80
```

```
Met Ile Lys Leu Glu Thr Tyr Ser Glu Glu Ile Leu Val Lys Asn Ile
                85                  90                  95

Glu Ile Gln Ser Leu Ser Ser Gln Ser Leu Leu Glu Val Phe Gln Gly
            100                 105                 110

Asp Glu Ala Ser His Leu Ile Ser Leu Asn Phe Tyr Thr Pro Thr Thr
            115                 120                 125

Phe Lys Arg Gln Gly Gln Phe Val Leu Phe Pro Asp Thr Arg Leu Ile
            130                 135                 140

Phe Gln Ser Leu Met Gln Lys Tyr Ser Arg Leu Val Glu Gly Lys Ala
145                 150                 155                 160

Glu Ile Glu Glu Thr Leu Glu Phe Leu Ala Glu His Ser Gln Ile
                165                 170                 175

Ser Ser Tyr Arg Leu Lys Ser His Tyr Phe Pro Ile His Gly Arg Lys
            180                 185                 190

Tyr Pro Ala Phe Glu Gly Arg Val Thr Ile Arg Ile Gln Gly Ala Ser
            195                 200                 205

Thr Leu Lys Ala Tyr Ala Gln Met Leu Leu Arg Phe Gly Glu Tyr Ser
            210                 215                 220

Gly Val Gly Ala Lys Cys Ser Leu Gly Met Gly Gly Met Arg Ile Glu
225                 230                 235                 240

Glu Arg Lys Thr

<210> SEQ ID NO 38
<211> LENGTH: 19
<212> TYPE: RNA
<213> ORGANISM: Artificial sequence
<220> FEATURE:
<223> OTHER INFORMATION: Synthetic nucleic acid sequence

<400> SEQUENCE: 38
cuuaaacccu auuagggau                                              19

<210> SEQ ID NO 39
<211> LENGTH: 277
<212> TYPE: PRT
<213> ORGANISM: Microcystis aeruginosa NIES-843

<400> SEQUENCE: 39

Met Pro Tyr Ser Leu Val Leu Asn Leu Thr Pro Arg Ser Pro Ile Tyr
1               5                   10                  15

Pro Asn Phe Leu Thr Gly Arg His Leu His Ala Leu Phe Leu Thr Leu
            20                  25                  30

Val Ser Ser Val Asp Gln Glu Leu Gly Lys Ile Leu His Thr Ala Glu
        35                  40                  45

Ala Asp Lys Ala Phe Thr Leu Ser Pro Leu Gln Met Gln Ser Gly Gly
50                  55                  60

Lys Thr Ile Asn Ser Pro Gln Trp Arg Tyr Glu Arg Pro Ile Ala Pro
65                  70                  75                  80

Glu Thr Pro Cys Trp Trp Arg Ile Ser Leu Asp Asp Arg Leu Phe
                85                  90                  95

Gly Lys Leu Thr Pro Leu Trp Leu Asn Leu Asn Pro Lys His Pro Trp
            100                 105                 110

His Leu Gly Ser Ala Asp Leu Val Ile Thr Ser Val Leu Ala Thr Pro
            115                 120                 125

Gln Ser Val Gln Pro Trp Ala Asn Ser Cys Thr Tyr Gln Tyr Leu Tyr
            130                 135                 140
```

Glu Asn Ala Ser Glu Thr Asn Arg Glu Phe Asp Phe Leu Phe Ala Thr
145                 150                 155                 160

Pro Val Thr Phe Arg Gln Gly Lys Phe Asp Ser Ala Leu Pro Thr Arg
            165                 170                 175

Glu Leu Val Phe Asn Ser Leu Leu Asn Arg Trp Asn Arg Tyr Ser Ala
            180                 185                 190

Ile Pro Phe Asp Ser Ile Val Leu Glu Ser Ile Phe Pro Ser Phe Phe
            195                 200                 205

Asp Ile Gln Thr Lys Leu Ala Asp Glu Ala Tyr Lys Asn Gln Ser Phe
            210                 215                 220

Gly Cys Val Gly Glu Ile His Tyr Arg Leu Leu Gly Glu Val Glu Pro
225                 230                 235                 240

Ala Lys Ile Lys Ala Ile Asn Val Leu Ala Asp Phe Ala Leu Tyr Ala
            245                 250                 255

Gly Val Gly Arg Lys Thr Thr Met Gly Met Gly Met Thr Arg Arg Ile
            260                 265                 270

Ala Lys Glu Lys Arg
            275

<210> SEQ ID NO 40
<211> LENGTH: 32
<212> TYPE: RNA
<213> ORGANISM: Artificial sequence
<220> FEATURE:
<223> OTHER INFORMATION: Synthetic nucleic acid sequence

<400> SEQUENCE: 40 gucgccccc acgcggggc guggauugaa ac                                    32

<210> SEQ ID NO 41
<211> LENGTH: 227
<212> TYPE: PRT
<213> ORGANISM: Desulfovibrio vulgaris DP4

<400> SEQUENCE: 41

Met Thr His Gly Ala Val Lys Thr Tyr Gly Ile Arg Leu Arg Val Trp
1               5                   10                  15

Gly Asp Tyr Ala Cys Phe Thr Arg Pro Glu Met Lys Val Glu Arg Val
            20                  25                  30

Ser Tyr Asp Val Met Thr Pro Ser Ala Ala Arg Gly Ile Leu Glu Ala
            35                  40                  45

Ile His Trp Lys Pro Ala Ile Arg Trp Ile Val Asp Arg Ile His Val
        50                  55                  60

Leu Arg Pro Ile Val Phe Asp Asn Val Arg Arg Asn Glu Val Ser Ser
65                  70                  75                  80

Lys Ile Pro Lys Pro Asn Pro Ala Thr Ala Met Arg Asp Arg Lys Pro
            85                  90                  95

Leu Tyr Phe Leu Val Asp Asp Gly Ser Asn Arg Gln Gln Arg Ala Ala
            100                 105                 110

Thr Leu Leu Arg Asn Val Asp Tyr Val Ile Glu Ala His Phe Glu Leu
            115                 120                 125

Thr Asp Lys Ala Gly Ala Glu Asp Asn Ala Gly Lys His Leu Asp Ile
            130                 135                 140

Phe Arg Arg Arg Ala Arg Ala Gly Gln Ser Phe Gln Gln Pro Cys Leu
145                 150                 155                 160

Gly Cys Arg Glu Phe Pro Ala Ser Phe Glu Leu Leu Glu Gly Asp Val
            165                 170                 175

```
Pro Leu Ser Cys Tyr Ala Gly Glu Lys Arg Asp Leu Gly Tyr Met Leu
            180                 185                 190

Leu Asp Ile Asp Phe Glu Arg Asp Met Thr Pro Leu Phe Phe Lys Ala
            195                 200                 205

Val Met Glu Asp Gly Val Ile Thr Pro Pro Ser Arg Thr Ser Pro Glu
210                 215                 220

Val Arg Ala
225

<210> SEQ ID NO 42
<211> LENGTH: 227
<212> TYPE: PRT
<213> ORGANISM: Methylomonas methanica MC09

<400> SEQUENCE: 42

Met Ala Tyr Gly Ile Lys Leu His Ile Trp Gly Asp Tyr Ala Cys Phe
1               5                   10                  15

Thr Arg Pro Glu Met Lys Val Glu Arg Val Ser Tyr Asp Val Ile Thr
            20                  25                  30

Pro Ser Ala Ala Arg Gly Ile Leu Glu Ala Ile His Trp Lys Pro Ala
        35                  40                  45

Ile Arg Trp Val Ile Asp Lys Ile His Val Leu Gln Pro Val Arg Phe
50                  55                  60

Glu Ser Ile Arg Arg Asn Glu Val Gly Ser Lys Ile Ser Ala Ala Lys
65                  70                  75                  80

Ile Lys Thr Ala Met Arg Asn Gln Ser Thr Gln Asp Leu Tyr Leu Val
            85                  90                  95

Ala Asp Asp Ala Lys Glu Arg Gln Gln Arg Ala Ser Thr Val Leu Arg
        100                 105                 110

Asn Val Ala Tyr Ile Ile Glu Ala His Phe Glu Leu Thr Asp Leu Ala
        115                 120                 125

Thr Asp Glu Asp Asn Glu Gly Lys His Leu Asp Ile Phe Asn Arg Arg
    130                 135                 140

Ala Arg Lys Gly Gln Cys Phe Gln Gln Pro Cys Met Gly Val Arg Glu
145                 150                 155                 160

Phe Pro Ala Tyr Phe Ala Leu Ile Glu Pro Glu Gln Ser Leu Pro Glu
                165                 170                 175

Ser Glu Leu Thr Pro Glu Gln Leu Asn Arg Asp Leu Gly Trp Met Leu
            180                 185                 190

His Asp Ile Asp Phe Ala Asn Gly Met Met Pro His Phe Phe Lys Ala
            195                 200                 205

Glu Leu Lys Gly Gly Ile Ile Thr Val Pro Asp Phe Tyr Ser Glu Gly
        210                 215                 220

Val Lys Ala
225

<210> SEQ ID NO 43
<211> LENGTH: 227
<212> TYPE: PRT
<213> ORGANISM: Nitrosomonas sp. AL212

<400> SEQUENCE: 43

Met Ala Tyr Gly Ile Lys Leu His Ile Trp Gly Asp Tyr Ala Cys Phe
1               5                   10                  15

Thr Arg Pro Glu Met Lys Val Glu Arg Val Ser Tyr Asp Val Ile Thr
            20                  25                  30
```

-continued

Pro Ser Ala Ala Arg Gly Ile Leu Asp Ala Ile His Trp Lys Pro Ala
        35                  40                  45

Ile Arg Trp Val Ile Asp Lys Ile His Val Leu Arg Pro Val Arg Phe
50                  55                  60

Glu Ser Ile Arg Arg Asn Glu Val Gly Ser Lys Ile Ser Ala Asn Lys
65                  70                  75                  80

Ile Lys Thr Ala Met Arg Asn Gln Ser Thr Gln Asp Leu Tyr Leu Val
                85                  90                  95

Ala Asp Asp Ser Lys Glu Arg Gln Gln Arg Ala Ser Thr Val Leu Arg
                100                 105                 110

Asn Val Ala Tyr Ile Ile Glu Ala His Phe Glu Leu Thr Asp Leu Ala
                115                 120                 125

Ser Glu Glu Asp Ser Gly Lys His Leu Asp Ile Phe Asn Arg Arg
130                 135                 140

Ala Arg Lys Gly Gln Cys Phe Gln Gln Pro Cys Met Gly Val Arg Glu
145                 150                 155                 160

Phe Pro Ala Tyr Phe Ser Leu Ile Glu Pro Glu Ser Leu Pro Glu
                165                 170                 175

Ser Glu Leu Thr Leu Gln Leu Asn Arg Asp Leu Gly Trp Met Leu
                180                 185                 190

His Asp Ile Asp Phe Ala Asn Glu Met Met Pro Arg Phe Phe Lys Ala
                195                 200                 205

Glu Leu Lys Asn Gly Val Ile Thr Val Pro Asp Phe Tyr Ser Asp Glu
210                 215                 220

Val Lys Ala
225

<210> SEQ ID NO 44
<211> LENGTH: 225
<212> TYPE: PRT
<213> ORGANISM: Vibrio metschnikovii CIP 69.14

<400> SEQUENCE: 44

Met Ala Tyr Gly Ile Lys Leu His Val Trp Gly Glu Tyr Ala Cys Phe
1               5                   10                  15

Thr Arg Pro Glu Met Lys Val Glu Arg Val Ser Tyr Asp Val Ile Thr
                20                  25                  30

Pro Ser Ala Ala Arg Gly Ile Leu Glu Ala Ile His Trp Lys Pro Ala
        35                  40                  45

Ile Ile Trp Val Ile Asp Arg Ile His Val Leu Lys Pro Val Arg Phe
50                  55                  60

Glu Ser Ile Arg Arg Asn Glu Leu Gly Asn Cys Lys Val Ser Ser Ala
65                  70                  75                  80

Lys Val Ser Gly Ala Met Lys Arg Lys Ser Thr Gln Asp Leu Ser Phe
                85                  90                  95

Leu Ile Asp Asp Gly Asp Asn Arg Gln Gln Arg Ala Thr Thr Leu Leu
                100                 105                 110

Arg Asp Val Ser Tyr Val Ile Glu Ala His Phe Glu Leu Ser Asp Lys
                115                 120                 125

Ala Gly Thr Glu Asp Ser Ile Gly Lys His Leu Asp Ile Phe Asn Arg
                130                 135                 140

Arg Ala Arg Arg Gly Gln Tyr Phe His Gln Pro Cys Leu Gly Asn Arg
145                 150                 155                 160

Glu Phe Pro Ala Tyr Phe Ser Leu Ile Glu His Glu Trp Asp Phe Pro

```
            165                 170                 175
Lys Ser Glu Leu Ala Thr Ala Ser Lys Asp Leu Gly Trp Met Leu His
            180                 185                 190

Asp Ile Asp Phe Ala Asn Gly Ala Glu Pro Arg Phe Arg Ala Glu
            195                 200                 205

Leu Lys Asp Gly Met Ile Asp Val Pro Pro Phe Arg Ser Ser Lys Val
210                 215                 220

Val
225

<210> SEQ ID NO 45
<211> LENGTH: 218
<212> TYPE: PRT
<213> ORGANISM: Desulfotomaculum carboxydivorans CO-1-SRB

<400> SEQUENCE: 45

Met Gly Tyr Gly Ile Lys Leu Lys Val Trp Gly Asp Tyr Ala Cys Phe
1               5                   10                  15

Ser Arg Pro Glu Met Lys Val Glu Arg Val Ser Tyr Asp Val Met Thr
            20                  25                  30

Pro Ser Ala Ala Arg Gly Ile Leu Glu Ala Ile His Trp Lys Pro Ala
        35                  40                  45

Ile Arg Trp Val Val Asp Arg Ile His Ile Leu Asn Ala Phe Lys Phe
    50                  55                  60

Glu Asn Ile Arg Arg Asn Glu Val Gly Thr Lys Ile Pro Ala Gly Thr
65                  70                  75                  80

Val Lys Thr Ala Met Lys Gly Gln Pro Val Met Leu Cys Gln Tyr Ala
                85                  90                  95

Ser Asn Glu Arg Gln Gln Arg Ala Thr Leu Leu Leu Lys Asp Val Ala
            100                 105                 110

Tyr Val Ile Glu Ala His Phe Glu Met Thr Asp Lys Ala Gly Pro Thr
        115                 120                 125

Asp Thr Glu Glu Lys His Tyr Asn Met Phe Leu Arg Arg Ala Arg Thr
    130                 135                 140

Gly Gln Cys Phe His Arg Pro Tyr Leu Gly Cys Arg Glu Phe Pro Ala
145                 150                 155                 160

His Phe Glu Leu Leu Glu Gly Glu Asn Pro Ile Ser Val His Arg Gly
                165                 170                 175

Glu Lys Asp Leu Gly Trp Met Leu Leu Asp Ile Asp Tyr Lys Asn Asn
            180                 185                 190

Met Glu Pro His Phe Phe Arg Ala Val Met Gln Asp Gly Val Val Thr
        195                 200                 205

Val Pro Pro Leu Lys Gly Gly Gly Ser Leu
    210                 215

<210> SEQ ID NO 46
<211> LENGTH: 224
<212> TYPE: PRT
<213> ORGANISM: Neisseria mucosa ATCC 25996

<400> SEQUENCE: 46

Met Asn Gln Ile Arg Leu His Val Trp Gly Asp Tyr Ala Cys Phe Thr
1               5                   10                  15

Arg Pro Glu Met Lys Val Glu Arg Val Ser Tyr Asp Val Ile Thr Pro
            20                  25                  30

Ser Ala Ala Arg Gly Ile Leu Ala Ala Val His Trp Lys Pro Ala Ile
```

```
            35                  40                  45
Arg Trp Val Ile Asp Arg Ile Tyr Val Leu Lys Pro Ile Arg Phe Glu
 50                  55                  60
Ser Val Arg Arg Asn Glu Leu Gly Gly Lys Ile Ser Ala Gly Lys Val
 65                  70                  75                  80
Ser Gly Ala Met Lys Arg Lys Ser Val Ala Asp Leu Tyr Thr Leu Ile
                 85                  90                  95
Glu Asp Asp Arg Gln Gln Arg Ala Ala Thr Val Leu Lys Asp Val Ala
            100                 105                 110
Tyr Val Ile Glu Ala His Ala Val Leu Thr Ala Lys Ala Gly Ala Asp
        115                 120                 125
Glu Thr Val Thr Lys His Ile Glu Met Phe Lys Arg Arg Ala Lys Lys
    130                 135                 140
Gly Gln Cys Phe Gln Gln Pro Cys Leu Gly Val Arg Glu Phe Pro Ala
145                 150                 155                 160
Asp Phe Ala Leu Ile Asp Glu Gly Glu Pro Leu Pro Pro Ser Ala Leu
                165                 170                 175
Ser Glu Ser Glu Ala Asn Arg Asp Leu Gly Trp Met Leu His Asp Ile
            180                 185                 190
Asp Phe Asp His Gly Asn Thr Pro His Phe Phe Arg Ala Gln Met Lys
        195                 200                 205
Asp Gly Val Ile Asp Val Pro Pro Phe Tyr Ala Glu Glu Val Lys Ala
    210                 215                 220

<210> SEQ ID NO 47
<211> LENGTH: 236
<212> TYPE: PRT
<213> ORGANISM: Bacillus halodurans C-125

<400> SEQUENCE: 47

Met Arg Asn Glu Val Gln Phe Glu Leu Phe Gly Asp Tyr Ala Leu Phe
  1               5                  10                  15
Thr Asp Pro Leu Thr Lys Ile Gly Gly Glu Lys Leu Ser Tyr Ser Val
             20                  25                  30
Pro Thr Tyr Gln Ala Leu Lys Gly Ile Ala Glu Ser Ile Tyr Trp Lys
         35                  40                  45
Pro Thr Ile Val Phe Val Ile Asp Glu Leu Arg Val Met Lys Pro Ile
     50                  55                  60
Gln Met Glu Ser Lys Gly Val Arg Pro Ile Glu Tyr Gly Gly Gly Asn
 65                  70                  75                  80
Thr Leu Ala His Tyr Thr Tyr Leu Lys Asp Val His Tyr Gln Val Lys
                 85                  90                  95
Ala His Phe Glu Phe Asn Leu His Arg Pro Asp Leu Ala Phe Asp Arg
            100                 105                 110
Asn Glu Gly Lys His Tyr Ser Ile Leu Gln Arg Ser Leu Lys Ala Gly
        115                 120                 125
Gly Arg Arg Asp Ile Phe Leu Gly Ala Arg Glu Cys Gln Gly Tyr Val
    130                 135                 140
Ala Pro Cys Glu Phe Gly Ser Gly Asp Gly Phe Tyr Asp Gly Gln Gly
145                 150                 155                 160
Lys Tyr His Leu Gly Thr Met Val His Gly Phe Asn Tyr Pro Asp Glu
                165                 170                 175
Thr Gly Gln His Gln Leu Asp Val Arg Leu Trp Ser Ala Val Met Glu
            180                 185                 190
```

```
Asn Gly Tyr Ile Gln Phe Pro Arg Pro Glu Asp Cys Pro Ile Val Arg
        195                 200                 205

Pro Val Lys Glu Met Glu Pro Lys Ile Phe Asn Pro Asp Asn Val Gln
    210                 215                 220

Ser Ala Glu Gln Leu Leu His Asp Leu Gly Gly Glu
225                 230                 235

<210> SEQ ID NO 48
<211> LENGTH: 246
<212> TYPE: PRT
<213> ORGANISM: Bacillus cereus F65185

<400> SEQUENCE: 48

Met Lys Lys Glu Glu Glu Ser Leu Arg Asn Ser Ile Glu Phe Glu Val
1               5                   10                  15

Phe Gly Asp Tyr Ala Leu Phe Thr Asp Pro Leu Met Lys Met Gly Gly
            20                  25                  30

Glu Lys Leu Thr Tyr Gln Val Pro Thr Tyr Gln Ala Ile Lys Gly Ile
        35                  40                  45

Val Glu Ser Ile Tyr Trp Lys Pro Thr Leu Leu Met Ile Val Asp Lys
    50                  55                  60

Ile Arg Ile Met Asn Ala Ile Lys Met Glu Ser Lys Gly Ile Arg Pro
65                  70                  75                  80

Ile Glu Tyr Gly Gly Gly Asn Thr Leu Ala Asn Tyr Thr Tyr Leu Lys
                85                  90                  95

Asn Val Arg Tyr Gln Val Gln Ala His Phe Ile Phe Asn Pro His Arg
            100                 105                 110

Pro Asp Leu Ala Phe Asp Arg Asn Glu Tyr Lys His His Asn Ile Leu
        115                 120                 125

Lys Arg Ser Leu Lys Val Gly Gly Arg Arg Asp Ile Phe Leu Gly Thr
    130                 135                 140

Arg Glu Cys Gln Gly Tyr Val Glu Pro Cys Val Phe Gly Glu Gly Glu
145                 150                 155                 160

Gly Phe Tyr Asp Asn Tyr Gly Gly Asp Ile His Leu Gly Thr Met Val
                165                 170                 175

His Gly Leu Asn Tyr Pro Asp Glu Thr Gly Arg Asn Glu Leu Glu Val
            180                 185                 190

Arg Leu Trp Asn Pro Val Met Arg Asp Gly Ile Ile Gln Phe Ile Arg
        195                 200                 205

Pro Glu Glu Cys Thr Lys Ile Arg Lys Ile Ser Lys Met Glu Pro Lys
    210                 215                 220

Ile Phe Asp Ser Ser Asn Val Glu Ser Val Asp Glu Leu Ile Lys Gln
225                 230                 235                 240

Leu Glu Glu Gly Gly Glu
                245

<210> SEQ ID NO 49
<211> LENGTH: 239
<212> TYPE: PRT
<213> ORGANISM: Selenomonas noxia ATCC 43541

<400> SEQUENCE: 49

Met Arg Asn Ser Ile Glu Phe Gln Val Tyr Gly Arg Met Ala Leu Phe
1               5                   10                  15

Thr Asp Pro Ile Thr Lys Ile Gly Gly Glu Lys Ala Ser Tyr Ser Val
            20                  25                  30
```

Pro Thr Tyr Gln Ala Leu Lys Gly Ile Thr Glu Ser Ile Tyr Trp Lys
         35                  40                  45

Pro Thr Ile Ile Trp Phe Ile Asp Glu Val Arg Val Met Lys Arg Ile
 50                  55                  60

Thr Thr Gln Val Arg Gly Val Lys Pro Leu Lys Tyr Gly Asp Ser Gly
 65                  70                  75                  80

Asn Asp Leu Ser Tyr Tyr Lys Tyr Leu Ser Asp Val Cys Tyr Gln Val
                 85                  90                  95

Arg Ala His Phe Glu Phe Asn Met His Arg Glu Glu Leu Lys Glu Asp
             100                 105                 110

Arg Asp Glu His Lys His His Asn Ile Ala Lys Arg Met Val Glu Arg
         115                 120                 125

Gly Gly Arg Arg Asp Ile Phe Leu Gly Thr Arg Glu Cys Gln Gly Tyr
130                 135                 140

Val Glu Pro Val Lys Tyr Gly Val Lys Gly Tyr Tyr Asp Asn Val
145                 150                 155                 160

Asp Glu Leu Pro Leu Gly Ile Met Leu His Gly Phe Asn Tyr Pro Asp
                165                 170                 175

Glu Thr Gly Glu Asp Lys Leu Gln Val Arg Phe Trp Lys Pro Thr Met
            180                 185                 190

Lys Lys Gly Ile Ile His Phe Arg Arg Pro Glu Lys Cys Glu Met Val
        195                 200                 205

Arg Asp Ile Arg Glu Val Arg Thr Lys Gln Phe Asp Ala Asp Asn Val
    210                 215                 220

Phe Phe Ala Glu Glu Glu Lys Gln Leu Glu Gly Gly His Leu
225                 230                 235

<210> SEQ ID NO 50
<211> LENGTH: 33
<212> TYPE: RNA
<213> ORGANISM: Artificial sequence
<220> FEATURE:
<223> OTHER INFORMATION: Synthetic nucleic acid sequence

<400> SEQUENCE: 50
gucgcgcccc gcaugggggcg cguggauuga aac                            33

<210> SEQ ID NO 51
<211> LENGTH: 66
<212> TYPE: RNA
<213> ORGANISM: Artificial sequence
<220> FEATURE:
<223> OTHER INFORMATION: Synthetic nucleic acid sequence
<220> FEATURE:
<221> NAME/KEY: misc_feature
<222> LOCATION: (22)..(66)
<223> OTHER INFORMATION: n in any of these positions can be any base
      (e.g., a,g,c,t) and can be present or absent such that this entire
      region may be absent. This region may also be of any desired
      length (e.g., 4,000 "n"s, 3000 "n"s, 2,500 "n"s, etc.).

<400> SEQUENCE: 51
gucgcccccc acgcggggggc gnnnnnnnnn nnnnnnnnnn nnnnnnnnnn nnnnnnnnnn     60 nnnnnn                                                                66

<210> SEQ ID NO 52
<211> LENGTH: 21
<212> TYPE: RNA
<213> ORGANISM: Artificial sequence
<220> FEATURE:
<223> OTHER INFORMATION: Synthetic nucleic acid sequence

<400> SEQUENCE: 52 gucgccccccc acgcggggc g                                           21

<210> SEQ ID NO 53
<211> LENGTH: 30
<212> TYPE: RNA
<213> ORGANISM: Artificial sequence
<220> FEATURE:
<223> OTHER INFORMATION: Synthetic nucleic acid sequence

<400> SEQUENCE: 53
guugcaaggg auugagcccc guaaggggau                                  30

<210> SEQ ID NO 54
<211> LENGTH: 30
<212> TYPE: RNA
<213> ORGANISM: Artificial sequence
<220> FEATURE:
<223> OTHER INFORMATION: Synthetic nucleic acid sequence

<400> SEQUENCE: 54
guugcaaacc ucguuagccu cguagaggau                                  30

<210> SEQ ID NO 55
<211> LENGTH: 29
<212> TYPE: RNA
<213> ORGANISM: Artificial sequence
<220> FEATURE:
<223> OTHER INFORMATION: Synthetic nucleic acid sequence

<400> SEQUENCE: 55
guagucccca cgcguguggg gauggaccg                                   29

<210> SEQ ID NO 56
<211> LENGTH: 14
<212> TYPE: RNA
<213> ORGANISM: Artificial sequence
<220> FEATURE:
<223> OTHER INFORMATION: Synthetic nucleic acid sequence

<400> SEQUENCE: 56
ccccguaagg ggau                                                   14

<210> SEQ ID NO 57
<211> LENGTH: 18
<212> TYPE: RNA
<213> ORGANISM: Artificial sequence
<220> FEATURE:
<223> OTHER INFORMATION: Synthetic nucleic acid sequence

<400> SEQUENCE: 57
gguugcaagg ggauugag                                               18

<210> SEQ ID NO 58
<211> LENGTH: 244
<212> TYPE: PRT
<213> ORGANISM: Artificial sequence
<220> FEATURE:
<223> OTHER INFORMATION: Synthetic amino acid sequence

<400> SEQUENCE: 58

His His His His Gly Ser Arg Phe Leu Ile Arg Leu Val Pro Glu Asp
 1               5                   10                  15

Lys Asp Arg Ala Phe Lys Val Pro Tyr Asn His Gln Tyr Tyr Leu Gln

```
                    20                  25                  30
Gly Leu Ile Tyr Asn Ala Ile Lys Ser Ser Asn Pro Lys Leu Ala Thr
                35                  40                  45

Tyr Leu His Glu Val Lys Gly Pro Lys Leu Phe Thr Tyr Ser Leu Phe
 50                  55                  60

Met Ala Glu Lys Arg Glu His Pro Lys Gly Leu Pro Tyr Phe Leu Gly
 65                  70                  75                  80

Tyr Lys Lys Gly Phe Phe Tyr Phe Ser Thr Cys Val Pro Glu Ile Ala
                 85                  90                  95

Glu Ala Leu Val Asn Gly Leu Leu Met Asn Pro Glu Val Arg Leu Trp
                100                 105                 110

Asp Glu Arg Phe Tyr Leu His Glu Ile Lys Val Leu Arg Glu Pro Lys
                115                 120                 125

Lys Phe Asn Gly Ser Thr Phe Val Thr Leu Ser Pro Ile Ala Val Thr
                130                 135                 140

Val Val Arg Lys Gly Lys Ser Tyr Asp Val Pro Pro Met Glu Lys Glu
145                 150                 155                 160

Phe Tyr Ser Ile Ile Lys Asp Asp Leu Gln Asp Lys Tyr Val Met Ala
                165                 170                 175

Tyr Gly Asp Lys Pro Pro Ser Glu Phe Glu Met Glu Val Leu Ile Ala
                180                 185                 190

Lys Pro Lys Arg Phe Arg Ile Lys Pro Gly Ile Tyr Gln Thr Ala Trp
                195                 200                 205

His Leu Val Phe Arg Ala Tyr Gly Asn Asp Asp Leu Leu Lys Val Gly
                210                 215                 220

Tyr Glu Val Gly Phe Gly Glu Lys Asn Ser Leu Gly Phe Gly Met Val
225                 230                 235                 240

Lys Val Glu Gly

<210> SEQ ID NO 59
<211> LENGTH: 215
<212> TYPE: PRT
<213> ORGANISM: Artificial sequence
<220> FEATURE:
<223> OTHER INFORMATION: Synthetic amino acid sequence

<400> SEQUENCE: 59

Gly Thr Gly Ala Met Trp Leu Thr Lys Leu Val Leu Asn Pro Ala Ser
 1               5                  10                  15

Arg Ala Ala Arg Arg Asp Leu Ala Asn Pro Tyr Glu Met His Arg Thr
                20                  25                  30

Leu Ser Lys Ala Val Ser Arg Ala Leu Glu Glu Gly Arg Glu Arg Leu
                35                  40                  45

Leu Trp Arg Leu Glu Pro Ala Arg Gly Leu Glu Pro Pro Val Val Leu
 50                  55                  60

Val Gln Thr Leu Thr Glu Pro Asp Trp Ser Val Leu Asp Glu Gly Tyr
 65                  70                  75                  80

Ala Gln Val Phe Pro Pro Lys Pro Phe His Pro Ala Leu Lys Pro Gly
                 85                  90                  95

Gln Arg Leu Arg Phe Arg Leu Arg Ala Asn Pro Ala Lys Arg Leu Ala
                100                 105                 110

Ala Thr Gly Lys Arg Val Ala Leu Lys Thr Pro Ala Glu Lys Val Ala
                115                 120                 125

Trp Leu Glu Arg Arg Leu Glu Glu Gly Gly Phe Arg Leu Leu Glu Gly
                130                 135                 140
```

```
Glu Arg Gly Pro Trp Val Gln Ile Leu Gln Asp Thr Phe Leu Glu Val
145                 150                 155                 160

Arg Arg Lys Lys Asp Gly Glu Ala Gly Lys Leu Leu Gln Val Gln
                165                 170                 175

Ala Val Leu Phe Glu Gly Arg Leu Glu Val Val Asp Pro Glu Arg Ala
                180                 185                 190

Leu Ala Thr Leu Arg Arg Gly Val Gly Pro Gly Lys Ala Leu Gly Leu
                195                 200                 205

Gly Leu Leu Ser Val Ala Pro
210                 215
```

<210> SEQ ID NO 60
<211> LENGTH: 188
<212> TYPE: PRT
<213> ORGANISM: Artificial sequence
<220> FEATURE:
<223> OTHER INFORMATION: Synthetic amino acid sequence

<400> SEQUENCE: 60

```
Thr Met Asp His Tyr Leu Asp Ile Arg Leu Arg Pro Asp Pro Glu Phe
1               5                   10                  15

Pro Pro Ala Gln Leu Met Ser Val Leu Phe Gly Lys Leu His Gln Ala
                20                  25                  30

Leu Val Ala Gln Gly Gly Asp Arg Ile Gly Val Ser Phe Pro Asp Leu
                35                  40                  45

Asp Glu Ser Arg Ser Arg Leu Gly Glu Arg Leu Arg Ile His Ala Ser
        50                  55                  60

Ala Asp Asp Leu Arg Ala Leu Leu Ala Arg Pro Trp Leu Glu Gly Leu
65                  70                  75                  80

Arg Asp His Leu Gln Phe Gly Glu Pro Ala Val Val Pro His Pro Thr
                85                  90                  95

Pro Tyr Arg Gln Val Ser Arg Val Gln Ala Lys Ser Asn Pro Glu Arg
                100                 105                 110

Leu Arg Arg Arg Leu Met Arg Arg His Asp Leu Ser Glu Glu Glu Ala
                115                 120                 125

Arg Lys Arg Ile Pro Asp Thr Val Ala Arg Ala Leu Asp Leu Pro Phe
                130                 135                 140

Val Thr Leu Arg Ser Gln Ser Thr Gly Gln His Phe Arg Leu Phe Ile
145                 150                 155                 160

Arg His Gly Pro Leu Gln Val Thr Ala Glu Glu Gly Gly Phe Thr Cys
                165                 170                 175

Tyr Gly Leu Ser Lys Gly Gly Phe Val Pro Trp Phe
                180                 185
```